US012661179B2

(12) United States Patent
Liu et al.

(10) Patent No.: US 12,661,179 B2
(45) Date of Patent: Jun. 23, 2026

(54) ABLATION CATHETER AND ABLATION SYSTEM

(71) Applicant: HANGZHOU DINOVA EP TECHNOLOGY CO., LTD, Zhejiang (CN)

(72) Inventors: Cheng Liu, Hangzhou (CN); Kun Wang, Hangzhou (CN)

(73) Assignee: Hangzhou Dinova EP Technology Co., Ltd., Hangzhou (CN)

( * ) Notice: Subject to any disclaimer, the term of this patent is extended or adjusted under 35 U.S.C. 154(b) by 302 days.

(21) Appl. No.: 18/446,285

(22) Filed: Aug. 8, 2023

(65) Prior Publication Data

US 2023/0380897 A1     Nov. 30, 2023

Related U.S. Application Data

(63) Continuation of application No. PCT/CN2022/075720, filed on Feb. 9, 2022.

(30) Foreign Application Priority Data

Feb. 9, 2021    (CN) .......................... 202110175103.1

(51) Int. Cl.
*A61B 18/14*         (2006.01)
*A61B 18/00*         (2006.01)

(52) U.S. Cl.
CPC ..................... *A61B 18/1492* (2013.01); *A61B 2018/00267* (2013.01); *A61B 2018/00577* (2013.01)

(58) Field of Classification Search
CPC ................ A61B 18/1492; A61B 18/12; A61B 2018/00267; A61B 2018/00577; A61B 2018/00083; A61B 2018/00196; A61B 2018/00214; A61B 2018/0022; A61B 2018/00261; A61B 2018/00375;
(Continued)

(56) References Cited

U.S. PATENT DOCUMENTS

2002/0177765 A1    11/2002  Bowe et al.
2004/0116965 A1     6/2004  Falkenberg
(Continued)

FOREIGN PATENT DOCUMENTS

CN        110179535  A     8/2019
CN        212165887  U    12/2020
(Continued)

OTHER PUBLICATIONS

International Search Report dated Apr. 27, 2022 for corresponding PCT Application No. PCT/CN2022/075720.
(Continued)

*Primary Examiner* — Ankit D Tejani
*Assistant Examiner* — Joshua Brendon Solomon

(57) ABSTRACT

An ablation catheter and an ablation system are provided. The ablation catheter includes a sheath and an ablation assembly. The ablation assembly is disposed at a distal end of the sheath for performing ablation and isolation on a target tissue area. The ablation system includes the ablation device and a mapping device, the mapping device includes a mapping electrode arranged at a distal end of the ablation catheter, and the mapping electrode is used for collecting electrophysiological signals in the target tissue area.

17 Claims, 36 Drawing Sheets

(58) Field of Classification Search
CPC . A61B 5/287; A61B 5/6858; A61B 2018/144;
A61B 2018/1475; A61B 2018/00613;
A61B 2018/00839; A61B 2018/1435;
A61B 2018/00351
See application file for complete search history.

(56) References Cited

U.S. PATENT DOCUMENTS

| | | | |
|---|---|---|---|
| 2006/0135953 | A1 | 6/2006 | Kania et al. |
| 2014/0257069 | A1 | 9/2014 | Ellason et al. |
| 2019/0029754 | A1 | 1/2019 | Dong et al. |
| 2020/0000518 | A1* | 1/2020 | Kiernan ............... A61B 5/6853 |

FOREIGN PATENT DOCUMENTS

| | | | |
|---|---|---|---|
| EP | 0916360 | A2 | 5/1999 |
| EP | 4173581 | A1 | 5/2023 |
| WO | 2022001908 | A1 | 1/2022 |

OTHER PUBLICATIONS

Written Opinion dated Apr. 22, 2022 for corresponding PCT Application No. PCT/CN2022/075720.
The Extended European Search Report Dated Mar. 27, 2025 for Corresponding European Patent Application No. 22752302.4.

\* cited by examiner

44

40b

42

40a 44          43

42          41

725
721
71

721 { 721b
721a 723
722
71

ABLATION CATHETER AND ABLATION SYSTEM

CROSS-REFERENCE TO RELATED APPLICATIONS

The present application is a Continuation application of PCT Application No. PCT/CN2022/075720, filed on Feb. 9, 2022, which claims the priority of Chinese Patent Application No. 202110175103.1, filed on Feb. 9, 2021, the entire contents of which are hereby incorporated by reference.

TECHNICAL FIELD

The disclosure relates to the technical field of interventional medical devices, and in particular, to an ablation catheter, an ablation device with the ablation catheter, and an ablation system with the ablation device.

DESCRIPTION OF THE PRIOR ART

Atrial fibrillation (AF) is the most common sustained arrhythmia. The occurrence of AF increases with age, with a prevalence of 10% of people over 75 years old. During atrial fibrillation, the frequency of atrial pacing reaches 300-600 beats/min, and the heartbeat is often rapid and irregular, sometimes with a heart rate up to 100-160 beats/min, which is faster than a normal heart rate, with arrhythmia and poor atrial contraction. Atrial fibrillation often increases the risk of many potentially lethal complications, including thromboembolic stroke, dilated cardiomyopathy, and congestive heart failure. Common AF symptoms such as palpitations, chest pain, dyspnea, fatigue, and dizziness can also affect quality of life. People with atrial fibrillation have a five-fold increase in morbidity and a three-fold increase in mortality than normal people.

Tissue ablation is usually used to treat various cardiac arrhythmias, including atrial fibrillation. To treat cardiac arrhythmias, an ablation catheter is used to perform ablation to alter tissue properties, for example, to prevent abnormal electrical propagation and/or disrupt abnormal electrical conduction through cardiac tissue. Ablation therapy includes thermal ablation, such as radiofrequency ablation, laser ablation, microwave ablation, thermal substance ablation, etc., and pulse ablation using bioelectroporation.

SUMMARY OF THE DISCLOSURE

In order to solve or at least alleviate the above-mentioned technical problems, one aspect of the present disclosure provides an ablation catheter, which includes a sheath and an ablation assembly provided at a distal end of the sheath. The ablation assembly includes an ablation element configured to perform ablation and isolation on the target tissue area.

A further aspect of the present disclosure provides an ablation system, which includes the above-mentioned ablation device and a mapping device including a mapping electrode provided at a distal end of the ablation catheter. The mapping electrode is configured for detecting electrophysiological signals in the target tissue area.

BRIEF DESCRIPTION OF DRAWINGS

In order to describe the technical solutions according to the embodiments of the present disclosure more clearly, the drawings accompanying the embodiments are briefly introduced below. Apparently, the drawings below only illustrate some embodiments of the present invention, and those skilled in the art can obtain other drawings based on the drawings below without creative work.

DESCRIPTION OF EMBODIMENTS

The technical solutions according to the embodiments of the present disclosure will be clearly and completely described in the following with reference to the accompanying drawings according to the embodiments of the present disclosure. Apparently, the described embodiments are only some, not all, embodiments of the present invention. Based on the embodiments of the present disclosure, all other embodiments obtained by those skilled in the art without creative efforts fall into the protection scope of the present invention.

Herein, "proximal end" refers to the end close to the operator during the procedure, and "distal end" refers to the end away from the operator during the procedure. The axial direction refers to the extension direction of the central axis of the device, and the radial direction refers to the direction perpendicular to the central axis. These definitions are only for the convenience of description and cannot be understood as limitations on the present invention. "Component A being connected with component B" refers that component A is directly connected with component B, or component A is indirectly connected with component B via other component (s).

Figure 1:
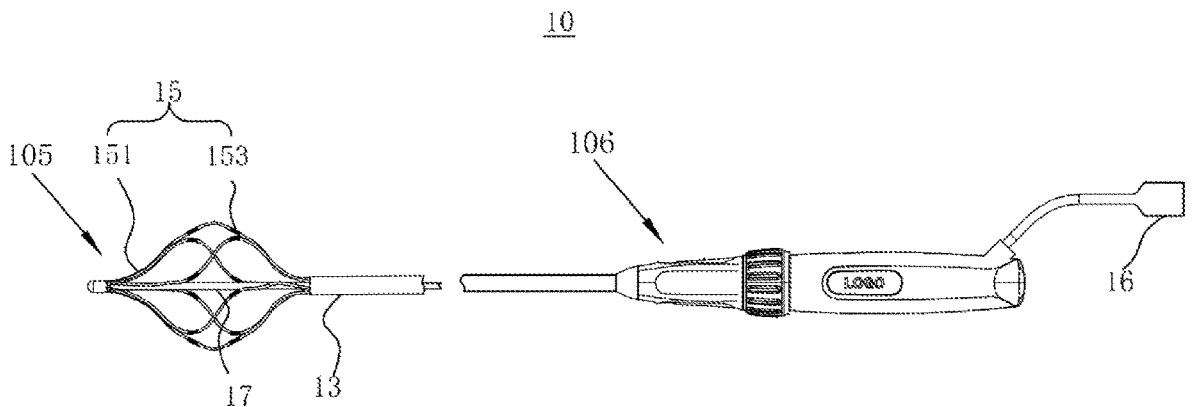
FIG. 1 is a side view of an ablation device according to the first embodiment of the present disclosure.

Referring to FIG. 1, a schematic view of an ablation device 10 according to the first embodiment of the present disclosure is shown. The ablation device 10 provided herein can be used to perform ablation and isolation on a target tissue area. The target tissue area may be located in the heart, including, but not limited to, pulmonary vein, or non PV Foci combined with typical atrial flutter such as left atrial appendage, superior vena cava, coronary sinus ostium, etc. It would be appreciated that the target tissue area is not necessarily limited to be located in the heart, but may be located in other tissues, which is not limited here.

Figure 2:
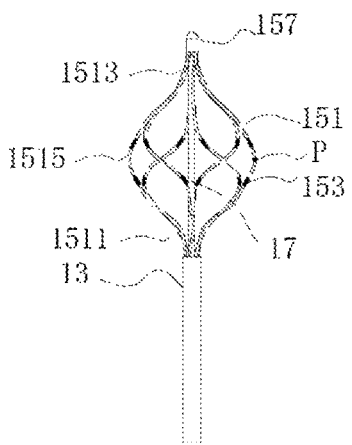
FIG. 2 is a partially enlarged schematic view of the ablation device shown in FIG. 1.
Figure 3:
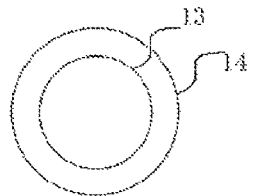
FIG. 3 schematically illustrates the outer tube and the sheath of the ablation device shown in FIG. 1.

Referring to FIGS. 1 to 3, the ablation device 10 includes an ablation catheter 105 and a handle 106. The ablation catheter 105 includes a sheath 13 and an ablation assembly 15, and the ablation assembly 15 is provided at the distal end of the sheath 13. The sheath 13 axially passes through the outer tube 14, and can be considered as an inner tube arranged within the outer tube 14. The proximal end of the sheath 13 is connected with the handle 106. When the ablation assembly 15 reaches the target tissue area by intervention, the ablation assembly 15 can be used to perform ablation and isolation on the target tissue area.

In one embodiment, the ablation assembly 15 is radially expandable. The radially expanded ablation assembly 15 can perform ring-like ablation and isolation on the tissue area (such as the ostium of the pulmonary vein), so as to prevent abnormal electrical propagation and/or disrupt abnormal electrical conduction through cardiac tissue, thereby treating cardiac arrhythmias and reducing the risk of many potentially lethal complications. The ablation assembly 15 can be radially expanded by various means. For example, the ablation assembly 15 can be self-expanded when moving out of the outer tube 14, or can be manually manipulated to radially expand after moving out of the outer tube 14. Here, the ablation assembly 15 includes a support frame 152 and an ablation element 153 provided on the support frame 152.

The ablation element 153 is used to provide ablation energy to perform ablation and isolation on the target tissue area. In some embodiments, the ablation element 153 can be an electrode, and the material of the electrode can be platinum, iridium, gold, silver and other medical metals that can be used for interventional therapy. In some other embodiments, part of the support frame 152 can be directly used as the ablation element 153. Specifically, the support frame 152 can be made of conductive metal material, a part of which is exposed and functions as the ablation element 153, and the other part is provided with an insulating layer, and when electrical signals flow through the support frame 152, the exposed part can perform ablation.

As a start, a support frame 152 being a self-expandable and shape memory stent, for example, the support frame 152 shown in FIGS. 1 to 3 being a cage-like self-expandable stent, will be explained below.

The support frame 152 includes a plurality of struts 151. The ablation element 153 is provided on the strut 151. In this embodiment, the ablation element 153 is an electrode. The distal ends of the struts 151 are joined together, and the proximal ends are connected to the distal end of the sheath 13. FIGS. 1 to 3 show that the strut 151 extends helically from the proximal end toward the distal end. Alternatively, in other embodiments, the strut 151 may not be in a helical shape, but may be a curved strut extending from the proximal end toward the distal end with a helix angle of zero, which will be described in detail in another embodiment below.

The support frame 152 can be switched between a compressed state and an expanded state. In the compressed state, the support frame 152 is movably accommodated in the outer tube 14. In the expanded state, the proximal end of the support frame 152 is exposed from the distal end of the outer tube 14, and each ablation element 153 is offset from the portion of the respective strut 151 with the maximum helix angle.

In the compressed state, the sheath 13 and the ablation assembly 15 are movably accommodated in the outer tube 14, and the ablation assembly 15 is constrained by the outer tube 14 and has a relatively small outer diameter, where the maximum outer diameter of the ablation assembly 15 in the compressed state is defined as a first outer diameter. In the expanded state, both the distal and proximal ends of the ablation assembly 15 are exposed (released) from the distal end of the outer tube 14 and the ablation assembly 15 expands outward into a generally cage-like configuration, where the ablation assembly 15 includes a section that protrudes outward away from the central axis thereof (i.e., in the radial direction), and the portions of the struts 151 of the ablation assembly 15 with the maximum helix angles protrude outward to the greatest extent with the maximum outer diameter which is defined as a second outer diameter. The first outer diameter is smaller than the second outer diameter. In the expanded state, each electrode 153 is offset from the portion of the respective strut 151 with the maximum helix angle.

Specifically, the strut 151 has a first point P. In the expanded state, the helix angle of the first point P is greater than the helix angles of other points of the strut 151. That is, the helix angle of the first point P of the strut 151 is the maximum helix angle of the strut 151, and the first point P corresponds to the portion of the ablation assembly 15 with the maximum radial dimension where the strut 151 is bent to the greatest extent. The points of the struts 151 other than the first points P have smaller helix angles than the first points P, and correspond to the portions of the ablation assembly 15 with smaller radial dimension where the struts 151 are bent to smaller extent. The ablation assembly 15 has the maximum outer diameter and radially protrudes to the greatest extent at the first points P.

Each strut 151 extends helically about the axis of the sheath 13. The axial dimensions of the struts 151 are variable and thus the radial dimensions of the points of the struts 151 with the maximum helix angles are also variable so that the outer diameter corresponding to the maximum helix angles of the struts 151 is also variable. Therefore, the axial dimension and the maximum radial dimension of the ablation assembly 15 are variable, so as to match the size of the target tissue area to be ablated. The electrode 153 is used to perform ablation on the target tissue to be ablated. When changing the axial dimensions of the struts 151, the first points P of the struts 151 with the maximum helix angles should correspond to the maximum outer diameter, so that the first points P or the curved sections between the first points P and the distal ends of the struts 151 can be fully used to perform ablation on the ostium or interior of the vascular tissue, improving the closeness to the target tissue to be ablated.

In the expanded state, before ablation, the axial dimension of the strut 151 can be changed by adjusting the distance between the proximal end and the distal end of the strut 151, so as to adjust the axial dimension and the outer diameter corresponding to the maximum helix angles of the ablation assembly 15 or the support frame 152, thereby fitting the maximum outer diameter of the ablation assembly 15, i.e., the radial dimensions corresponding to the maximum helix angles of the struts 151, and the electrode 153 for forming an electric field, with the target tissue to be ablated. Specifically, when the distance between the proximal end and the distal end of the strut 151 increases, the axial dimension of the strut 151 increases and thus the axial dimension of the ablation assembly 15 increases, while the maximum outer diameter of the ablation assembly 15 decreases. When the distance between the proximal end and the distal end of the strut 151 decreases, the axial dimension of the strut 151 decreases and thus the axial dimension of the ablation assembly 15 decreases, while the maximum outer diameter of the ablation assembly 15 increases.

Each strut 151 extends helically about the axis of the sheath 13 so that the ablation assembly 15 assumes a helical configuration. When entering the vascular tissue, such as pulmonary vein, the adjusted ablation assembly 15 may have an outer diameter mismatching with the opening diameter of the vascular tissue. For example, the opening diameter of the vascular tissue may be smaller than the maximum outer diameter of the ablation assembly 15. In such case, during the entry process, under the constraint of the pulmonary vein on the portions of the struts 151 with the maximum helix angles, the parts of the struts 151 protruding radially move toward the proximal side along the helical direction, causing the outer diameters and helix angles of the proximal parts of the struts 151 tend to increase. Since the proximal ends of the struts 151 are connected with the distal end of the sheath 13, with gradually decreasing outer diameters, the increasing trend of the outer diameters and helix angles of the proximal parts of the struts 151 can be slowed down. When the outer diameter of the adjusted ablation assembly 15 matches with the opening diameter of the vascular tissue, the increased outer diameter of the proximal part of the ablation assembly 15 would not exceed the opening diameter of the vascular tissue, so that the ablation assembly 15 entering the vascular tissue will encounter a small resistance at the portion with the maximum outer diameter (also the maximum helix angle) and the proximal part thereof, facilitating the smooth entry of the ablation assembly 15 into the vascular system. That is, the ablation assembly 15 has better compliance and can contact the target tissue area more closely, which is beneficial to improve the surgical effect.

The electrode 153 has a certain length extending along the length direction of the strut 151, and is provided on the helical strut 151. Particularly, the electrode 153 with a relatively high hardness and a long length will reduce the compliance of the portion of the strut 151 where the electrode 153 is provided. That is, the flexibility of the portion of the strut 151 where the electrode 153 is provided is relatively poor, and the electrode 153 will cause a certain resistance during the change of the outer diameter of the ablation assembly 15 and the struts 151. Here, in the expanded state of the ablation device 10, the electrode 153 is located on a portion of the strut 151 offset from the portion of the strut 151 with the maximum helix angle, the maximum outer diameter and the maximum bending degree, which is beneficial to reduce the resistance during the change of the outer diameter of the ablation assembly 15 and the struts 151. As the portion with the maximum helix angle is located at the radially outer edge of the ablation assembly 15, the electrode 153 being offset from the portion with the maximum helix angle facilitates reducing the resistance when it moves relative to the target tissue, and also can further improve the closeness and compliance of the ablation device 10 to the target tissue.

In this embodiment, the first point P is located at the middle point of the strut 151. The strut 151 includes a proximal section 1511, a distal section 1513, and a middle section 1515 located between the proximal section 1511 and the distal section 1513. The proximal section 1511 includes the most proximal end of strut 151. The distal section 1513 includes the most distal end of the strut 151. The first point P is the point half of the length of the strut 151 away from the most proximal end of the strut 151. In the expanded state, the helix angle of the most proximal end of the strut 151 and the helix angle of the most distal end of the strut 151 are smaller than the helix angle of the first point P of the strut 151. In the expanded state, the helix angles of the strut 151 are symmetric relative to the first point P, that is, the helix angles of the parts of the strut 151 located on two sides of the first point P are symmetric. The electrode 153 is offset from the first point P of the strut 151, that is, the electrode 153 is not provided at the first point P of the strut 151, so that the electrode 153 is offset from the portion of the strut 151 with the maximum bending degree in the expanded state of the ablation assembly 15.

It can be understood that the first point is not limited to the middle point of the strut 151, but can be other point of the strut by controlling the helix angles of the sections of the strut 151, such as the point one-third of the length of the strut 151 away from the most proximal end among others. In practice, the first point can be adjusted as required, and does not limit the scope of protection of the present invention.

In this embodiment, in the expanded state, the helix angle of the proximal section 1511 and the helix angle of the distal section 1513 are smaller than the helix angle of the middle section 1515. The helix angles of the sections of the strut 151 on two sides of the middle section 1515 are symmetric. Further, the helix angles of the sections of the strut 151 on two sides of the first point P are symmetric.

It should be noted that the helix angle of the proximal section 1511 and the helix angle of the distal section 1513 are not necessarily limited to be smaller than the helix angle of the middle section 1515, that is, the helix angles of the points of the strut 151 are not limited.

Taking the process of the ablation assembly 15 entering the pulmonary vein as an example, if the diameter of the pulmonary vein is relatively smaller than the outer diameter at the portion of the strut 151 with the maximum helix angle (also with the maximum outer diameter), under the constraint of the pulmonary vein on the portions of the struts 151 with the maximum outer diameters, the part of the strut 151 protruding radially move toward the proximal end of the strut 151 along the helical direction, causing the outer diameter of the proximal part of the strut 151 tend to increase, so that the pulmonary vein compresses the distal end of the strut 151. Since the ablation assembly 15 moves helically in the circumferential direction, the compression of the pulmonary vein causes the helix angles of the proximal parts of the struts 151 to increase, that is, the twist angles of the struts 151 in the circumferential direction increase. However, as the proximal ends of the struts 151 are connected with the distal end of the sheath 13, and the outer diameter of the proximal part of the ablation assembly 15 gradually decreases, the increasing trend of the outer diameters of the proximal parts of the struts 151 can be effectively slowed down, without causing the diameters of the proximal parts of the struts 151 to significantly exceed the diameter of the pulmonary vein, so that the ablation assembly 15 can smoothly enter the pulmonary vein and conform to the anatomical structure of the target tissue area. Further, the radial support force of the ablation assembly 15 is improved and thus the ablation assembly 15 can contact the target tissue area more closely, which is beneficial to improve the surgical effect.

The first points P of all struts 151 are located at the same axial level of the support frame 152, and are distributed at intervals in the same plane perpendicular to the axial direction of the sheath 13, that is, the geometric shape formed by the first points P of all struts 151 in the same plane perpendicular to the axial direction of the sheath 13 is discrete. The geometric shape formed by connecting the first points P of all struts 151 sequentially is a symmetrical figure, for example, a circle, an ellipse, a semicircle or any other nonlinear geometric shape, which is not limited herein. The number of struts 151 is not limited here. For example, the number of struts 151 can be in the range of 4 to 10. In this embodiment, the first points of the struts 151 are evenly distributed in the same plane perpendicular to the axial direction of the sheath 13. The diameter of the portion of the ablation assembly 15 protruding to the greatest extent in a natural state ranges from 6 to 25 mm. It should be noted that the first points of the struts 151 are not necessarily limited to be evenly distributed in the same plane perpendicular to the axial direction of the sheath 13 and the range of the diameter of the portion of the ablation assembly 15 protruding to the greatest extent in the natural state is not limited.

In this embodiment, the proximal ends of the struts 151 are fixedly accommodated in the distal end of the sheath 13.

The twist angle of the most proximal end of each strut 151 in the circumferential direction of the sheath 13 relative to the most distal end of the same strut 151 ranges from 30 degrees to 70 degrees. In other embodiments, the twist angle can be within the range of 0-540 degrees.

The ablation device 10 further includes a connector 16 connected with the handle 106. The connector 16 is electrically connected with the electrodes 153. The connector 16 is used to connect to a pulse signal source, and transmits pulse signals to the electrodes 153 for the electrodes 153 to perform ablation on the target tissue area. It should be noted that the electrodes 153 can be used for unipolar ablation or bipolar ablation. In case of unipolar ablation, the electrodes 153 on the support frame 152 can be configured as the positive electrodes, and the negative electrode can be disposed outside the body, close to the positive electrodes and in contact with human skin. In the case of bipolar ablation, the electrodes 153 on the support frame 152 can be configured as positive and negative electrodes which can be alternatively spaced from each other, and the specific arrangement is not limited here. It can be understood that the connector 16 can be connected with a non-pulse signal source. For example, the connector 16 can be connected with a radio frequency energy for radio frequency ablation, or other energy forms. Alternatively, the electrodes 153 can perform hybrid ablation using pulse and radio frequency.

The ablation device 10 further includes a guide rod 17 which movably passes through the sheath 13. The sheath 13 is a hollow tube, and the proximal end of the guide rod 17 is connected with the handle 106. The distal end of the guide rod 17 is connected to the distal ends of the struts 151. Each strut 151 extends helically around the guide rod 17. The handle 106 is used to pull the guide rod 17 to adjust the axial length and outer diameter of the ablation assembly 15. In this embodiment, the guide rod 17 extends in the axial direction of the sheath 13, and the axis of the ablation assembly 15 extends in the same direction as the extension direction of the guide rod 17. The guide rod 17 may be a steel cable, a hollow flexible polyimide (PI) tube, a fluorinated polyethylene (PDFE) tube, a stainless steel tube, or a tube made of other polymer materials. Alternatively, the ablation assembly 15 may be non-adjustable in the radial direction, in which case the guide rod 17 can be removed. Further alternatively, the electrodes 153 can be provided on both the support frame 152 and the guide rod 17 inside the support frame 152, and the electrodes on the support frame 152 and the guide rod 17 are respectively configured as positive and negative electrodes. In this way, when pulse energy is applied, a pulse electric field for tissue ablation can be generated between the positive electrodes and the negative electrodes.

The ablation device 10 adjusts the outer diameter of the ablation assembly 15 by controlling the guide rod 17 through the handle 106 to pull the struts 151 of the ablation assembly 15. When the guide rod 17 moves from the distal end toward the proximal end relative to the sheath 13, the outer diameter of the ablation assembly 15 increases, and when the guide rod 17 moves from the proximal end toward the distal end relative to the sheath 13, the outer diameter of the ablation assembly 15 decreases. The outer diameter of the ablation assembly 15 can be flexibly adjusted by the guide rod 17, so that the ablation assembly 15 can adapt to blood vessel (such as pulmonary vein) or other body tissues with various diameters, and can perform ablation on the target area to be ablated with any appropriate outer diameter. The ablation assembly 15 is not necessarily limited to be compressed to the maximum extent in the axial direction to perform ablation, which improves the adaptability of the ablation assembly 15 to the anatomical structure of various target areas to be ablated, facilitating the operation of the ablation device 10, with a good ablation effect. For example, in operation of the ablation device 10, the outer diameter of the ablation assembly 15 can be increased so that the electrodes 153 can generate an electric field by transmitting pulse energy at the ostium of the pulmonary vein to perform ablation on the tissue, or the outer diameter of the ablation assembly 15 can be decreased so that the electrodes 153 can be placed within the pulmonary vein to perform ablation on the tissue.

Figure 4:
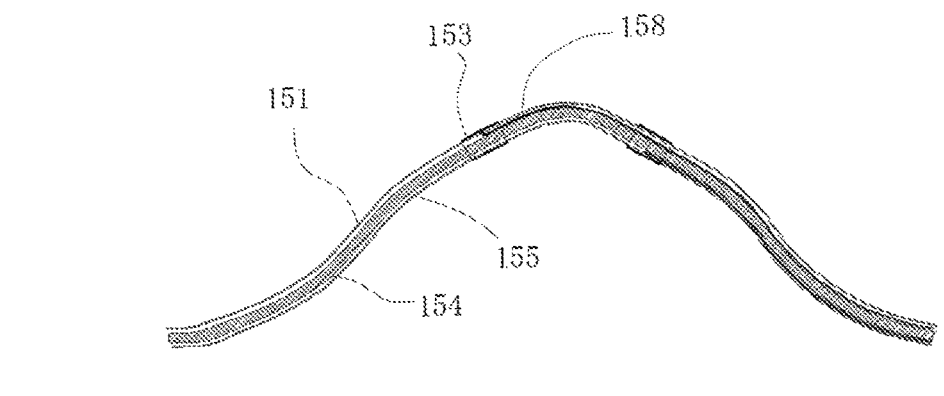
FIG. 4 is a cross-sectional view of a strut and an ablation element of the ablation device in FIG. 2.
Figure 4A:
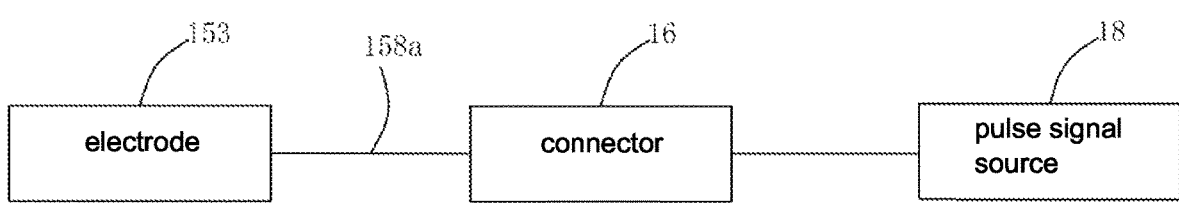
FIG. 4a is a schematic view showing a circuit connection relationship of an electrode of the ablation device in FIG. 4.
Figure 4B:
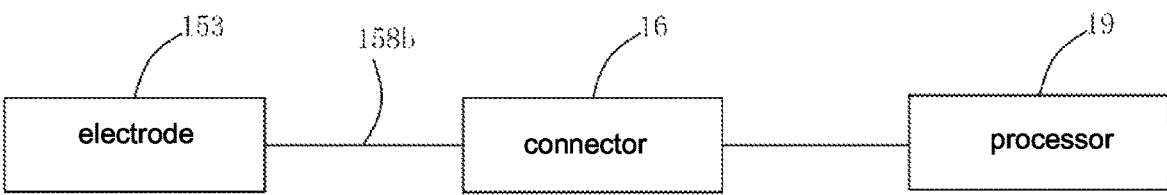
FIG. 4b is a schematic view showing a circuit connection relationship of another electrode of the ablation device in FIG. 4.

Referring to FIG. 4, the strut 151 includes a strut body 154 and an insulating sleeve 155, and the insulating sleeve 155 surrounds the strut body 154. The cross-sectional shape of the strut body 154 may be circular, semicircular or other shapes, which is not limited herein. In this embodiment, the strut body 154 is made of nickel-titanium wire, so that the strut body 154 has excellent flexibility and strength and can contact the target tissue closely. It would be appreciated that the strut body 154 may be made of other materials, such as stainless steel, or polymer materials. The electrode 153 is fixed on the outer wall of the insulating sleeve 155. In this embodiment, the insulating sleeve 155 is made of Pebax or heat shrinkable tube (such as FEP heat shrinkable tube) or other insulating polymer materials, which ensures the insulation between the electrode 153 and the strut body 154. The insulating sleeve 155 can include one layer or multiple layers, which is not limited here.

The electrode 153 can be fixed on the outer wall of the insulating sleeve 155 by curing glue. The electrode 153 is made of platinum-iridium alloy or gold or other platinum alloys, and the shape of the electrode 153 conforms to the shape of the strut 151. Each strut 151 is provided with one, two or more electrodes 153. The electrodes 153 on the same strut 151 have the same polarity and the polarity of the electrodes 153 on the strut 151 is opposite to the polarity of the electrodes 153 on the adjacent strut 151. The electrodes 153 can be configured with single-phase or biphasic pulses with different parameters such as voltage, pulse width, repetition frequency, duty cycle, and number of pulses. The electrodes 153 can be used for cardiac electrophysiological signal mapping, and/or other functions such as cardiac pacing. For example, in one period, all electrodes 153 can be used for ablation, and in another period, all electrodes 153 can be used for mapping. Alternatively, some electrodes 153 are always used for ablation, and some other electrodes 153 are always used for mapping.

Herein, independent addressing control can be performed on each electrode 153, that is, electric pulse signals, radio frequency signals or other signals can be output to any electrode as required to perform ablation on the target tissue area.

In this embodiment, each strut 151 is provided with two electrodes 153 as shown in FIG. 2 and FIG. 4, and the two electrodes 153 are respectively located on two sides of the first point and are asymmetrical, that is, one electrode 153 is located on the proximal side of the first point, and the other electrode 153 is located on the distal side of the first point. In the expanded state, the electrodes 153 on the distal side of the struts 151 form a first ring for generating a first electric field, the electrodes 153 on the proximal side of the struts 151 form a second ring for generating a second electric field. The diameter of the first ring is smaller than that of the second ring. Correspondingly, the diameter of the first electric field is smaller than that of the second electric field. In one control mode, depending on the size of the target tissue area, the electrodes 153 in the first ring can be selected and controlled for ablation alone, or the electrodes 153 in the second ring can be selected and controlled for ablation alone, or the electrodes 153 both in the first ring and the second ring can be selected and controlled for ablation.

Figure 5:
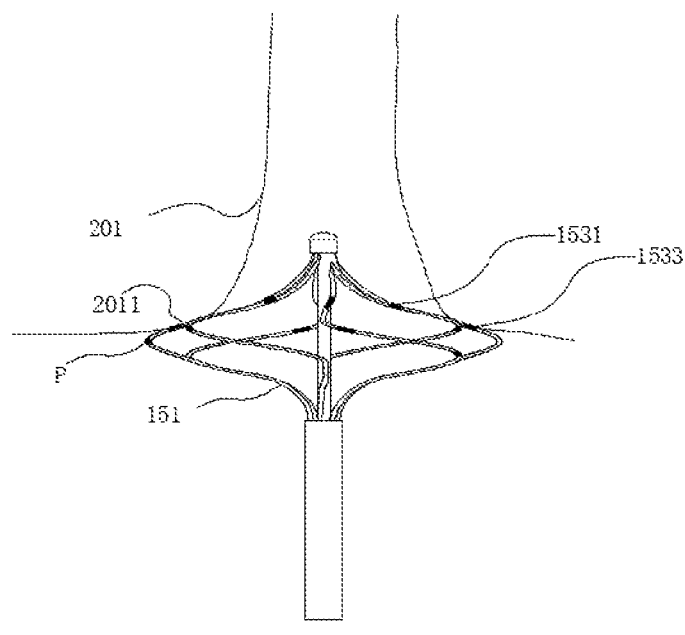
FIG. 5 shows an application scene of an ablation catheter according to an embodiment of the present disclosure.

Referring to FIG. 5, an application scene of the ablation assembly of the ablation device according to an embodiment of the present disclosure for performing ablation on the ostium of the pulmonary vein (not in the pulmonary vein) is shown. The arrangement of the electrodes in the embodiment shown in FIG. 5 is different from that in the previous embodiments. The two electrodes on each strut 151 are arranged on the distal side of the first point P of the respective strut 151. The ostium 2011 of the pulmonary vein 201 shown in FIG. 5 is relatively large. The electrode ring on the struts 151 consisting of electrodes 153 closer to the distal ends of the struts 151 is called a distal electrode ring 1531, and the electrode ring on the struts 151 consisting of electrodes 153 closer to the proximal ends of the struts 151 is called a proximal electrode ring 1533. The distal electrode ring 1531 is further away from the ostium 2011, while the proximal electrode ring 1533 is relatively closer to the ostium 2011 so that it can fit the ostium 2011 better. Therefore, the proximal electrode ring 1533 can be controlled for ablation, the distal electrode ring 1531 can be powered off or controlled for mapping. If the opening diameter of the ostium 2011 of the pulmonary vein 201 is small, the distal electrode ring 1531 can be configured for ablation.

In the application scenario of internal pulmonary vein ablation, two electrode rings can be selectively used as required. Referring to FIG. 1, FIG. 2, FIG. 4, FIGS. 4*a* and 4*b*, the ablation device 10 further includes a conducting wire 158 which passes through the interior of the sheath 13 and the interior of the insulating sleeve 155. The proximal end of the conducting wire 158 is connected to the connector 16, and the distal end of the conducting wire 158 is electrically connected to the electrode 153. The conducting wire 158 and the strut body 154 are insulated from each other. The electrode 153 and the conducting wire 158 are connected by welding or other means.

The conducting wire 158 includes a first conducting wire 158*a* connected to the external pulse signal source 18 through the connector 16, and the electrode 153 connected to the first conducting wire 158*a* uses the pulse energy from the pulse signal source 18 to perform ablation on the target tissue area; and/or the conducting wire 158 includes a second conducting wire 158*b*, the electrode 153 connected to the second conducting wire 158*b* is used to collect the electrophysiological signals in the target tissue area to generate an electrocardiogram, etc., and the second conducting wire 158*b* transmits the collected electrophysiological signals through the connector 16 to the external processor 19, which is beneficial to the positioning to the complex cardiac anatomical structure, improving the operation efficiency and reducing the radiation to the operator and the patient, and also allows the progress of the ablation operation to be monitored, fully controlling the ablation process and improving the safety of surgery. It should be noted that the second conducting wire and the mapping electrode used for electrophysiological signal mapping can be considered as forming a mapping device.

It can be understood that the ablation device 10 herein can be connected to an external radio frequency source or other energy delivery devices through the connector 16.

In this embodiment, the voltage of the pulse signals received by the electrode 153 is in the range of 900V to 2400V, including all values and sub-ranges within the range. The pulse frequency is in the range of 1 kHz to 500 kHz, including all values and sub-ranges within the range. The pulse signal source can be a unipolar, high-voltage pulse power supply or a bipolar, high-voltage pulse power supply. In each cycle of the bipolar, high-voltage pulse signal waveform, the positive and negative pulses alternate. Correspondingly, the maximum voltage that the conducting wire can bear is 3000V. All electrodes 153 can be divided into one or more positive-negative sets.

Referring to FIG. 2 again, the ablation assembly 15 further includes an installation sleeve 157. The distal end of the guide rod 17 is fixed in the installation sleeve 157. The distal ends of the struts 151 are fixed in the installation sleeve 157, so that the distal ends of the struts 151 are joined together. In this embodiment, the distal ends of the struts 151 extend into the installation sleeve 157 from the proximal end of the installation sleeve 157. The distal ends of the struts 151 are joined together through the installation sleeve 157, thereby improving the connection strength of the distal ends of the struts 151. The distal end of the installation sleeve 157 has a rounded structure, which is beneficial to reduce damage to the target tissue, and also allows the ablation assembly 15 to conform to the target tissue area (such as the left atrial appendage).

Figure 6:
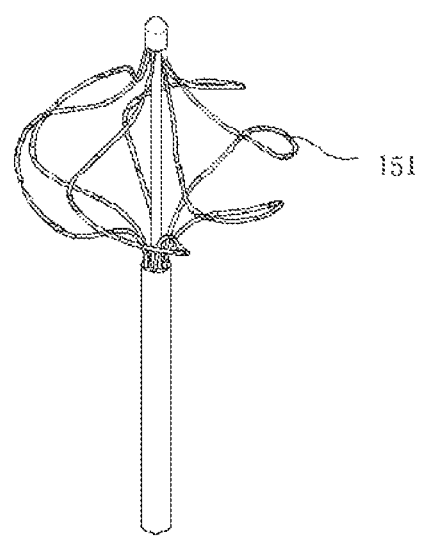
FIG. 6 is a schematic view of an ablation catheter according to another embodiment of the present disclosure.
Figure 7:
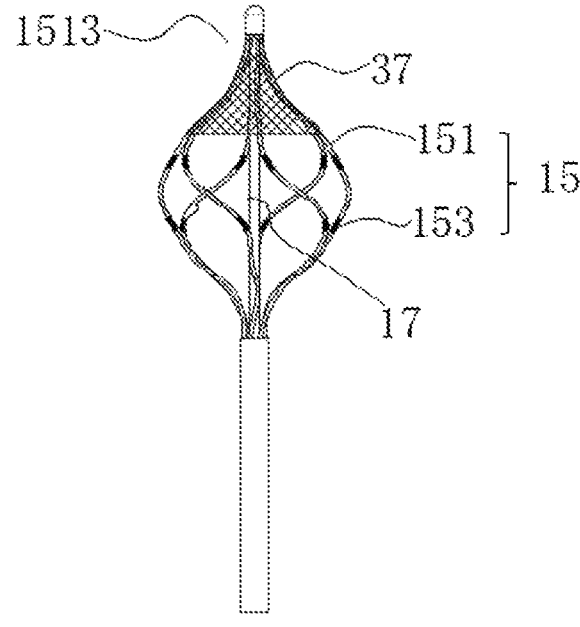
FIG. 7 is a schematic view of an ablation catheter according to another embodiment of the present disclosure.

It should be noted that the helix angles of the strut 151 on the two sides of the first point P are not necessarily limited to be symmetric to each other; and the helical forms of all the struts 151 are not necessarily limited to be the same. In the embodiment shown in FIG. 6, at least one strut 151 has a helical form different from other struts 151, and the helix angles of some strut 151 are respectively asymmetric relative to the first point P. Referring to FIG. 7, the ablation device 10 according to another embodiment of the present disclosure is similar to the ablation device 10 according to the above-mentioned first embodiment, the similarities therebetween will not be repeated here, and the difference therebetween is that the ablation device 10 further includes an elastic support structure 37. The elastic support structure 37 is connected between two adjacent struts 151, and used to keep a spacing between the two adjacent struts 151 to prevent the electrodes 153 from generating arcs or electric sparks due to too small distance between the struts 151 during the operation of the ablation device 30, causing breakdown damage to the target tissue. In this embodiment, the elastic support structure 37 is a mesh structure, and the elastic support structure 37 is arranged in the circumferential direction of the ablation assembly 15. The elastic support structure 37 covers the distal sections 1513 of the struts 151. The elastic support structure 37 is connected with all struts 151. The shape of the elastic support structure 37 can vary with the outer diameter of the ablation assembly 15. In this embodiment, the elastic support structure 37 is made of nickel-titanium wire, and thus has excellent flexibility and high strength.

Figure 8:
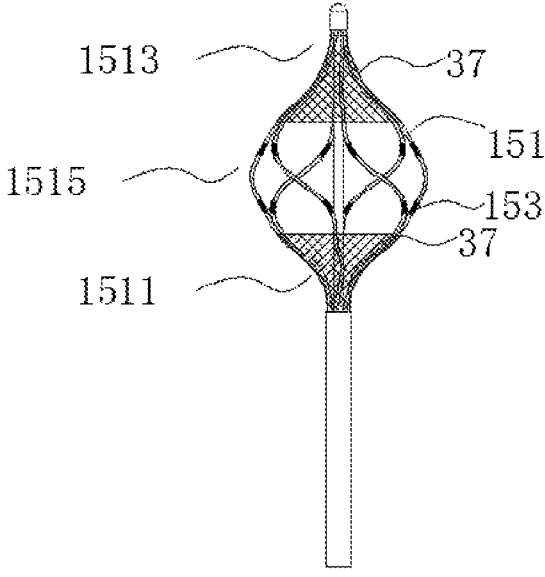
FIG. 8 is a schematic view of an ablation catheter according to a further embodiment of the present disclosure.
Figure 9:
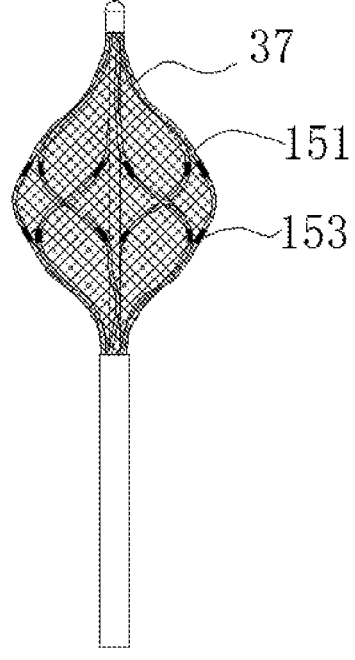
FIG. 9 is a schematic view of an ablation catheter according to a further embodiment of the present disclosure.

It should be noted that the number of elastic support structures 37 is not limited. As shown in FIG. 8, two elastic support structures 37 are provided, with one covering the proximal sections 1511, and the other covering the distal sections 1513. The elastic support structure 37 can cover all sections of the struts 151 of the ablation assembly 15 (i.e., the proximal sections 1511, the distal sections 1513 and the middle sections 1515), as shown in FIG. 9. In short, the elastic support structure 37 covers at least one of the proximal sections 1511, the distal sections 1513 and the middle sections 1513 of the struts 151.

It can be understood that the elastic support structure 37 can be other support members, such as a support strip/rod arranged between adjacent struts 151, and a component provided on the struts 151 for isolating electrodes.

It can be understood that the elastic support structure 37 can be provided on at least one of the proximal end of the ablation assembly 15, the distal end of the ablation assembly 15, and the middle part of the ablation assembly 15 between the proximal end and the distal end of the ablation assembly 15.

Figure 10:
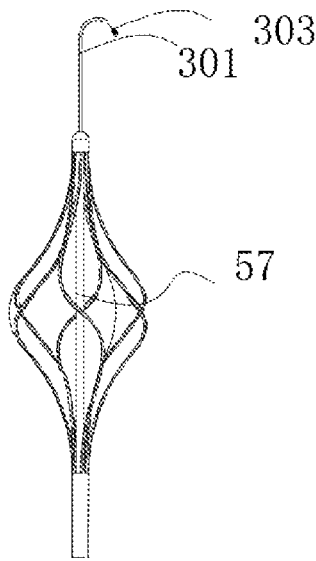
FIG. 10 is a schematic view of an ablation catheter according to a further embodiment of the present disclosure.

Referring to FIG. 10, the ablation device according to another embodiment of the present disclosure is substantially the same as the ablation device according to the first embodiment, and the similarities therebetween will not be repeated here. The guide rod 57 is provided with a guide channel (not shown) in the axial direction, and the guide channel is used for the guide wire 301 passing through. The mapping electrode 303 at the distal end of the guide wire 301 can be exposed from the most distal end of the guide rod 57 for electrophysiological signal mapping. The guide wire 301 and the mapping electrode 303 form a mapping device, and the mapping device and the ablation device form an ablation system. The guide channel specially provided for the mapping electrode 303 for electrophysiological signal mapping facilitates the use and control of the ablation device.

Figure 11:
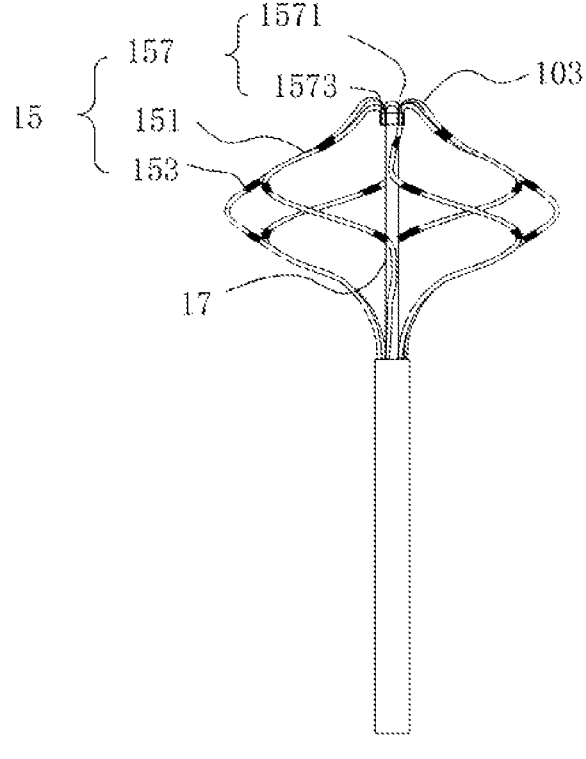
FIG. 11 is a schematic view of an ablation catheter according to another embodiment of the present disclosure.
Figure 12:
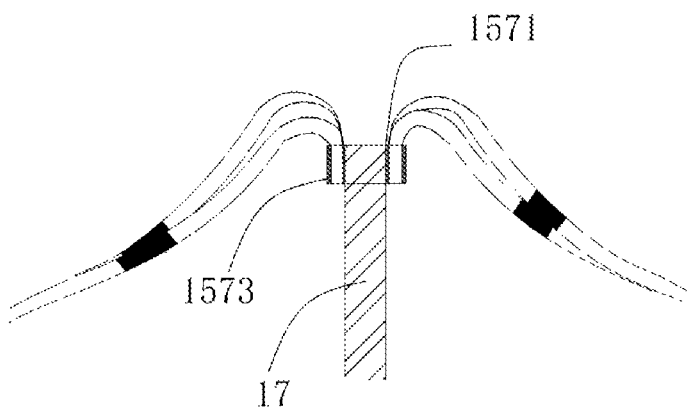
FIG. 12 is a schematic cross-sectional view of the distal end of the ablation assembly and the installation sleeve shown in FIG. 11.

Referring to FIG. 11 and FIG. 12, the ablation device according to another embodiment of the present disclosure is substantially the same as that of the ablation device according to the first embodiment, the similarities therebetween will not be repeated here, and the difference therebetween is that the distal ends of the struts 151 extend from the distal end of the installation sleeve 157 into the installation sleeve 157, that is, the distal ends of the struts 151 are converged toward the proximal side.

The installation sleeve 157 includes an inner sleeve 1571 and an outer sleeve 1573. The inner sleeve 1571 is fixed on and surrounds the distal end of the guide rod 17, the outer sleeve 1573 surrounds the inner sleeve 1571, and the distal ends of the struts 151 are fixedly sandwiched between the inner sleeve 1571 and the outer sleeve 1573. It can be understood that the distal ends of the struts 151 are not necessarily limited to be fixed by the installation sleeve 157, but can be joined together by other means. For example, the distal ends of all the struts 151 can be directly joined together by curing glue.

The distal end of the strut 151 extends from the distal end of the installation sleeve 157 into the installation sleeve 157 to form a smooth turn-up structure 103. The turn-up structure 103 can effectively reduce the mechanical damage of the ablation assembly 15 to the target tissue, and better conform to the target tissue.

Figure 13:
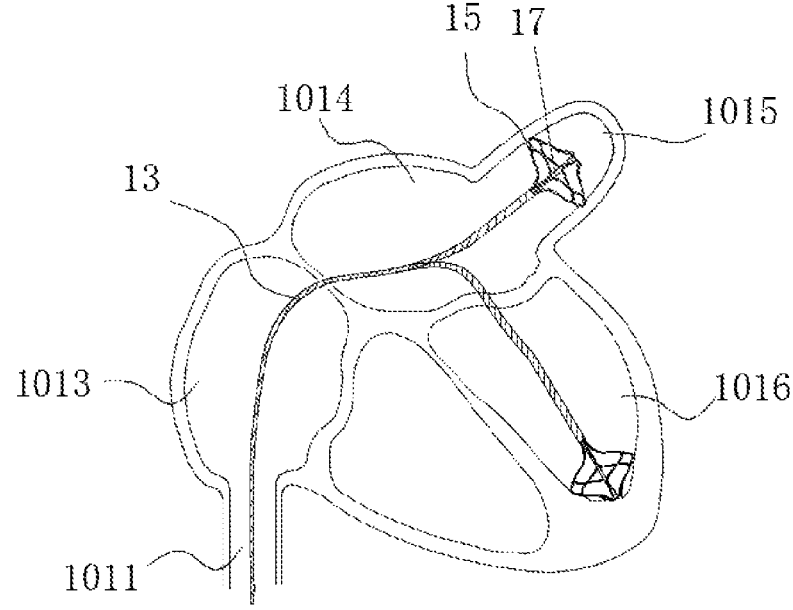
FIG. 13 shows an application scene of the ablation catheter shown in FIG. 11 performing ablation on a patient with myocardial hypertrophy.

Referring to FIG. 13, a schematic view of an application scenario of the ablation device according to the above embodiment to perform ablation on a patient with myocardial hypertrophy is shown. Taking the left atrial appendage 1015 as the target tissue, the ablation assembly 15 enters the right atrium 1013 from the inferior vena cava 1011 of the heart along with the distal end of the sheath 13, and then enters the left atrial appendage 1015 through the left atrium 1014. The guide rod 17 is controlled by the handle 106, and the outer diameter of the ablation assembly 15 is adjusted to fit the size of the lumen of the left atrial appendage 1015. The electrodes 153 are powered on to generate an electric field to perform ablation on the left atrial appendage 1015.

Taking the bottom of the left ventricle 1016 away from the left atrium 1011 as the target tissue, the ablation assembly 15 enters the right atrium 1013 from the inferior vena cava 1011 of the heart along with the distal end of the sheath 13, and then enters the left ventricle 1016 through the left atrium 1014. The guide rod 17 is controlled by the handle 106, and the outer diameter of the ablation assembly 15 is adjusted to fit the size of the lumen at the bottom of the left ventricle 1016 away from the left atrium 1011. The electrodes 153 are powered on to generate an electric field to perform ablation on the lumen at the bottom of the left ventricle 1016 away from the left atrium 1011.

Referring to FIGS. 14 to 17, the support frame 21 with the cage-like self-expandable stent may have the following configurations. It should be noted that, in this embodiment, in order to distinguish from the above-mentioned cage-like self-expandable stents, the reference signs of the ablation assembly, the support frame, and the electrode in this embodiment have been changed to 20, 21 and 25, respectively.

The support frame 21 includes a positioning frame 22 and a bearing frame 24. The positioning frame 22 is distal to the bearing frame 24. The distal end of the sheath 52 is connected with the proximal end of the bearing frame 24, the distal end of the guide rod 54 is connected with the positioning frame 22, and the proximal end of the positioning frame 22 is connected with the distal end of the bearing frame 24. The sheath 52 and the guide rod 54 together form an adjustment assembly 50. During the axial movement of the guide rod 54 relative to the sheath 52, the support frame 21 is deformed, and the deformation ratio of the positioning frame 22 is smaller than that of the bearing frame 24. In other embodiments, the support frame 21 may not include the positioning frame 22, and the distal end of the bearing frame 24 converges directly or indirectly to the distal end of the guide rod 54.

The deformation ratio refers to the ratio of the dimension of the frame in the fully released state minus the deformed dimension to the dimension in the fully released state. For example, in the axial direction, provided that the dimension of the frame in the fully released state is L1, the dimension of the deformed frame is L2, and the deformation ratio is defined as A, then $A=(L1-L2)/L1$.

Specifically, in the axial direction, provided that the dimension of the positioning frame 22 in the fully released state is M1, the dimension of the deformed positioning frame 22 is M2, and the deformation ratio is defined as A1, then $A1=(M1-M2)/M1$.

Specifically, in the axial direction, provided that the dimension of the bearing frame 24 in the fully released state is N1, the dimension of the deformed bearing frame 24 is N2, and the deformation ratio is defined as A2, then $A2=(N1-N2)/N1$.

The deformation ratio of the positioning frame 22 is smaller than the deformation ratio of the bearing frame 24, i.e., $A1<A2$.

In this embodiment, when the support frame 21 is fully released, the positioning frame 22 and the bearing frame 24 are both frames with inner cavities, and both the radial and axial dimensions of the positioning frame 22 are smaller than the radial and axial dimensions of the bearing frame 24. In a modified embodiment, the radial dimension and/or the axial dimension of the positioning frame 22 can be greater than or equal to the radial dimension and the axial dimension of the bearing frame 24.

The support frame 21 has at least one of a mesh structure, a rod structure or a frame structure. The support frame 21 can be made by cutting a flexible metal tube, or by braiding elastic metal wires, or by partially braiding and partially cutting a tube with the different processed parts being fixed to each other by welding or connector. The material of the tube is metal or non-metal material, preferably shape memory metal material, more preferably nickel-titanium alloy material. In this embodiment, the support frame 21 is formed by cutting and shaping a nickel-titanium alloy tube, and the cross-section of a strut for forming the positioning frame 22 is the same as that of a strut for forming the bearing frame 24. When the inner tube 54 moves relative to the outer tube 52, the deformation ratio of the struts of the positioning frame 22 is smaller than that of the bearing frame 24. That is, under the same axial force, it is more difficult for the positioning frame 22 to deform axially and radially.

Specifically, during the deformation of the support frame 21, the axial and radial deformation ratios of the positioning frame 22 are both smaller than the axial and radial deformation ratios of the bearing frame 24.

Figure 15:
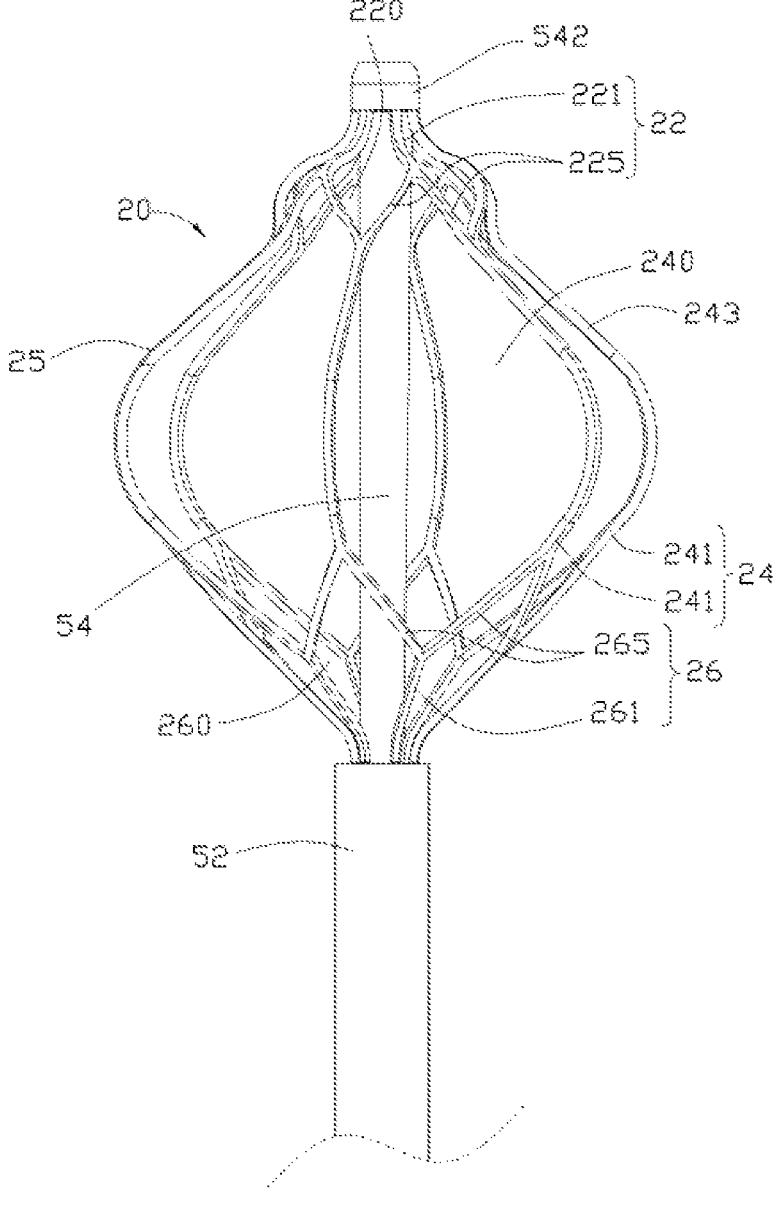
FIG. 15 is a schematic view of the ablation catheter in FIG. 14.
Figure 16:
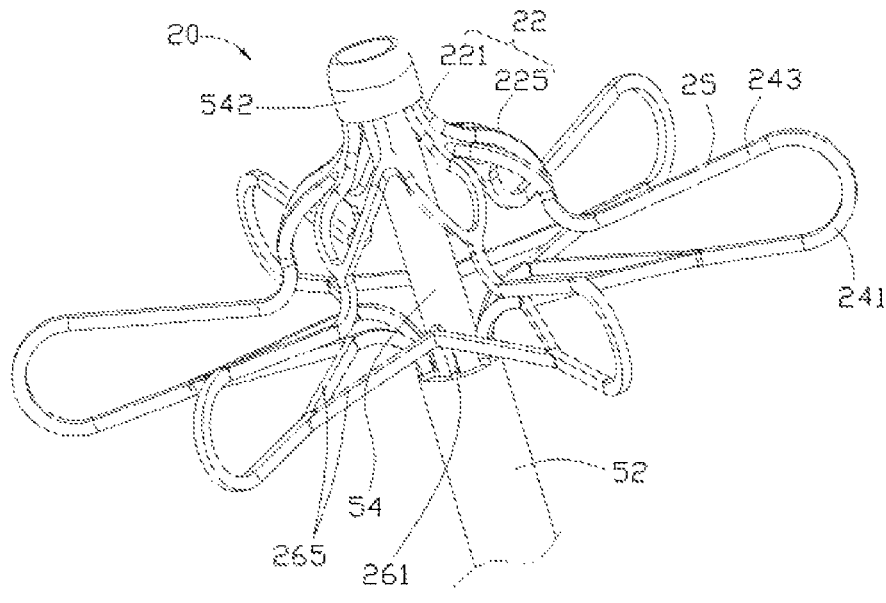
FIG. 16 is a schematic view of the ablation catheter in FIG. 15 in another state.
Figure 17:
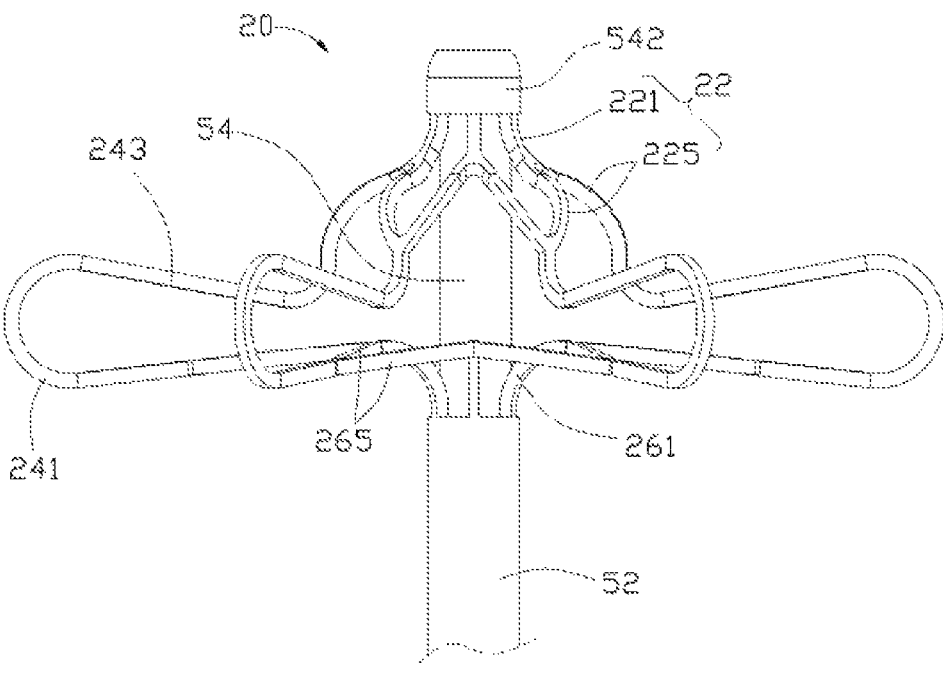
FIG. 17 is a front view of the ablation catheter in FIG. 16.

As shown in FIGS. 15 to 17, optionally, both the positioning frame 22 and the bearing frame 24 are mesh structures. The positioning frame 22 defines meshes 220, the bearing frame 24 defines meshes 240, and the opening area of the mesh 220 of the positioning frame 22 is smaller than the opening area of the mesh 240 of the bearing frame 24. The adjacent struts of the mesh of the positioning frame 22 are connected to each other, so that the positioning frame 24 is not easily deformed. In this embodiment, the cross-section of the strut of the positioning frame 22 is the same as that of the strut of the bearing frame 24, and the area of the mesh 220 is smaller than the area of the mesh 240. For example, in this embodiment, both the mesh 220 and the mesh 240 are long and narrow, and in the fully released state, the opening area of the mesh 220 is smaller than that of the mesh 240. Since the mesh of the bearing frame 24 is relatively larger than the mesh of the positioning frame 22, during the relative movement between the sheath 52 and the guide rod 54, the bearing frame 24 is easier to deform than the positioning frame 22 so as to get close to the target tissue area. The mesh of the positioning frame 22 is small and the struts of the positioning frame 22 are connected and limited to each other, so that the deformation ratio of the positioning frame 22 is relatively small and the positioning frame 22 tends to maintain its initial profile more easily than the bearing frame 24, with better alignment, which means that when the ablation assembly 20 is positioned at the ostium of the pulmonary vein, the axis of the positioning frame 22 can be more easily aligned with the center of the pulmonary vein. Therefore, the situation that when adjusting the diameter of the bearing frame 24, the positioning frame 22 is greatly deformed and cannot be pressed against the inner wall of the pulmonary vein so that the ablation assembly 20 cannot be aligned around the ostium of the pulmonary vein can be avoided. Further, the deformation ratio of the positioning frame 22 is small, and the positioning frame 22 protrudes axially from the bearing frame 24, so that the ablation assembly 20 can easily enter the pulmonary vein, to allow the bearing frame 24 to be positioned around the ostium of the pulmonary vein.

In other embodiments, the cross section of the strut for forming the positioning frame 22 is greater than the cross section of the strut for forming the bearing frame 24. That is, compared with the bearing frame 24, the cross section of a single strut of the positioning frame 22 is at least larger in a certain direction. Compared with the bearing frame 24, the diameter of a single strut of the positioning frame 22 is greater, and the opening area of the mesh of the positioning frame 22 is not larger than the opening area of the mesh of the bearing frame 24, so that the deformation ratio of the positioning frame 22 is smaller than the deformation ratio of the bearing frame 24 during the deformation of the support frame 21.

In other embodiments, the rigidity of the strut of the positioning frame 22 is greater than or equal to the rigidity of the strut of the bearing frame 24, so that during the deformation of the support frame 21, the positioning frame 22 is less likely to elastically deform than the bearing frame 24.

In other embodiments, the positioning frame 22 and the bearing frame 24 are formed by wires. The wire diameter of the positioning frame 22 is greater than or equal to that of the bearing frame 24, and the opening area of the mesh of the positioning frame 22 is smaller than or equal to the opening area of the mesh of the bearing frame 24, so that the deformation ratio of the positioning frame 22 is smaller than that of the bearing frame 24 during the deformation of the support frame 21.

Further, the rigidity of the wire of the positioning frame 22 is greater than or equal to the rigidity of the wire of the bearing frame 24, so that the deformation ratio of the positioning frame 22 is smaller than that of the bearing frame 24 during the deformation of the support frame 21.

Optionally, both the sheath 52 and the guide rod 54 are hollow tubular, and the guide rod 54 is disposed in the sheath 52 so that the guide rod 54 is movably inserted in the lumen of the sheath 52. When the guide rod 54 moves axially relative to the sheath 52, the axial dimension and radial dimension of the support frame 21 change. Specifically, when the guide rod 54 moves axially toward the proximal side relative to the sheath 52, the axial dimension of the bearing frame 24 decreases and the radial dimension increases; when the guide rod 54 moves axially toward the distal side relative to the sheath 52, the axial dimension of the bearing frame 24 increases and the radial dimension decreases.

In other embodiments, the guide rod 54 is rotatable relative to the sheath 52, so that the wire or strut of the bearing frame 24 can be deformed into a helical form.

As shown in FIG. 15, specifically, the positioning frame 22 includes a plurality of first primary struts 221 and a plurality of first secondary struts 225 from the distal end to the proximal end. The plurality of first primary struts 221 are arranged in the circumferential direction of the guide rod 54. The distal end of each first primary strut 221 is connected to the guide rod 54, and the proximal end of each first primary strut 221 is connected to corresponding first secondary struts 225. The bearing frame 24 includes a plurality of bearing struts 241 arranged in the circumferential direction of the guide rod 54. The distal end of each bearing strut 241 is connected to corresponding first secondary struts 225. The first secondary struts 225 connected to the same bearing strut 241 are connected to different first primary struts 221.

The positioning frame 22 is a mesh structure provided at the distal end of the bearing frame 24. The bearing frame 24 is also a mesh structure provided at the proximal end of the positioning frame 22. The positioning frame 22 is configured to be inserted into the pulmonary vein during the ablation for guiding and positioning, to allow the bearing frame 24 to provide a closed-loop ablation area at the ostium of the pulmonary vein, improving the accuracy of ablation and the success rate of the operation.

In this embodiment, the positioning frame 22 and the bearing frame 24 are formed in one piece by cutting a nickel-titanium tube. The positioning frame 22 includes six first primary struts 221 and a plurality of first secondary struts 225 respectively connected to the proximal ends of the six first primary struts 221. The proximal end of the first primary strut 221 is connected with two first secondary struts 225. The plurality of first primary struts 221 are distributed in the circumferential direction of the guide rod 54. Preferably, these first primary struts 221 are evenly distributed in the circumferential direction of the guide rod 54. The bearing frame 24 includes six bearing struts 241, and these bearing struts 241 are distributed in the circumferential direction of the guide rod 54. Preferably, these bearing struts 241 are evenly distributed in the circumferential direction of the guide rod 54. The distal end of each primary strut 221 is connected to the distal end of the guide rod 54, and the bearing strut 241 is connected with the proximal end of the first primary strut 221 through the first secondary strut 225. Specifically, the proximal end of each primary strut 221 is connected with two first secondary struts 225, and the distal end of each bearing strut 241 is connected with two first secondary struts 225. The distal ends of the two first secondary struts 225 connected to the distal end of the same bearing strut 241 are connected to different first primary struts 221 respectively.

When the support frame 21 is fully released, the radial dimension of the frame formed by the plurality of first primary struts 221 and the plurality of first secondary struts 225 is smaller than the radial dimension of the frame formed by the plurality of bearing struts 241. The bearing strut 241 is provided with an ablation element 25. Specifically, the ablation element 25 is an electrode. At least one bearing strut 241 of the bearing frame 24 is provided with an electrode. Specifically, it may be one of the bearing struts 241 of the bearing frame 24 that is provided with an electrode, or each bearing strut 241 may be provided with an electrode, or some bearing strut 241 at intervals or adjacent to each other may be provided with electrodes. In operation of the ablation device 10, the ablation elements 25 on the bearing struts 241 are used for ring-like ablation, for example, ring-like ablation at the ostium of the pulmonary vein. The guide rod 54 of the adjustment assembly 50 is movably inserted in the sheath 52, the distal end of the guide rod 54 is movable out from the distal opening of the sheath 52 and connected with the positioning frame 22, and the proximal end of the bearing frame 24 is connected with the distal end of the sheath 52. The axial length of the bearing frame 24 can be controlled by the relative movement between the guide rod 54 and the sheath 52, thereby adjusting the diameter of the bearing frame 24, so that the diameter of the bearing frame 24 matches the size of the target area to be ablated in a ring form.

As shown in FIG. 15, the proximal end of each first primary strut 221 is connected to corresponding two first secondary struts 225, and the proximal ends of the two first secondary struts 225 connected to the proximal end of the same first primary strut 221 extend away from each other. The proximal end of each first secondary strut 225 is joined with the proximal end of the adjacent first secondary strut 225. That is, each first secondary strut 225 is connected with different first secondary struts 225 at the distal and proximal ends thereof. The proximal end of the first secondary strut 225 is joined to the distal end of the bearing strut 241, and the distal end of the first secondary strut 225 is joined to the proximal end of the first primary strut 221. The plurality of first secondary struts 225 are distributed in the circumferential direction of the guide rod 54, and are connected with each other end-to-end to form a wave-like ring structure. The proximal end of each first primary strut 221 is connected to the respective peak of the wave-like ring structure, and the distal end of each bearing strut 241 is connected to the respective valley of the wave-like ring structure. In this embodiment, the end of the first secondary strut 225 connected to the bearing strut 241 extends proximally relative to the end of the first secondary strut 225 connected to the first primary strut 221. In a modified embodiment, the end of the first secondary strut 225 connected to the bearing strut 241 extends distally relative to the end of the first secondary strut 225 connected to the first primary strut 221, that is, the proximal end of each first primary strut 221 is connected to the respective valley of the wave-like ring structure, and the distal end of each bearing strut 241 is connected to the respective peak of the wave-like ring structure.

Preferably, the joint of each first primary strut 221 and the corresponding first secondary struts 225 is bent away from the guide rod 54, the middle of each bearing strut 241 is bent away from the guide rod 54, and the joint of the distal end of each bearing strut 241 and the corresponding first secondary struts 225 is bent toward the guide rod 54. In other words, the joint of each first primary strut 221 and the corresponding first secondary struts 225 protrudes away from the guide rod 54, the middle of each bearing strut 241 protrudes away from the guide rod 54, and the joint of the distal end of each bearing strut 241 and the corresponding first secondary struts 225 is recessed toward the guide rod 54, so that the bearing frame 24 is easier to deform than the positioning frame 22 during the deformation of the ablation assembly 20. When adjusting the relative positional relationship between the guide rod 54 and the sheath 52 to adjust the outer diameter of the bearing frame 24, since the two adjacent first primary struts 221 are limited by the two first secondary struts 225 connected together which pull the first primary struts 221 in the axial and radial directions, the first primary struts 221 will not deform too much in the radial and axial directions, which is beneficial for the positioning frame 22 to maintain the mesh basket-like configuration, with a better alignment when changing the ablation range of the ablation device 100 in diameter. Therefore, the situation that when adjusting the diameter of the bearing frame 24, the positioning frame 22 is greatly deformed and cannot be pressed against the inner wall of the pulmonary vein so that the ablation assembly 20 cannot be aligned around the ostium of the pulmonary vein can be avoided.

In this embodiment, a row of meshes 220 is defined in the axial direction of the positioning frame 22.

In other modified embodiments, the proximal ends of the first secondary struts 225 are further connected with a circle of second secondary struts in the circumferential direction of the guide rod 54, so as to form two rows of meshes 220 in the axial direction of the positioning frame 22. The proximal ends of the first secondary struts 225 are connected to the proximal or distal ends of the second secondary struts. In other modified embodiments, the proximal end of each first primary strut 221 is connected to more than two secondary struts. The first primary strut 221, the first secondary strut 225 and the second secondary strut may be straight, helical or curved. In this embodiment, the width of the first primary strut 221 and/or the first secondary strut 225 is smaller than or equal to the width of the bearing strut 241, facilitating the delivery in the sheath with a smaller diameter.

The bearing strut 241 of the bearing frame 24, the first secondary strut 225 and the second secondary strut can be straight, helical or curved. The helix can be obtained by heat setting after cutting. Alternatively, the helix of the bearing strut 241 can be obtained by relative rotation between the guide rod 54 and the sheath 52 by manipulating the handle (not shown in FIG. 15) during the implantation.

The bearing struts 241 of the bearing frame 24 are connected to each other to form grids and meshes. The shape of the mesh 240 can be arbitrary. The bearing strut 241 extends axially and/or radially. At least some of the bearing struts 241 are provided with electrodes.

The bearing frame 24 can be made of metal material such as nickel-titanium wire. The cross-sectional shape of the nickel-titanium wire is circular, semicircular or other geometric shapes.

Figure 14:
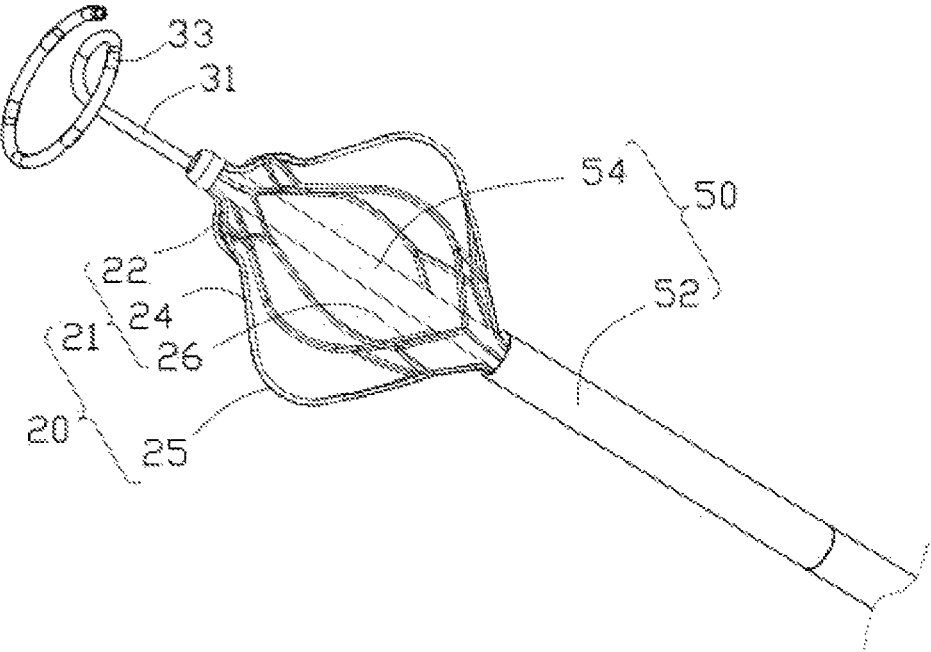
FIG. 14 is a schematic view of an ablation system according to an embodiment of the present disclosure.

Preferably, as shown in FIG. 14 and FIG. 15, the support frame 21 further includes a connection frame 26, which is connected between the bearing frame 24 and the sheath 52. During the deformation of the support frame 21, the deformation ratio of the connection frame 26 is greater than that of the positioning frame 22.

Specifically, when the support frame 21 is fully released, the connection frame 26 is a frame structure with an inner cavity, and the deformation ratio of the positioning frame 22 is smaller than that of the connection frame 26. In this embodiment, the cross section of the strut for forming the connection frame 26 is the same as the cross section of the strut for forming the positioning frame 22 and the cross section of the strut for forming the bearing frame 24. When the guide rod 54 moves relative to the sheath 52, the deformation ratio of the struts of the positioning frame 22 is smaller than that of the connection frame 26. The connection frame 26 is also a mesh structure. The connection frame 26 defines meshes 260, and the opening size of the mesh 260 of the connection frame 26 is smaller than the opening size of the mesh 240 of the bearing frame 24. That is, the opening area of the mesh 260 of the connection frame 26 is smaller than the opening area of the mesh 240 of the bearing frame 24. The opening size of the mesh 260 of the connection frame 26 is larger than the opening size of the mesh 220 of the positioning frame 22, that is, the opening area of the mesh 260 of the connection frame 26 is smaller than the opening area of the mesh 240 of the bearing frame 24.

In this embodiment, since the cross-section of the strut of the positioning frame 22, the cross-section of the strut of the bearing frame 24 and the cross-section of the strut of the connection frame 26 are the same, and the opening area of the mesh 220 is smaller than the opening area of the mesh 260, the connection frame 26 is easier to deform than the positioning frame 22 during the relative movement between the sheath 52 and the guide rod 54. When adjusting the support frame 21, since the meshes of the bearing frame 24 and the connection frame 26 are relatively larger than the meshes of the positioning frame 22, the bearing frame 24 and the connection frame 26 are easily to deform to change the radial dimensions thereof so as to get close to the target tissue area.

The connection frame 26 includes a plurality of second primary struts 261 and a plurality of second secondary struts 265. The plurality of second primary struts 261 are distributed in the circumferential direction of the sheath 52. The proximal end of each second primary strut 261 is connected with the sheath 52, and the distal end of each second primary strut 261 is connected with corresponding second secondary struts 265. The proximal end of each bearing strut 241 is connected with corresponding second secondary struts 265, and the second secondary struts 265 connected with the same bearing strut 241 are connected to different second primary struts 261. The distal end of each bearing strut 241 is connected to the positioning frame.

In this embodiment, the positioning frame 22, the bearing frame 24 and the connection frame 26 are formed in one piece by cutting a nickel-titanium tube. The connection frame 26 includes six second primary struts 261 and a plurality of second secondary struts 265 respectively connected to the distal ends of the second primary struts 261. The distal end of each second primary strut 261 is connected with two second secondary struts 265. The plurality of second primary struts 261 are distributed in the circumferential direction of the sheath 52. Preferably, these second primary struts 261 are evenly distributed in the circumferential direction of the sheath 52. The proximal end of each second primary strut 261 is connected to the distal end of the sheath 52, and the bearing strut 241 is connected with the second primary strut 261 through the second secondary strut 265. Specifically, the distal end of each second primary strut 261 is connected with two second secondary struts 265, and the proximal end of each bearing strut 241 is connected with two second secondary struts 265. The proximal ends of the two second secondary struts 265 connected to the proximal end of the same bearing strut 241 are respectively connected to different second primary struts 261. In this embodiment, when the support frame 21 is fully released, the radial dimension of the frame formed by the second primary struts 261 and the second secondary struts 265 is smaller than the radial dimension of the frame formed by the bearing struts 241. The distal end of the guide rod 54 is connected with the distal end of the positioning frame 22, and the proximal end of the connection frame 26 is connected with the distal end of the sheath 52. The axial length of the bearing frame 24 can be controlled by the relative movement between the guide rod 54 and the sheath 52, thereby adjusting the diameter of the bearing frame 24, so that the diameter of the bearing frame 24 matches the size of the target area to be ablated in a ring form.

As shown in FIG. 15, the distal end of each second primary strut 261 is connected with two corresponding second secondary struts 265, and the distal ends of the two second secondary struts 265 connected to the distal end of the same second primary strut 261 extend away from each other. The distal end of each second secondary strut 265 is joined with the distal end of the adjacent second secondary strut 265, that is, each second secondary strut 265 is connected with different second secondary struts 265 at the distal and proximal ends thereof. The distal end of the second secondary strut 265 is joined to the proximal end of the bearing strut 241, and the proximal end of the second secondary strut 265 is joined to the distal end of the second primary strut 261. The plurality of second secondary struts 265 are distributed in the circumferential direction of the guide rod 54, and are connected with each other end-to-end to form a wave-like ring structure. The distal end of each second primary strut 261 is connected to the respective valley of the wave-like ring structure, and the proximal end of each bearing strut 241 is connected to the respective peak of the wave-like ring structure. In a modified embodiment, the distal end of each second primary strut 261 is connected to the respective peak of the wave-like ring structure, and the proximal end of each bearing strut 241 is connected to the respective valley of the wave-like ring structure.

Optionally, at least one ablation element 25 is provided on the positioning frame 22 and/or the bearing frame 24. The ablation element 25 is an electrode. The ablation energy coupled to the ablation element 25 can be radio frequency, pulse or microwave. In this embodiment, the bearing strut 241 includes a bearing section 243 adjacent to its distal end, and the electrode is arranged on the bearing section 243. Specifically, the electrode is arranged on the side of the bearing section 243 facing away from the guide rod 54.

When the ablation energy coupled to the ablation element 25 is radio frequency, the bearing strut 241 is provided with an insulating layer at the portion where no electrode is provided. In this embodiment, the surface of the bearing strut 241 is covered with a layer of insulating coating at the portion where no ablation element 25 is provided by vacuum coating. The surface of the bearing strut 241 at the portion where the ablation element 25 is provided is exposed, and the bearing strut 241 conducts electrical signals for ablation. Preferably, the ablation element 25 is arranged at the portion of the bearing strut 241 which has the maximum diameter after being compressed in the radial direction.

When the ablation energy coupled to the ablation element 25 is pulse, the ablation element 25 is provided on the bearing frame 24, that is, the electrode is separately arranged on the bearing strut 241. The electrode is made of platinum-iridium alloy, gold or other platinum alloys, and the inner wall of each electrode is welded with a conducting wire with an insulating layer. The bearing strut 241 includes a nickel-titanium wire and an insulating sleeve or other polymer insulating materials surrounding the outside of the nickel-titanium wire. The electrode surrounds the insulating sleeve to ensure the insulation between the electrode and the bearing strut 241. The insulated conducting wire is placed between the bearing strut 241 and the insulating sleeve or other polymer materials. The surface of the nickel-titanium wire is covered with an insulating coating by vacuum coating. That is, the inner surface of each electrode is coupled with the electrode connector on the handle (not shown in FIG. 15) through a conducting wire extending along the surface of the insulating sleeve and the nickel-titanium wire via the guide rod 54, so as to be electrically connected to the external pulse signal source through the electrode connector. The electrode and the conducting wire are connected by welding or other special processes. When the bearing frame 24 is pulled by the guide rod 54 to adjust the diameter, the diameter of the cross section of the bearing strut 241 is in the range of 10 mm to 36 mm.

In one embodiment, the voltage of the pulse signals received by the electrode is in the range of 900V to 2400V, including all values and sub-ranges within the range. The pulse frequency is in the range of 1 kHz to 500 kHz, including all values and sub-ranges within the range. The pulse energy can be a unipolar, high-voltage pulse power supply or a bipolar, high-voltage pulse power supply. In each cycle of the bipolar, high-voltage pulse signal waveform, the positive and negative pulses alternate, and always satisfy positive pulse voltage/negative pulse voltage=negative pulse width/positive pulse width=$\beta$, $\beta$ is continuously adjustable in the range of 1 to 8. Correspondingly, the maximum voltage that the conducting wire can bear is 3000V. All electrodes can be divided into one or more positive-negative sets.

The energy pulse trains received by the electrode include single-phase or biphasic pulses, and each electrode can be configured with single-phase or biphasic pulses with different parameters such as voltage, pulse width, repetition frequency, duty cycle, and number of pulses.

Pulse ablation utilizes a high-intensity pulsed electric field to cause irreversible electrical breakdown of the cell membrane, which is so called irreversible electroporation in the medical field, causing cell apoptosis and thus achieving non-thermal ablation of cells, without heat sink effect. The high-voltage pulse sequence generates less heat and does not need saline irrigation for cooling, which can effectively reduce the occurrence of gas explosion, eschar and thrombus. The treatment time for pulse ablation is short. The treatment time of applying a set of pulse sequences is less than 1 minute, and the whole ablation time is generally no more than 5 minutes. Moreover, since different tissues have different response thresholds to a pulsed electric field, it is possible to perform ablation on the myocardium without disturbing other surrounding tissues, thereby avoiding accidentally injuring surrounding tissues of the pulmonary vein. In addition, compared with other energies, pulse ablation does not require heat conduction to perform ablation on deep tissue, and all cardiomyocytes distributed in the area with a certain electric intensity will suffer from electroporation, which reduces the requirement for the contact pressure of the catheter during ablation. Therefore, even if the ablation device does not completely contact the inner wall of the tissue after entering the atrium, the ablation effect will not be affected. The electrode that releases pulse energy can also collect intracardiac electrical signals. Before ablation, the collected intracardiac electrical signals can be transmitted to the ECG synchronizer, so that the pulse output is synchronized in the absolute refractory period of myocardial contraction, without interference with the heart rate, and reducing sudden cardiac arrhythmia. After ablation, the intracardiac signals can also be used to determine whether the tissue has been completely electrically isolated.

Figure 14A:
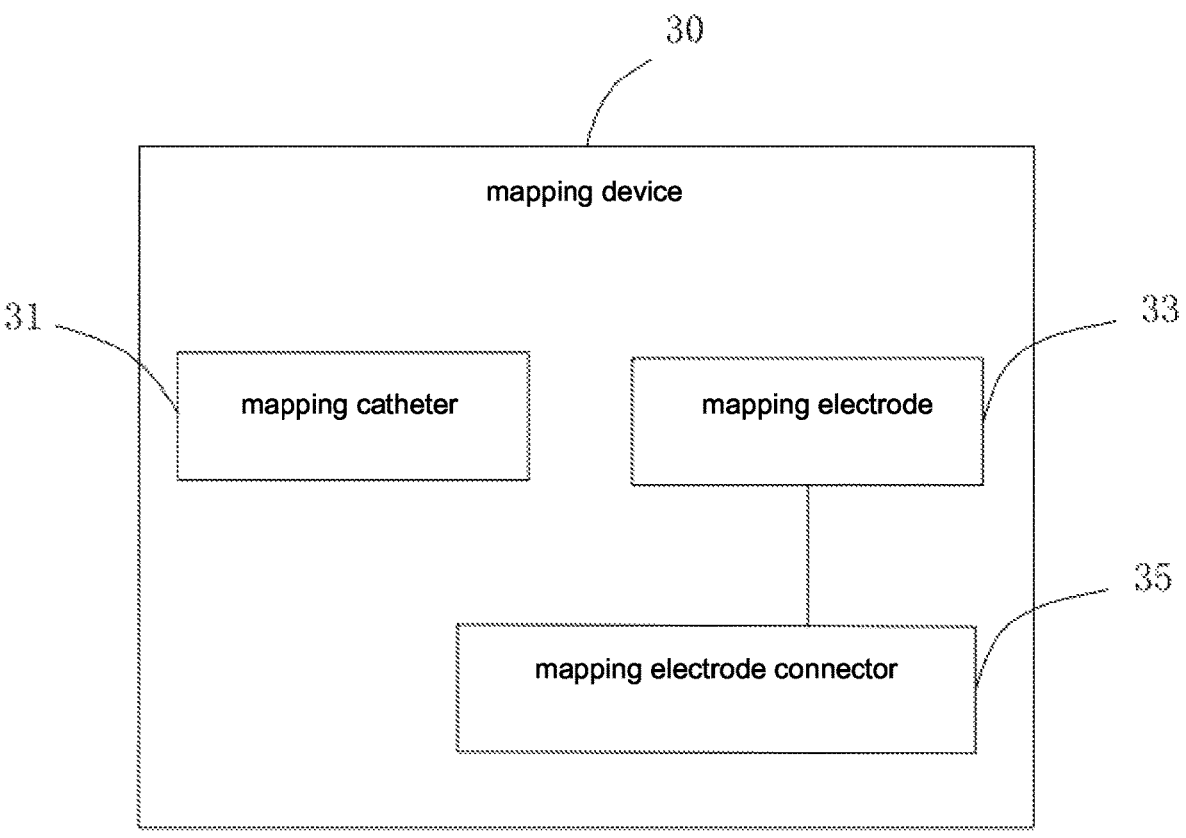
FIG. 14a is a block diagram of a mapping device of the ablation system in FIG. 14.

Optionally, as shown in FIG. 14 and FIG. 14a, the guide rod 54 is hollow tubular. The ablation system further includes a mapping device 30. The mapping device 30 includes a mapping catheter 31, mapping electrodes 33 provided at the distal end of the mapping catheter 31, and a mapping electrode connector 35 connected to the proximal end of the mapping catheter 31. The mapping catheter 31 is inserted in the guide rod 54, and the mapping electrodes 33 are out from the distal end of the guide rod 54 to contact the tissue wall to detect electrophysiological signals in target tissue area. Specifically, the distal end of the mapping catheter 31 extends out of the distal end of the guide rod 54 and then is coiled by at least one turn, and several mapping electrodes 33 are arranged at intervals on the distal end of the mapping catheter 31. The mapping catheter 31 is inserted into the guide rod 54, and the mapping electrodes 33 are out from the distal opening of the guide rod 54 and used to contact the tissue wall to detect electrophysiological signals in the target tissue area. In other embodiments, the distal end of the mapping catheter 31 may be configured as a non-coiled structure, and the mapping electrode 33 is directly provided on the distal end of the mapping catheter 31. Alternatively, the distal end of the mapping catheter 31 can be provided with a balloon, the mapping electrode 33 is provided on the outer surface of the balloon, and the balloon can be inflated by fluid flowing through the lumen of the mapping catheter 31.

In other embodiments, the electrodes on the support frame 21 can be used for both ablation and electrophysiological signal mapping. If the electrodes on the bearing frame 24 can be used for mapping, the mapping device 30 can be removed, and the guide rod 54 can be replaced by a pulling wire. In one embodiment, the electrodes described above can be further used for other purposes such as cardiac pacing.

Optionally, the proximal end of the bearing frame 24 is provided with a connection frame 26 for maintaining the relative positional relationship between adjacent bearing struts 241 so that the distance between ablation elements 25 will not be too small after pulling the guide rod 54, thereby avoiding electric arc. Further, the distribution uniformity of the plurality of bearing struts 241 in the circumferential direction is improved, and the bearing frame 24 is not easy to be twisted and deformed, thereby improving the ablation accuracy of the ablation device 100 and improving the ablation efficiency.

Optionally, in other embodiments, the first primary struts 221 and/or the first secondary struts 225 of the positioning frame 22 are provided with electrodes, and the arrangement of the electrodes refers to the arrangement of the electrodes on the bearing frame 24, which will not be repeated here. The electrode is an ablation electrode or a mapping electrode. If the electrode is a mapping electrode, the mapping catheter 31 in FIG. 14 can be removed, and the guide rod 54 can be replaced by a pulling wire, which is conducive to reduce the diameter of the sheath 52.

As shown in FIG. 16 and FIG. 17, the outer diameter of the bearing frame 24 can be adjusted by pulling the guide rod 54 at the proximal end of the handle (not shown in FIG. 15), so as to adapt to various pulmonary veins of different diameters. In operation, the diameter of the bearing frame 24 can be increased by adjusting so that the ablation element 25 can perform ablation on the tissue by transmitting pulse energy to generate an electric field at the ostium of the pulmonary vein, and the diameter of the bearing frame 24 can be reduced by adjusting so that the ablation element 25 can be placed in the pulmonary vein to perform ablation on the tissue.

Alternatively, the ablation device 10 of the present disclosure can be delivered to a specific site of the heart by percutaneous puncture, so as to perform ablation and electrical isolation on the left atrial appendage, or non PV Foci combined with typical atrial flutter such as superior vena cava, ostium of coronary venous sinus, instead of the pulmonary vein.

The guide rod 54 can be a hollow structure, and the mapping catheter 31 or guide wire can be inserted in the lumen of the guide rod 54 for mapping or positioning.

Figure 18:
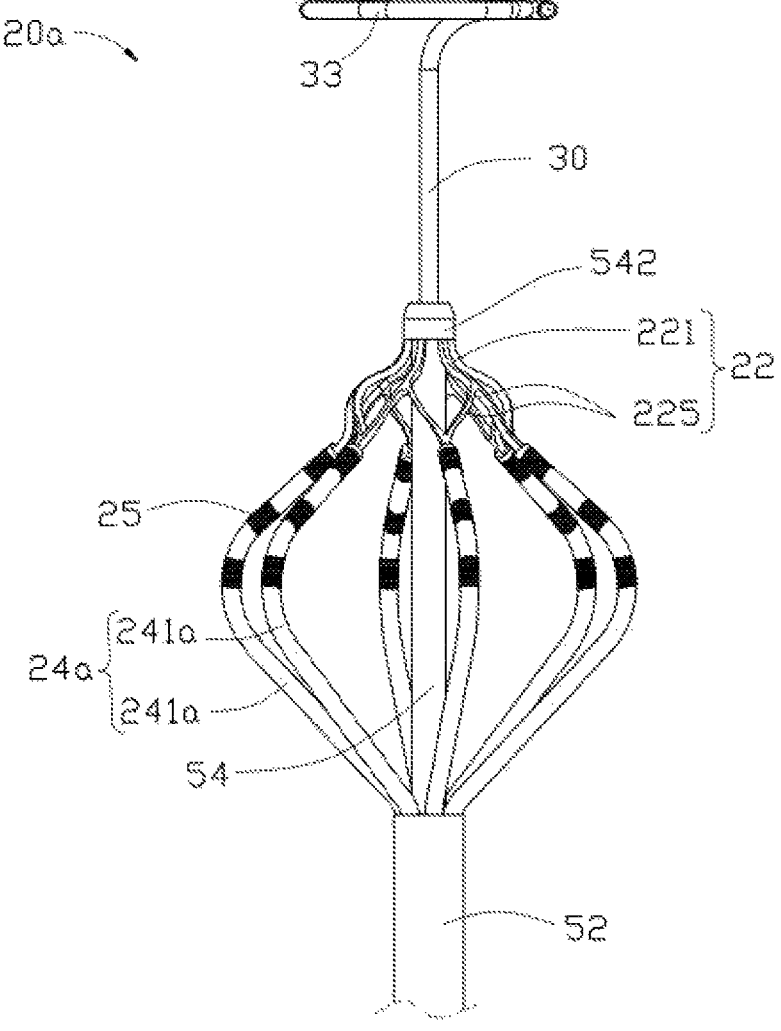
FIG. 18 is a schematic view of an ablation catheter and a mapping device of an ablation system according to another embodiment.
Figure 19:
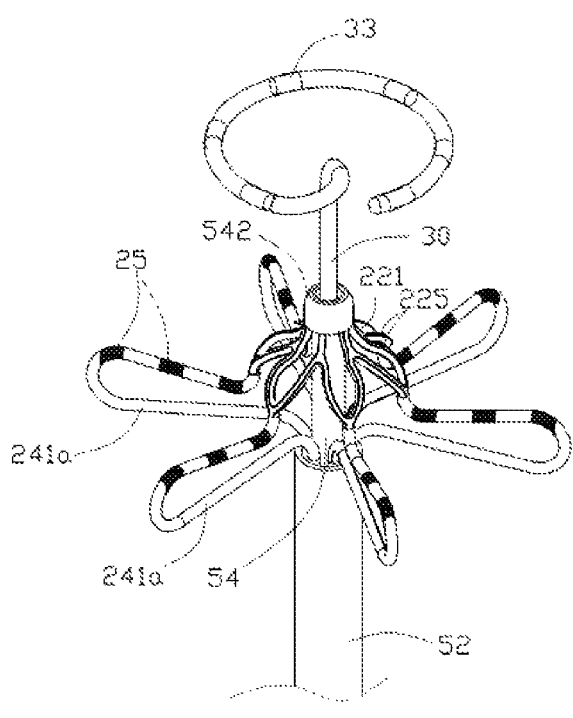
FIG. 19 is a schematic view of the ablation system in FIG. 18, with the ablation catheter in another state.
Figure 20:
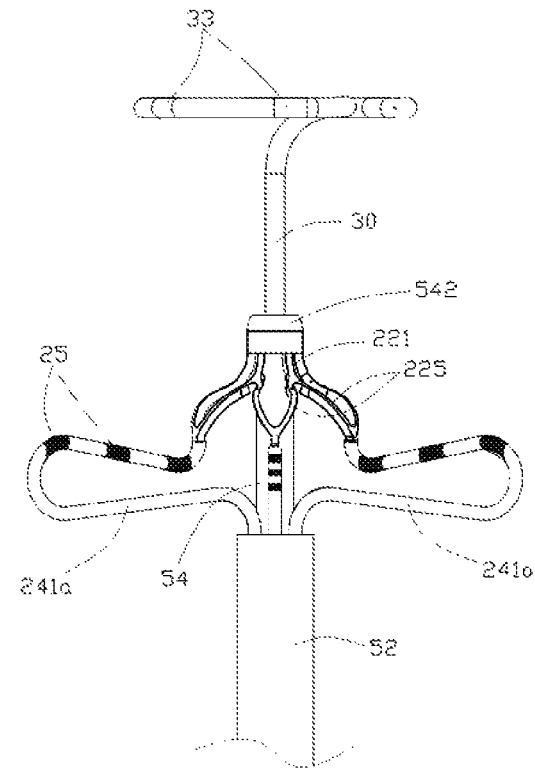
FIG. 20 is a side view of the ablation system in FIG. 19.
Figure 21:
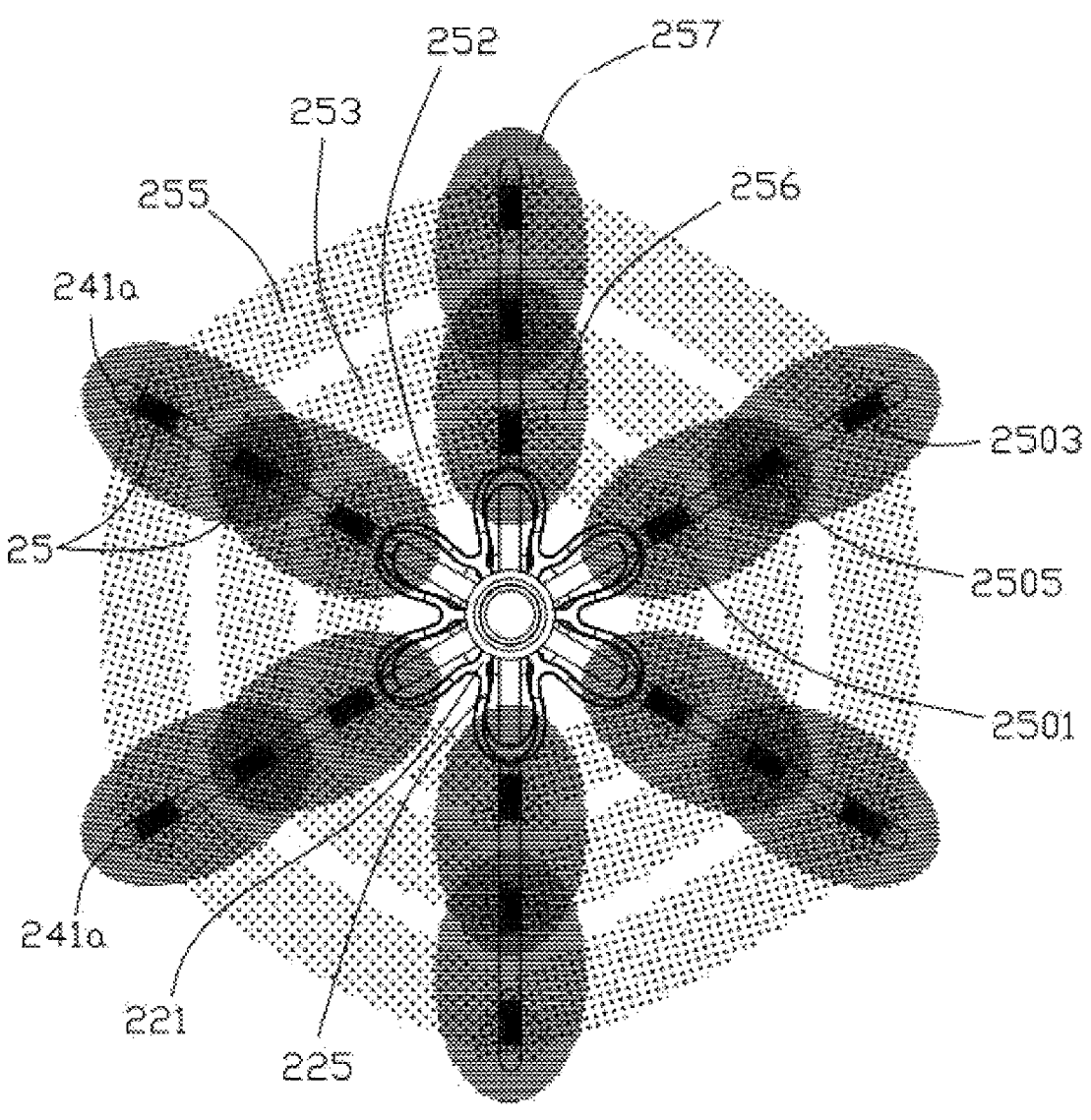
FIG. 21 is a schematic view showing the range of the pulsed electric field in FIG. 20.
Figure 22:
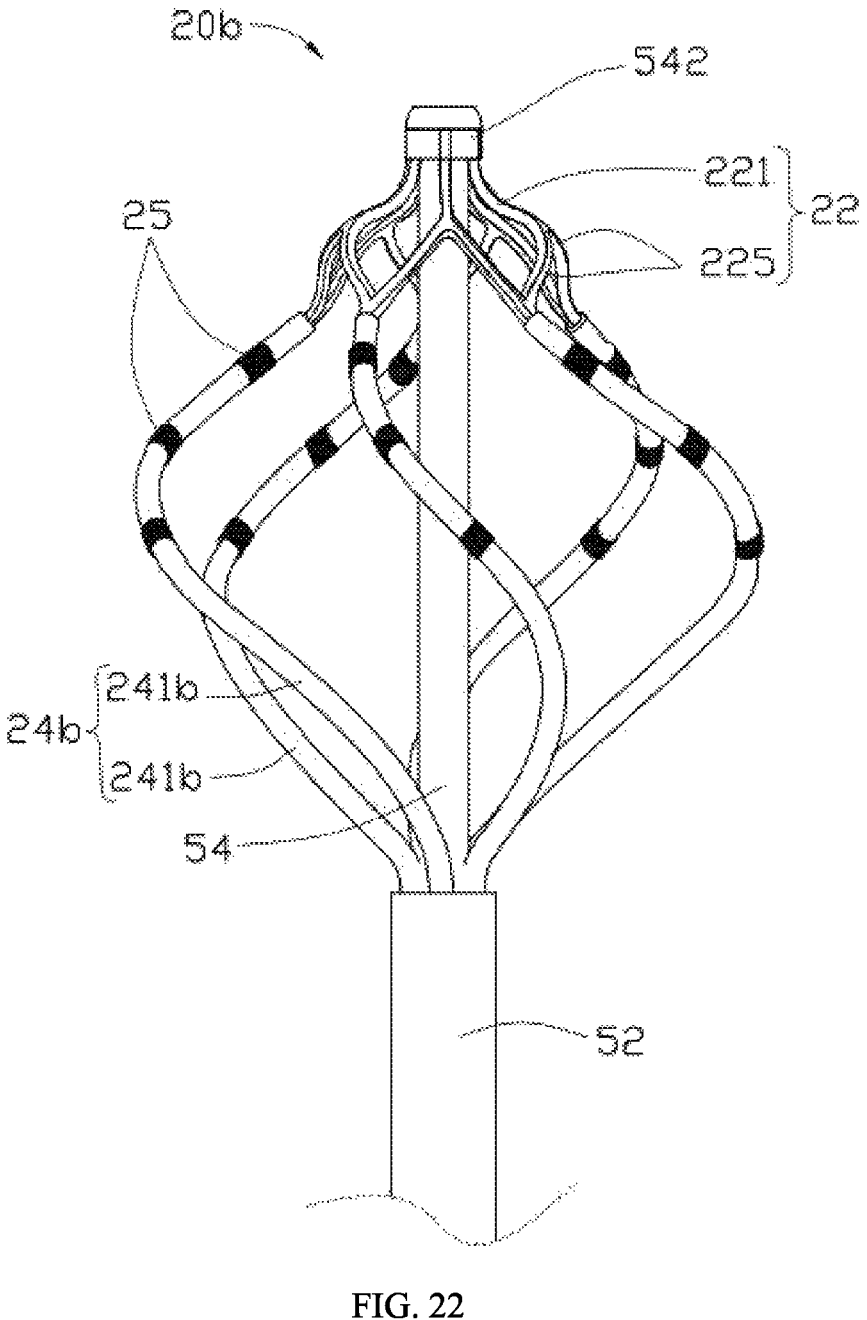
FIG. 22 is a schematic view of an ablation catheter and a mapping device of an ablation system according to another embodiment.
Figure 23:
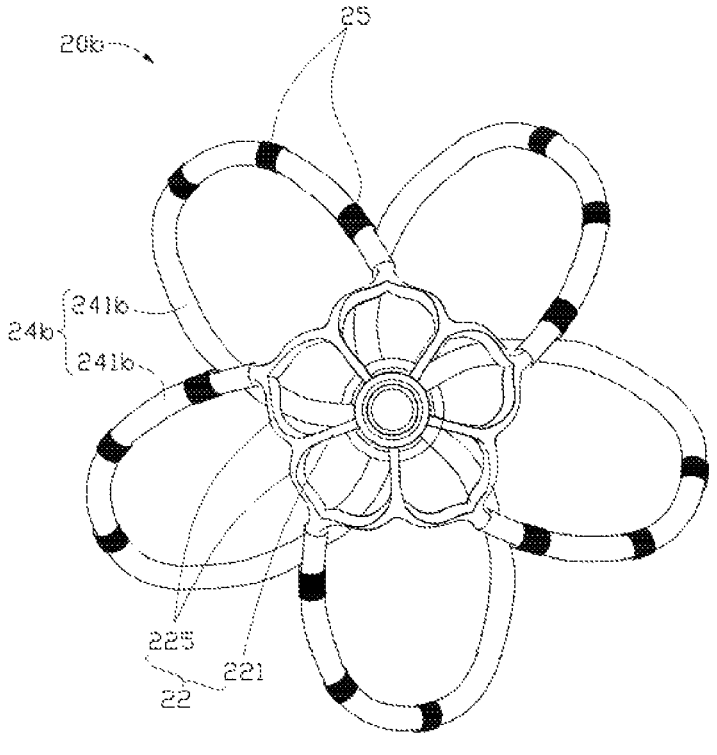
FIG. 23 is a top view of the ablation system in FIG. 22.
Figure 24:
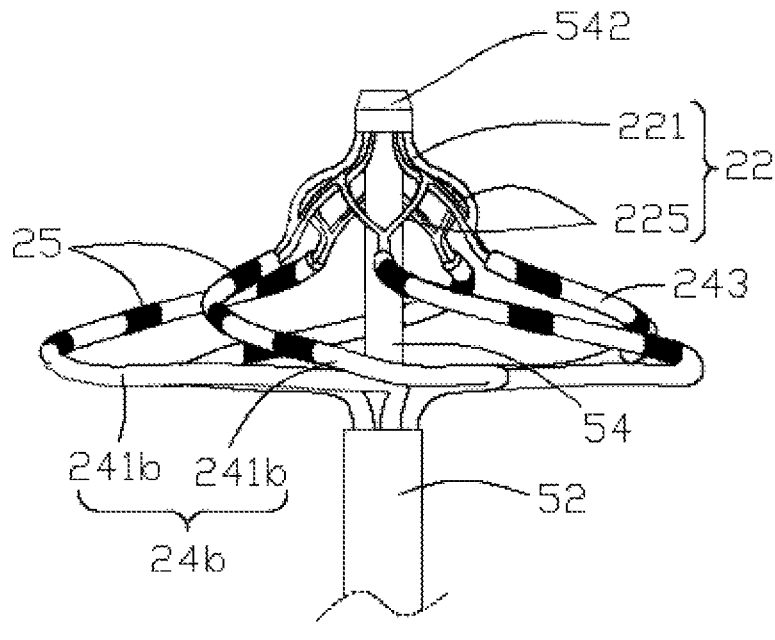
FIG. 24 is a schematic view of the ablation system in FIG. 22 in another state.

Referring to FIGS. 18 to 20, the support frame 21 in this embodiment is not provided with the connection frame 26, so that the proximal end of the bearing frame 24a is directly connected to the distal end of the sheath 52, that is, the proximal end of each bearing strut 241a is connected to the distal end of the sheath 52. Specifically, the bearing frame 24a includes a plurality of bearing struts 241a distributed in sequence in the circumferential direction. The distal ends of the bearing struts 241a are spaced apart from each other, and are connected to the proximal ends of different first secondary struts 225 of the positioning frame 22. The proximal ends of the bearing struts 241a are joined together and connected to the distal end of the sheath 52.

When adjusting the relative positional relationship between the guide rod 54 and the sheath 52 to adjust the outer diameter of the bearing frame 24a, since the adjacent secondary struts of the positioning frame 22 are joined together and limited to each other, the bearing struts 241a of the bearing frame 24a are more likely to deform than the positioning frame 22, so that the radial and axial dimensions of the bearing frame 24a are more likely to change when changing the ablation range of the ablation assembly 20a in diameter. The positioning frame 22 is more likely to maintain the mesh configuration due to the mutual limit of the first primary struts 221 and the first secondary struts 225, with a small deformation ratio, so that a desired alignment can be achieved. The situation that when adjusting the diameter of the bearing frame 24a, the positioning frame 22 is greatly deformed and cannot be pressed against the inner wall of the pulmonary vein so that the adjustment assembly 50 cannot be aligned around the ostium of the pulmonary vein can be avoided.

The bearing struts 241a of the bearing frame 24a are distributed in sequence in the circumferential direction of the guide rod 54. In this embodiment, the bearing struts 241a are evenly distributed in the circumferential direction of the guide rod 54. The bearing frame 24 may include 3 to 8 bearing struts, and in this embodiment, the bearing frame 24 includes six bearing struts.

As shown in FIGS. 18 to 21, each bearing strut 241a is provided with a plurality of ablation elements 25 along its axial direction. In this embodiment, the ablation element 25 is an electrode. The polarities of two adjacent electrodes on the same bearing strut 241a are opposite, and the polarities of adjacent electrodes on two adjacent bearing struts 241a are opposite. The electrodes on the bearing frame 24a define a plurality of imaginary rings distributed in the longitudinal axis of the guide rod 54, and the electrodes on each ring form a ring-like electric field. In this embodiment, each bearing strut 241a is provided with three ablation elements 25 along its axial direction, and three electrode rings are defined on the bearing frame 24a, including a first electrode ring 2501 adjacent to the guide rode 54, a third electrode ring 2503 away from the guide rod 54, and a second electrode ring 2505 located between the first electrode ring 2501 and the third electrode ring 2503. Adjacent electrodes in the first electrode ring are coupled with each other to form an electric field, and these electric fields are superimposed to form a first closed-loop electric field 252 around the axial direction. Adjacent electrodes in the second electrode ring are coupled with each other to form an electric field, and these electric fields are superimposed to form a second closed-loop electric field 253 around the axial direction. Adjacent electrodes in the third electrode ring are coupled with each other to form an electric field, and these electric fields are superimposed to form a third closed-loop electric field 255 around the axial direction.

Further, when forming the pulse electric field, since the polarities of the adjacent electrodes on each bearing strut 241a are opposite, adjacent electrodes on each bearing strut 241a are coupled with each other and form radial electric fields, which are respectively the first radial electric field 256 and second radial electric field 257. The electric field generated by all the electrodes of the entire bearing frame 24a is distributed in the circumferential and radial directions in a net form. The specific configuration of the bearing struts 241a is controlled by the adjustment assembly, so that the electrodes on the bearing struts 241a can form a 3D space electric field which is also called the bulk electric field, with a large ablation range. Therefore, even if the axis of the guide rod 54 does not coincide with the central axis of the pulmonary vein, within a certain offset range, continuous ring-like electrical isolation can be achieved.

Referring to FIG. 22 to FIG. 25, the ablation device according to the present embodiment differs from the above embodiment in that the ablation device does not include the mapping device 30, and the bearing strut 241b is a helical strut. The proximal end of the helical strut is deflected at a preset angle relative to the distal end of the helical strut. Preferably, the preset angle is in the range of 30 degrees to 70 degrees.

The deflection angles (that is, the helix angles) of the portions of each bearing strut 241b with different distances from the proximal end can be different. Specifically, the helix angles of the portions of the bearing strut 241b between the proximal end and the distal end are greater than the helix angles at the proximal end or the distal end. That is, the maximum helical angle of the helical bearing strut 241b corresponds to the portion between the proximal end and the distal end of the bearing strut 241b. In one embodiment, the helix angle of the bearing strut 241b at the midpoint between the proximal end and the distal end is greater than the helix angle at the proximal end or the distal end of the bearing strut 241*b*, and the helix angle decreases from the midpoint toward the two sides. In one preferred embodiment, the helix angles of the bearing strut 241*b* on two sides of the midpoint are distributed symmetrically. Such helical configuration allows the ablation assembly 20*b* to have better compliance and can contact the target tissue area more closely.

Figure 25:
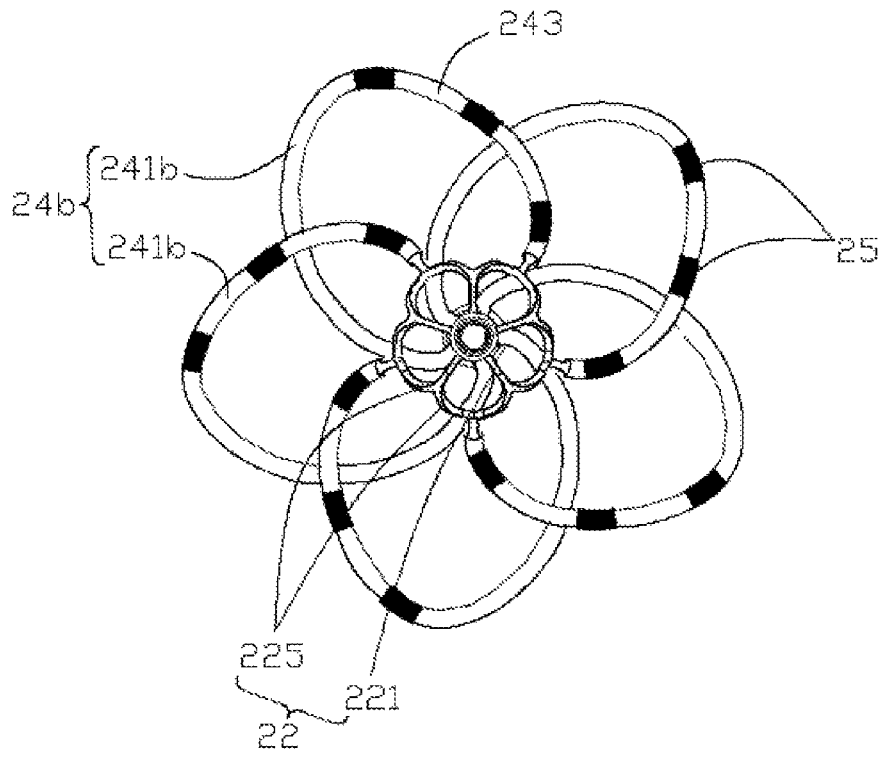
FIG. 25 is a top view of the ablation system in FIG. 24.

In this embodiment, the helical bearing struts 241*b* are evenly distributed around the guide rod 54. The number of bearing struts 241*b* can be in the range of 3 to 10. The shape of the bearing struts 241*b* projected to the cross-section perpendicular to the axis is oval, circle or any other symmetrical geometric shape. In this embodiment, the bearing frame 24*b* includes six bearing struts 241*b*, and each bearing strut 241*b* is provided with three ablation elements 25 spaced apart from each other along its axial direction. Each ablation element 25 is an electrode. As shown in FIG. 25, the bearing strut 241*b* includes a bearing section 243 adjacent to its distal end, and the ablation elements 25 are provided on the bearing section 243. Specifically, the ablation element 25 surrounds the outer periphery of the bearing section 243. In this embodiment, the ablation element 25 is an electrode, the shape of which conforms to the helical form of the respective bearing strut 241*b*, and the electrode is arranged on the bearing section 243 adjacent to the distal end of the bearing strut 241*b*, so that during the ablation on the ostium of the pulmonary vein, the distance between electrodes will not be too close after pulling the guide rod 54, thereby avoiding electric arc, and the electrodes of the ablation assembly 20*b* can contact and conform to the atrial tissue well.

In one embodiment, the polarity of the electrodes on each bearing strut 241*b* is the same, which is opposite to that of the electrodes on the adjacent helical bearing strut 241*b*.

The ablation element 25 can be further used for potential mapping, to contact the tissue wall and detect electrophysiological signals in the target tissue area. The ablation element 25 is an electrode. Each bearing strut 241*b* is provided with a plurality of electrodes, and at least one of the plurality of electrodes can be used for potential mapping. In this embodiment, each bearing strut 241*b* is provided with three electrodes spaced apart from each other along its axial direction, i.e., the first electrode, the second electrode and the third electrode from the distal end toward the proximal end in turn. The third electrode is located on the portion of the bearing strut 241*b* farthest away from the axis of the sheath 52. In one embodiment, the second electrode and the third electrode on each bearing strut 241*b* can be used as mapping electrodes. In other embodiments, the third electrode on each bearing strut 241*b* can be used as a mapping electrode.

Figure 26:
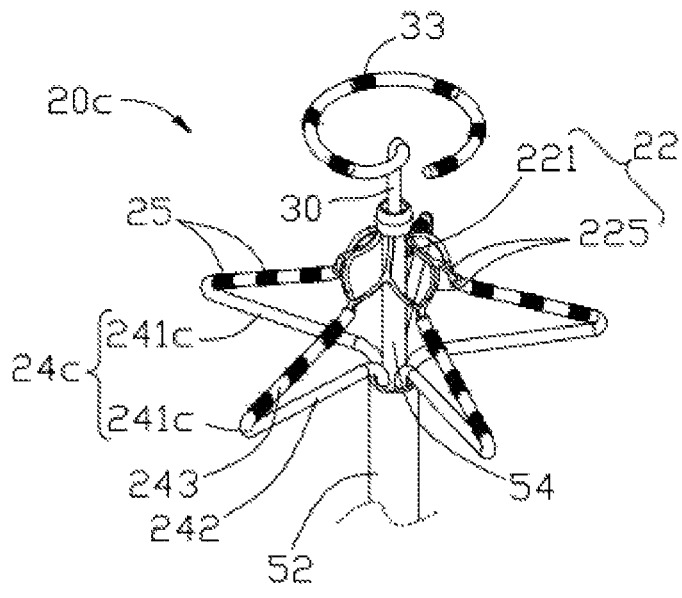
FIG. 26 is a schematic view of an ablation catheter and a mapping device of an ablation system according to another embodiment.
Figure 27:
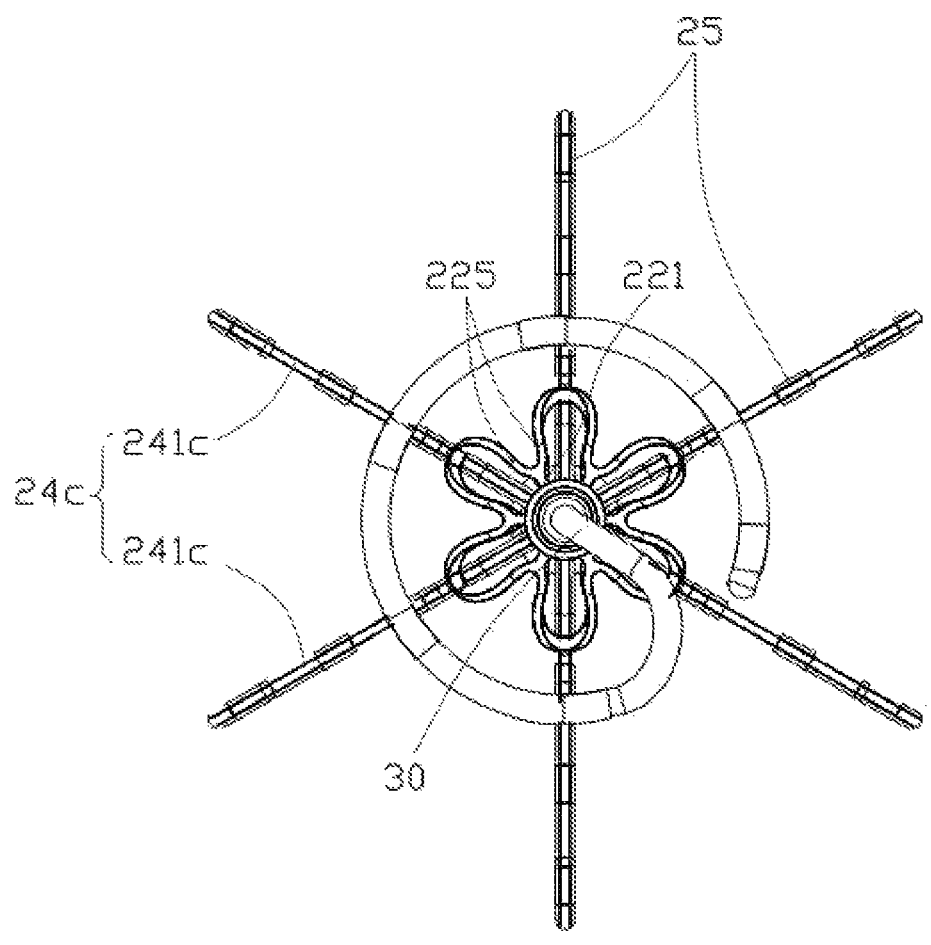
FIG. 27 is a top view of the ablation system in FIG. 26.

Referring to FIG. 26 and FIG. 27, the bearing strut 241*c* of the ablation device according to this embodiment is a bent strut. The bent strut includes an extension section 242 extending outward in the radial direction of the sheath 52 and a bearing section 243 connected between the end of the extension section 242 away from the sheath 52 and the positioning frame 22. The angle between the extension section 242 and the bearing section 243 is greater than 0 degree and less than 90 degrees. Preferably, the angle between the extension section 242 and the bearing section 243 ranges from 30 degrees to 60 degrees.

The bearing struts 241*c* are distributed in the circumferential direction of the sheath 52, and the number of the bearing struts 241*c* may be in the range of 3 to 10. These bearing struts 241*c* form the bearing frame 24*c* in a tapered form. In this embodiment, the bearing frame 24*c* includes six bearing struts 241*c*, and the bearing section 243 of each bearing strut 241*c* is provided with three ablation elements 25 spaced apart from each other along its axial direction. Each ablation element 25 is an electrode, the shape of which conforms to the shape of the corresponding bearing strut 241*c*. The electrodes are provided on the middle and opposing ends of the bearing section 243.

When performing ablation on the ostium of the pulmonary vein, the bearing frame 24*c* is deformed by pulling the guide rod 54, so that the axial dimension of the bearing frame 24*c* becomes smaller, and the angle between the extension section 242 and the bearing section 243 of each bearing strut 241*c* becomes smaller until the electrodes of the ablation assembly 20*c* can contact the atrial tissue well.

Figure 28:
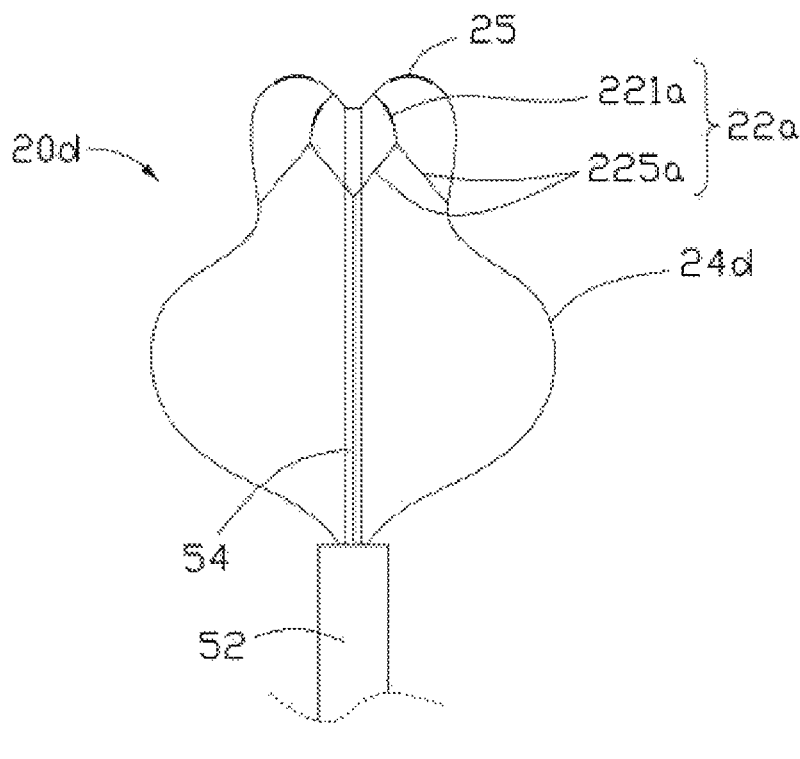
FIG. 28 is a schematic view of an ablation catheter according to another embodiment.
Figure 29:
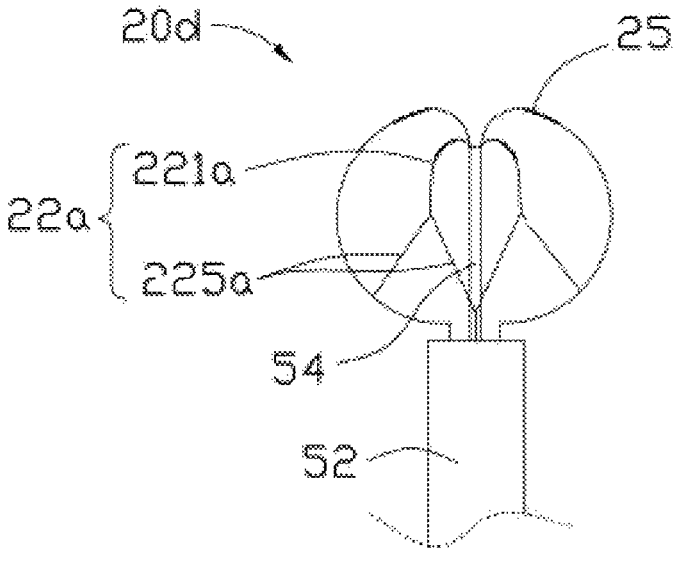
FIG. 29 is a schematic view of the ablation catheter in FIG. 28 in another state.

Referring to FIG. 28 and FIG. 29, the positioning frame 22*a* of the ablation device according to this embodiment has a turn-up structure, that is, the distal part of the positioning frame 22*a* is connected to the guide rod 54 in the direction from the distal end toward the proximal end. Specifically, the distal end of each first primary strut 221*a* exceeds the distal end of the guide rod 54, and an end of the first primary strut 221*a* extends from the distal end thereof toward the proximal end and connects with the guide rod 54. The ablation element 25 is provided on the positioning frame 22*a* at the distal end of the positioning frame 22*a*. Specifically, the ablation element 25 is provided on the side of the first primary strut 221*a* facing away from the guide rod 54. Preferably, the ablation element 25 is provided at a distal end of the positioning frame 22*a*.

In this embodiment, the distal end of the first primary strut 221*a* is clamped in the double-layer steel sleeve at the distal end of the guide rod 54. The first primary strut 221*a* is bent into a circular arc at the distal end of the positioning frame 22*a*. This structure can avoid damage to the atrial tissue caused by a protruding tip of the distal end of the positioning frame 22*a*, and better conform to the anatomical structure of the heart area to be ablated. Such turn-up structure can also be used for ablation therapy for patient with cardiac hypertrophy.

As shown in FIG. 29, after the bearing frame 24*d* is withdrawn into the sheath 52, while the positioning frame 22*a* is exposed from the distal end of the sheath 52, the positioning frame 22*a* is similar to a sphere. The ablation elements 25 are used for point ablation (focal ablation) in the interior of the heart. That is to say, in this embodiment, the ablation assembly 20*d* can be used not only for ring-like ablation, but also for focal ablation, providing a new application for the ablation assembly 20*a*, which can be flexibly configured and adjusted according to clinical needs, and has good application prospect. In other modified embodiments, the ablation elements 25 may be provided at the portion of the positioning frame 22*a* with the maximum radial dimension, facilitating access to the target tissue area.

Figure 30:
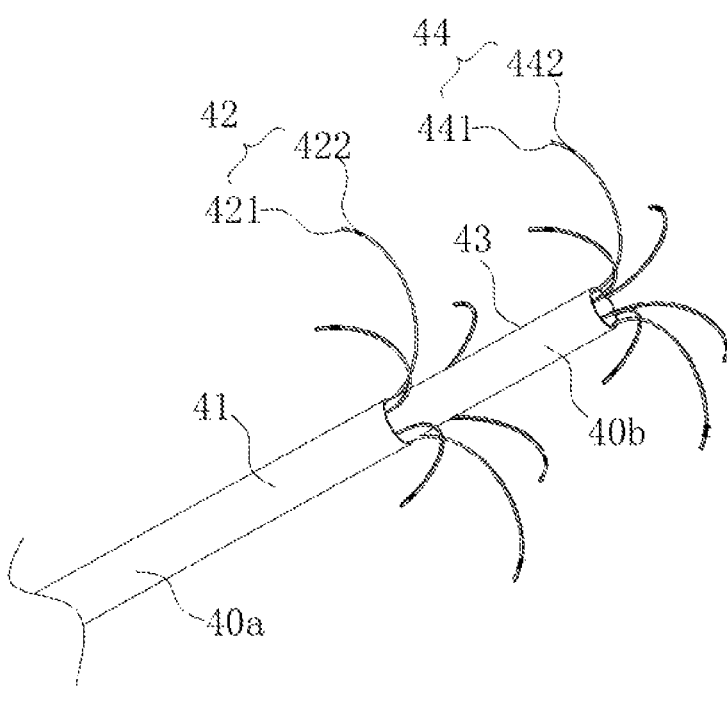
FIG. 30 is a schematic view of an ablation device according to another embodiment.

In another embodiment, as shown in FIG. 30, the support frame can be an umbrella-like self-expandable stent.

FIG. 30 illustrates at least two ablation catheters inserted one in the other. Although FIG. 30 shows two ablation catheters, in other embodiments the number of ablation catheters may be more than two. For ease of description, two ablation catheters are defined here as a proximal ablation catheter 40*a* and a distal ablation catheter 40*b*.

The proximal ablation catheter 40*a* includes a proximal sheath 41 and a proximal ablation assembly 42 connected to the distal end of the proximal sheath 41. The distal ablation catheter 40*b* includes a distal sheath 43 and a distal ablation assembly 44 connected to the distal end of the distal sheath 43. The proximal sheath 41 has a central lumen for receiving the slidable distal sheath 43, and the distal sheath 43 is slidably received in the central lumen of the proximal sheath 41.

The proximal ablation catheter 40*a* and the distal ablation catheter 40*b* are movable back and forth to change the axial distance therebetween. The axial distance between the proximal ablation assembly 42 and the distal ablation assembly 44 is adjusted by axially moving the proximal ablation catheter 40*a* and the distal ablation catheter 40*b*, thereby controlling the size and shape of the ablation lesion. The proximal ablation catheter 40*a* is independently axially movable relative to the distal ablation catheter 40*b*, and the distal ablation catheter 40*b* is also independently axially movable relative to the proximal ablation catheter 40*a*. Further, the proximal ablation assembly 42 and the distal ablation assembly 44 are compressible in the lumen or radially expandable to form umbrella-like structures.

The proximal ablation assembly 42 includes a plurality of proximal struts 421 and proximal electrodes 422 provided on the proximal struts 421. The proximal ends of the plurality of proximal struts 421 are converged to the distal end of the proximal sheath 41. After the proximal struts 421 are released, the distal ends thereof expand radially outward and stretch to form the umbrella-like structure. The proximal strut 421 may be made of an elastic metal wire, such as a nickel-titanium alloy wire, and the proximal strut 421 may be welded and fixed to the distal end of the proximal sheath 41.

The distal ablation assembly 44 includes a plurality of distal struts 441 and distal electrodes 442 provided on the distal struts 441. The proximal ends of the plurality of distal struts 441 are converged to the distal end of the distal sheath 43. After the distal struts 441 are released, the distal ends thereof expand radially outward and stretch to form the umbrella-like structure. The distal strut 441 may be made of an elastic metal wire, such as a nickel-titanium alloy wire, and the distal strut 441 may be welded and fixed to the distal end of the distal sheath 43.

Both the proximal electrode 422 and the distal electrode 442 can be used as an ablation electrode or a mapping electrode. Alternatively, one of the proximal electrode 422 and the distal electrode 442 can be used as an ablation electrode, and the other can be used as a mapping electrode. For the ablation catheter for mapping, it can be regarded as a mapping device for the ablation system. When both the proximal electrode 422 and the distal electrode 442 are ablation electrodes, taking pulse ablation as an example, the electrodes on the proximal struts 421 can be configured as alternately spaced positive and negative electrodes, that is, the electrode polarities of the electrodes on the two adjacent proximal struts 421 are opposite. The electrodes on the distal struts 441 can also be configured as alternately spaced positive and negative electrodes, that is, the electrode polarities of the electrodes on the two adjacent distal struts 441 are opposite. In this way, all the electrodes on the proximal struts 421 can form a first ablation ring, and all the electrodes on the distal struts 441 can form a second ablation ring. The diameters of the first ablation ring and the second ablation ring vary according to the arrangement of the proximal electrodes and the distal electrodes. For example, if the distances L1 from the proximal electrodes 422 provided on the respective proximal struts 421 to the central axis of the proximal sheath 41 are equal, and the distances L2 from the distal electrodes provided on the respective distal struts 441 to the central axis of the distal sheath 43 are equal, and L1 is greater than L2, it means that the diameter of the first ablation ring is greater than the diameter of the second ablation ring. In this way, the first ablation ring or the second ablation ring can be selected for ablation according to the size of the respective tissue to be ablated, the first ablation ring or the second ablation ring can be flexibly selected for ablation according to the size of the ostium of the patient's pulmonary vein.

An electric field for ablation can also be generated between the positive and negative electrodes on the proximal struts 421 and the distal struts 441, and the electric intensity changes with the relative position relationship between the proximal ablation assembly 40*a* and the distal ablation assembly 40*b*.

Figure 31:
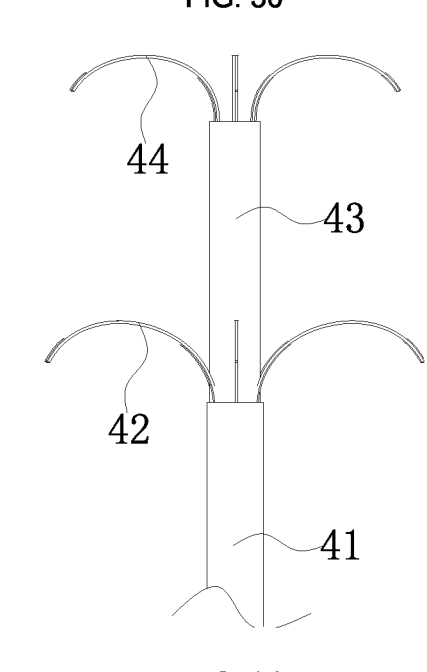
FIG. 31 is a side view of the ablation device in FIG. 30.
Figure 32:
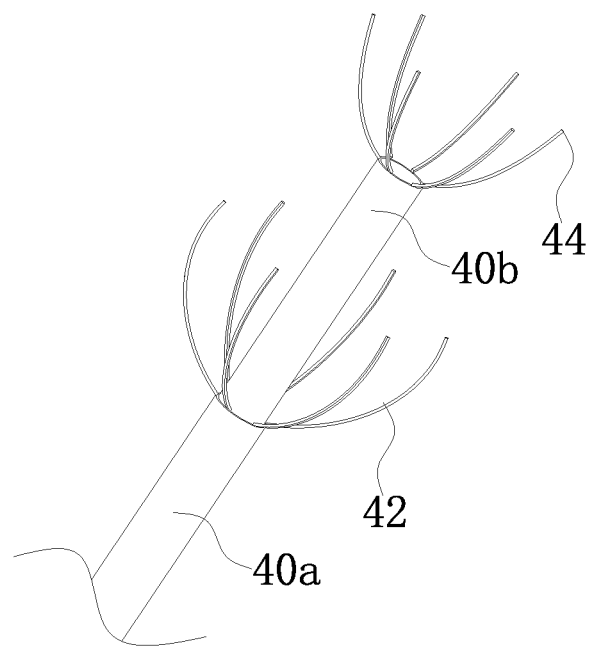
FIG. 32 is a schematic view of an ablation device according to another embodiment.
Figure 33:
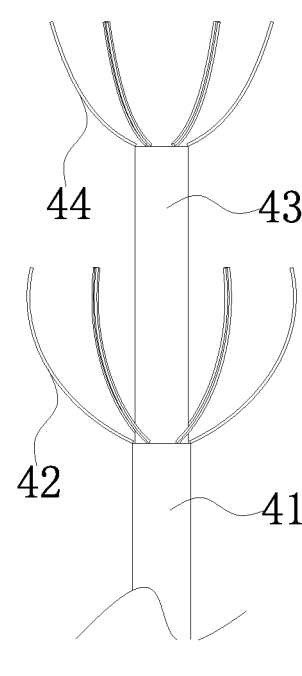
FIG. 33 is a side view of the ablation device in FIG. 32.

It would be appreciated that FIG. 30 and FIG. 31 show ablation assemblies 42 and 44 the openings of the umbrella-like structures of which both face towards the proximal end of the electrode assembly, that is, the recesses formed by the bent proximal struts 421/distal struts 441 are located at the proximal side. It would be appreciated that in other embodiments, as shown in FIG. 32 and FIG. 33, the opening of the umbrella-like structure of the ablation assembly 42 (44) can face toward the distal end, that is, the recesses formed by the bent proximal struts 421/distal struts 441 are located at the distal side.

Figure 34:
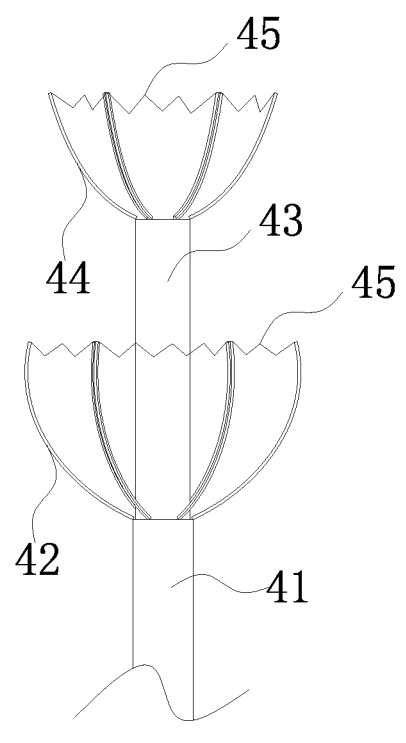
FIG. 34 is a schematic view of an ablation device according to another embodiment.

As shown in FIG. 34, the opening of the ablation assembly 42 (44) can be further provided with a plurality of shape limiting strips 45, and each shape limiting strip 45 connects two adjacent proximal struts 421 or two adjacent distal struts 441 in the circumferential direction. The shape limiting strips 45 at the distal end of each ablation assembly 42 (44) define a circle of shape limiting strips 45. The shape limiting strip 45 is used to remain the distance between two adjacent proximal struts 421 or two adjacent distal struts 441 unchanged, avoiding distance change between the adjacent two proximal struts 421 or adjacent two distal struts 441 which would cause change of pulse electric field generated by the electrodes of two adjacent proximal struts 421 or two adjacent distal struts 441. The figure shows that the shape limiting strips 45 are wave-like, and can be radially compressed and expanded. The wave-like shape limiting strips 45 can be shaped by nickel-titanium wire. The wave-like shape limiting strips 45 facilitate the recovery of the ablation assembly into the lumen of the outer tube. It should be noted that the arrangement of the electrodes in this embodiment can refer to the embodiment in which the opening of the umbrella-like structure faces toward the proximal end, i.e., the embodiments shown in FIGS. 30 and 31.

The above exemplarily illustrates several configurations of the self-expandable support frame 152 being cage-like and umbrella-like stents, and the self-expandable support frame 152 can use other configurations such as sphere-like and basket-like (single-basket or multiple-basket) stents, but not limited thereto.

Another optional configuration for the self-expandable support frame will be introduced below.

Figure 35:
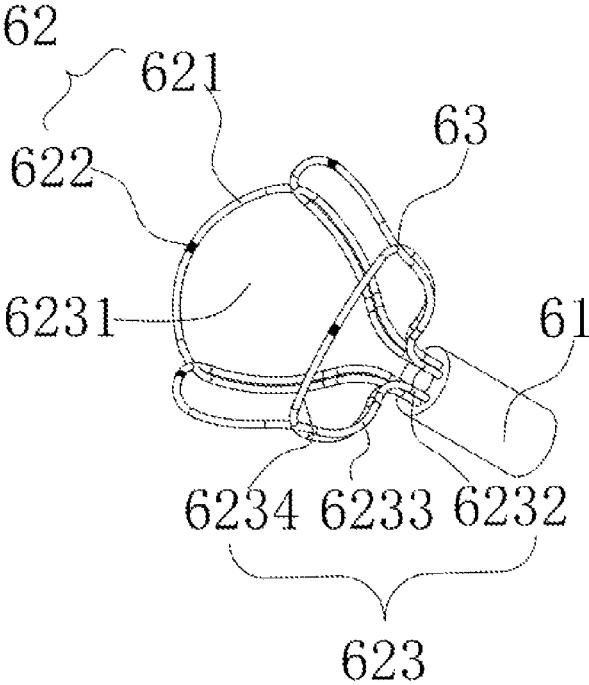
FIG. 35 is a schematic view of an ablation catheter according to a further embodiment, with the ablation assembly in an expanded state.

Referring to FIG. 35, another configuration of the ablation catheter is shown. The ablation catheter in this embodiment includes a sheath 61 and an ablation assembly 62. The ablation assembly 62 includes a support frame 621 and electrodes 622 provided on the distal end of the support frame 621. The expanded support frame 621 is in a flower form.

Specifically, the support frame 621 includes a plurality of strips 623, and the two opposing free ends of each strip 623 are connected to the distal end of the sheath 61. Each strip 623 defines a petal structure, that is, each strip 623 with an enclosed structure defines a window 6231 therein. A plurality of petal structures are distributed in the circumferential direction of the sheath 61. After the support frame 621 radially compressed in the outer tube moves out of the outer tube, the support frame 621 can radially expand and stretch to form the flower structure, to allow ablation on the ostium of the pulmonary vein. The strip 623 is made of metal or non-metallic material, preferably shape memory metal material, such as nickel-titanium alloy material.

In this embodiment, each strip 623 is intersected with another adjacent strip 623. The strip 623 includes two free sections 6232 at the opposing ends thereof and connected to the sheath 61, two side arms 6233 respectively connected to the distal ends of the two free sections 6232, and a bearing arm 6234 connected between the distal ends of the two side arms 6233. Each bearing arm 6234 is provided with at least one electrode 622. Two adjacent strips 623 are intersected with each other. The intersection design allows the profile of the expanded support frame 621 to be maintained, and can avoid the misalignment of two adjacent petal structures. It can be understood that two adjacent strips 623 may not intersect with each other, and the petal structures are distributed at intervals in the circumferential direction of the sheath 61, that is, the side arms 6233 of two adjacent strips 623 are spaced apart from each other.

Figure 36:
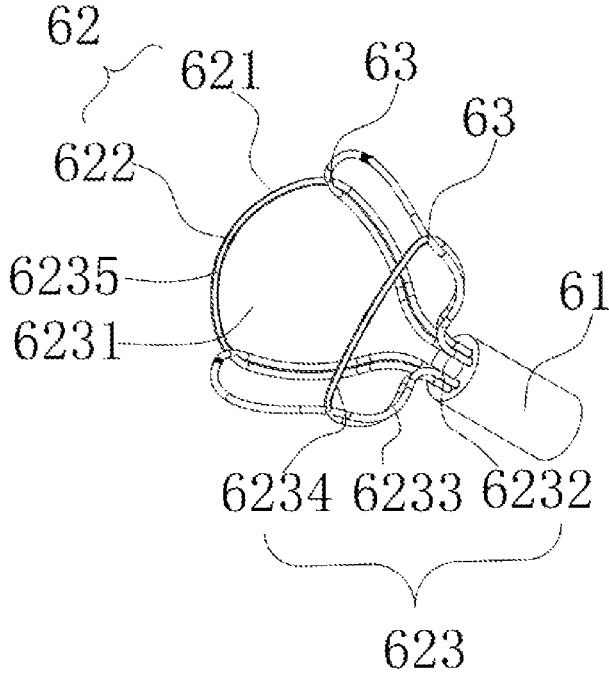
FIG. 36 is a schematic view of an ablation catheter according to a further embodiment, with the ablation assembly in an expanded state.
Figure 37:
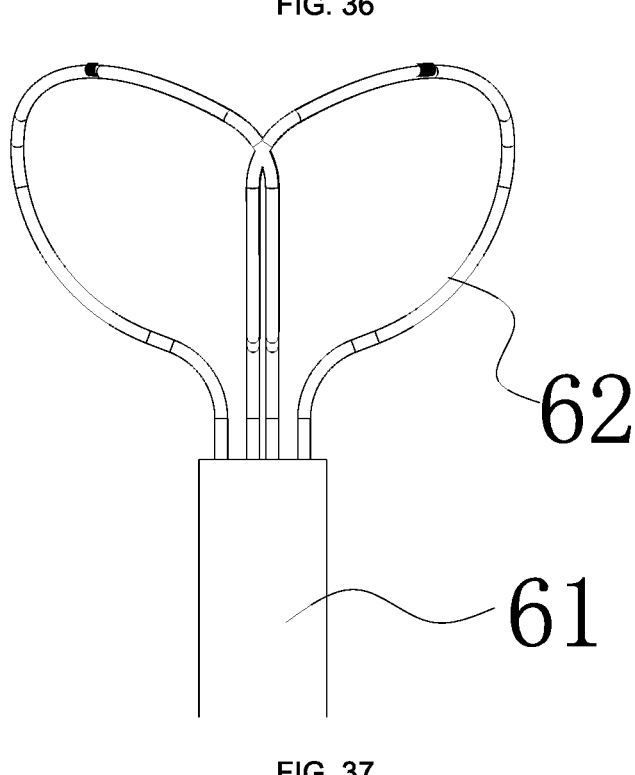
FIG. 37 is a partial schematic view of the ablation catheter in FIG. 36.
Figure 38:
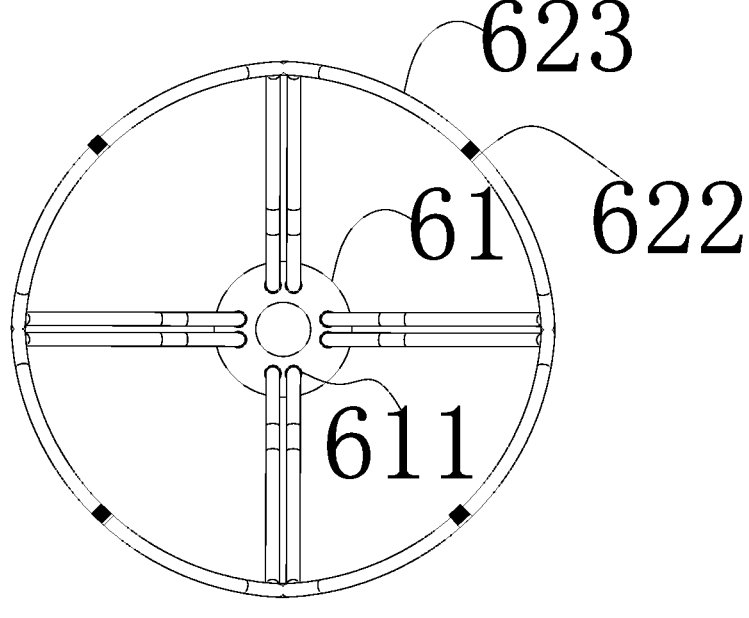
FIG. 38 is a top view of the ablation catheter in FIG. 36.

It should be noted that, in the embodiment where two adjacent strips 623 are intersected with each other, the two adjacent strips 623 can be fixed by welding. The intersection 63 of the two adjacent strips 623 can be understood as a fixed node. In an optional modified embodiment, the intersection 63 of two adjacent strips 623 may be a movable node. For example, as shown in FIG. 36 to FIG. 38, two adjacent strips 623 are inserted one in the other. That is, one strip 623 is provided with a passage 6235 for the other strip 623 to pass through, which will be described in detail with reference to FIGS. 36 to 38.

Referring to FIGS. 36 to 38, a passage 6235 is defined in the bearing arm 6234 of the strip 623. The passage 6235 passes through the bearing arm 6234 in the radial direction and extends along the axial direction of the bearing arm 6234 to allow the other strip 623 to be slidably inserted therein. The support frame 621 may be configured such that the support frame 621 includes first strips and second strips which are alternately distributed in the circumferential direction of the sheath 61, the first strip has passages 6235 on two sides of the bearing arm 6234 respectively, and the adjacent second strip passes through the passage 6235 on the adjacent side.

Figure 39:
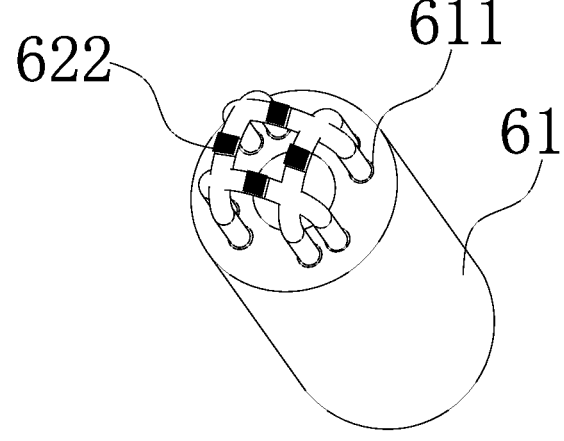
FIG. 39 is a schematic view of the ablation catheter in FIG. 36 in a compressed state.
Figure 40:
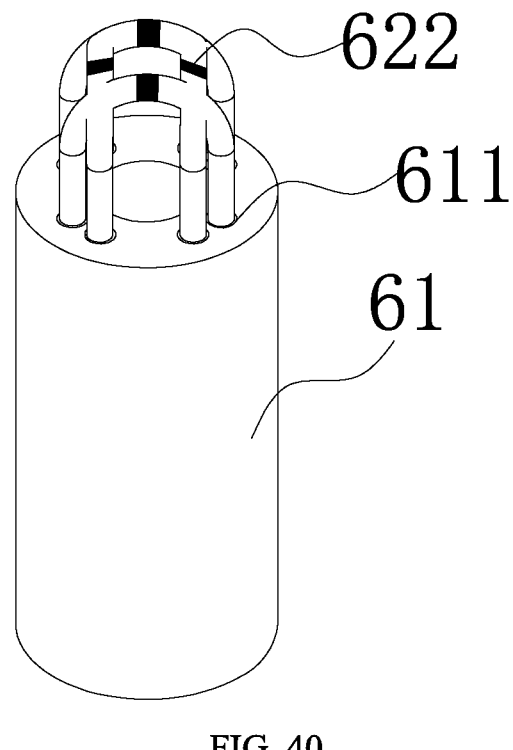
FIG. 40 is a schematic view of the ablation catheter in FIG. 39 from another perspective.
Figure 41:
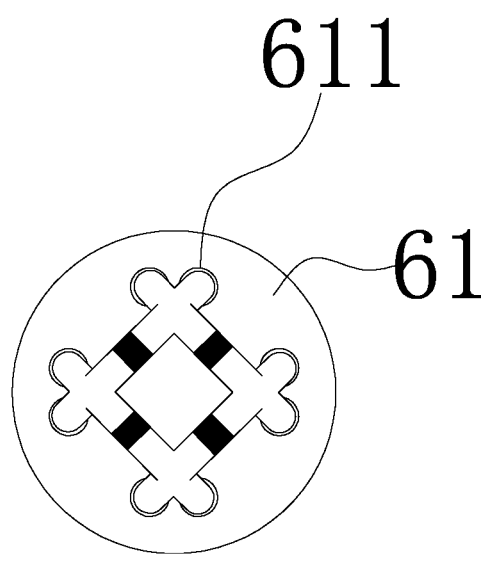
FIG. 41 is a top view of the ablation catheter in FIG. 39.

In addition, it should be noted that the free sections 6232 of all the strips 623 pass through the respective through holes 611 extending axially through the sheath 61 and converge together at the proximal end of the sheath 61 (not shown). Referring to FIGS. 39 to 41, by simultaneously pulling the proximal ends of the free sections 6232 of all the strips 623 which can be controlled by the handle (not shown in FIG. 36), the distal ends of the strips 623 can be retracted close to the distal surface of the sheath 61. When the number of strips 623 is four, the structure retracted close to the distal surface of the sheath 61 assumes a #shape. The strips 623 may have other number, which is not limited here. Moreover, the electrode 622 on each bearing arm 6234 is located between two adjacent groups of through holes 611 (each group includes two through holes 611) in the distal surface of the sheath 61, and the movable node of the two adjacent intersected strips 623 is located between two adjacent through holes 611 in the same group of through holes 611.

According to the above configuration, before the support frame 621 is retracted and compressed, as shown in FIGS. 36 to 38, the electrodes 622 on the support frame 621 form a first ablation ring with a greater diameter, so as to perform ablation on the ostium of the pulmonary vein. After the support frame 621 is retracted and compressed, as shown in FIGS. 39 to 41, the electrodes 622 on the support frame 621 form a second ablation ring with a smaller diameter which is further smaller than the outer diameter of the sheath 61, so as to perform local ablation on the lesion tissue. It should be noted that, in case of pulse ablation, the electrodes 622 can be configured as positive and negative electrodes alternately distributed in the circumferential direction, or all of them can be configured as positive electrodes, with the negative electrode arranged outside the body. Alternatively, the electrodes 622 in this embodiment can be configured to use radio frequency ablation energy.

As an alternative of the support frame 152 being a self-expandable and shape memory stent, the support frame 152 can be a balloon that can be expanded by injecting fluid, in which case the ablation element 153 can be provided on the outer surface of the balloon so as to perform ablation and isolation on the tissue when the balloon is expanded. Several embodiments of the balloon form will be introduced below.

Figure 42:
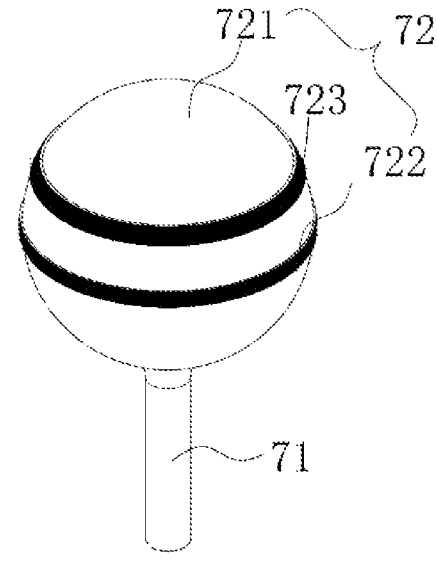
FIG. 42 is a schematic view of an ablation catheter with a distal balloon.
Figure 43:
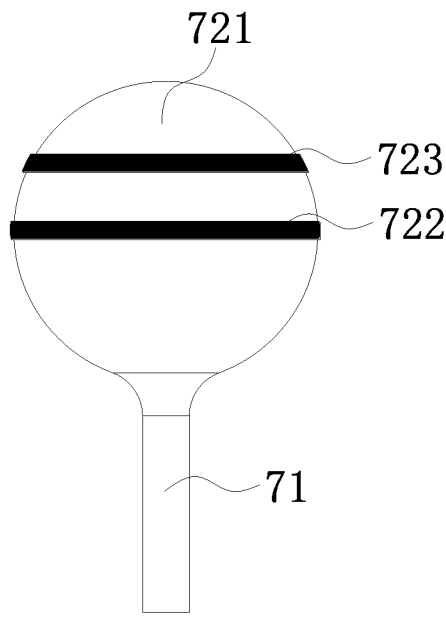
FIG. 43 is a front view of the ablation catheter in FIG. 42.
Figure 44:
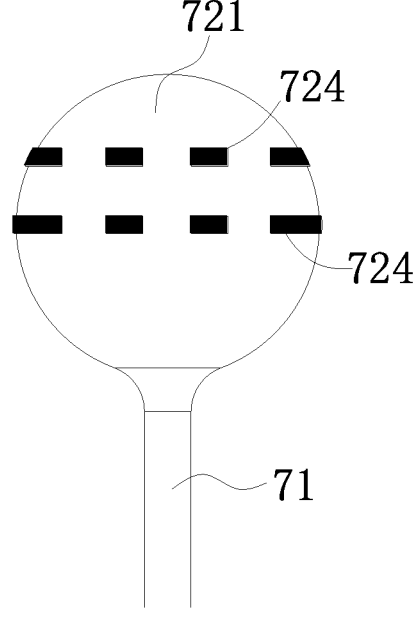
FIG. 44 is a schematic view of another structure of the ablation catheter with a support balloon.

Referring to FIGS. 42 and 43, the ablation catheter includes a sheath 71 and an ablation assembly 72 provided at the distal end of the sheath 71. The ablation assembly 72 includes a support balloon 721 and electrodes provided on the support balloon 721. In this embodiment, the electrodes include a first electrode assembly 722 and a second electrode assembly 723. The first electrode assembly 722 may be formed on the surface of the support balloon 721 adjacent to the equator thereof. For example, the first electrode assembly 722 may be formed adjacent to the equator of the support balloon 721. Herein, the equator of the support balloon 721 refers to the portion with the largest section of the support balloon 721 perpendicular to the axial direction of the sheath 71 when inflated. In this embodiment, the largest section of the support balloon 721 in the axial direction of the sheath 71 is located at the midpoint of the support balloon 721. The second electrode assembly 723 may be formed on the surface of the support balloon 721 distal to the equator, and may be electrically isolated from the first electrode assembly 722. FIGS. 42 and 43 show that the first electrode assembly 722 and the second electrode assembly 723 are continuous in the circumferential direction of the support balloon 721. When pulse energy is applied, the electrode polarities of the first electrode assembly 722 and the second electrode assembly 723 are positive and negative respectively. It would be appreciated that, as shown in FIG. 44, the first electrode assembly 722 and the second electrode assembly 723 may respectively include a plurality of electrodes 724 arranged at intervals in the circumferential direction of the support balloon 721. When pulse energy is applied, the plurality of electrodes 724 of the first electrode assembly 722 may be configured as alternatively spaced positive and negative electrodes, and the plurality of electrodes 724 of the second electrode assembly 723 may be configured as alternatively spaced positive and negative electrodes. In this way, the first electrode assembly 722 can form a first ablation ring, and the second electrode assembly 723 can form a second ablation ring. The diameters of the first ablation ring and the second ablation ring can be different as required, so that the first ablation ring and the second ablation ring can be selected for ablation according to the size of the tissue area, improving the flexibility of the operation.

Figure 45:
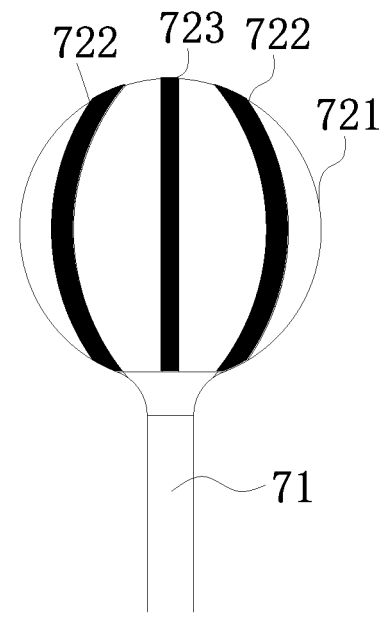
FIG. 45 is a schematic view of another structure of the ablation catheter with a support balloon.

In an alternative embodiment, as shown in FIG. 45, the first electrode assembly 722 and the second electrode assembly 723 can be provided along the axial direction of the sheath 71 or the meridian direction of the support balloon 721, where the meridian direction refers to the direction of the balloon 721 on the surface from the proximal end to the distal end or from the distal end to the proximal end. The first electrode assemblies 722 and the second electrode assemblies 723 are spaced alternately in the circumferential direction. When pulse energy is applied for ablation, the polarities of the first electrode assembly 722 and the second electrode assembly 723 are positive and negative respectively. It will be appreciated that radio frequency energy may be applied for ablation.

Figure 46:
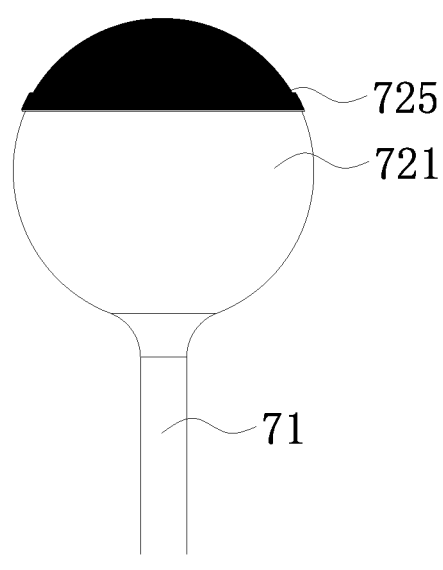
FIG. 46 is a schematic view of another structure of the ablation catheter with a support balloon.

In another alternative embodiment, as shown in FIG. 46, the surface of the spherical cap on the distal side of the equator of the support balloon 721 is completely covered with a layer of electrode 725, that is, the electrode 725 is in a spherical cap form. When pulse energy is applied, the electrode 725 can be a positive electrode, and the negative electrode is placed outside the body, so that focal tissue ablation can be achieved. Alternatively, the electrode 725 can use radio frequency energy.

Figure 47:
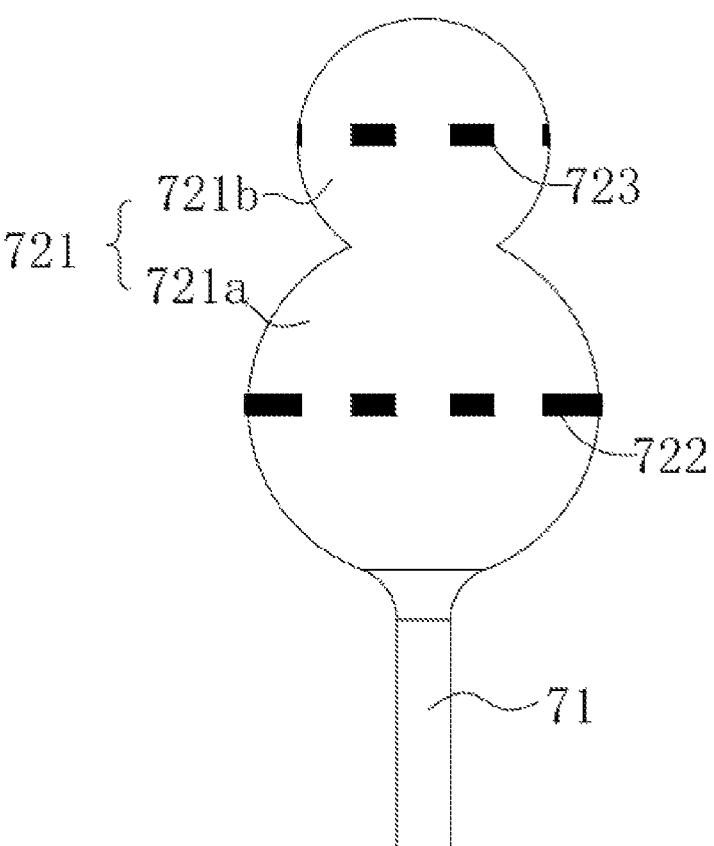
FIG. 47 is a schematic view of another structure of the ablation catheter with a support balloon.

In the embodiment shown in FIGS. 42 to 46, the support balloon 721 is a single balloon structure, and specifically has a spherical shape. In other embodiments, the expanded support balloon 721 is not limited to a spherical shape, and may have other shapes. For example, FIG. 47 shows that the expanded support balloon 721 has a gourd-like configuration. For the convenience of description, the support frame 72 here includes a first balloon 721a and a second balloon 721b. The first balloon 721a is located at the proximal side, and the second balloon 721b is located at the distal side. The diameter of the first balloon 721a is greater than the diameter of the second balloon 721b. The first electrode assembly 722 is provided adjacent to the equator of the first balloon 721a, and the second electrode assembly 723 is provided adjacent to the equator of the second balloon 721b. The definition of the equator refers to the related description of the above embodiment. The first electrode assembly 722 can form a first ablation ring, and the second electrode assembly 723 can form a second ablation ring. In this way, the diameters of the first ablation ring and the second ablation ring can be different as required, so that the first ablation ring and the second ablation ring can be selected for ablation according to the size of the tissue area, improving the flexibility of the operation. Further, in other application scenarios, the second electrode assembly 723 can be used as a mapping electrode.

In the above embodiments, the ablation assembly includes an expandable support frame. In optional embodiments, the ablation assembly may not include an expandable support frame, that is, the ablation assembly may consist of a single or multiple electrodes.

In one embodiment, the distal end of the sheath is provided with electrodes, and these electrodes can be used only as ablation electrodes, or as both ablation electrodes and mapping electrodes. These ablation electrodes form the ablation assembly, that is, the ablation assembly consists of ablation electrodes at the distal end of the sheath. The sheath can reach the lesion tissue by intervention to perform ablation through the ablation electrodes at the distal end of the sheath, or perform mapping through the mapping electrodes at the distal end of the sheath.

Figures 48, 49:
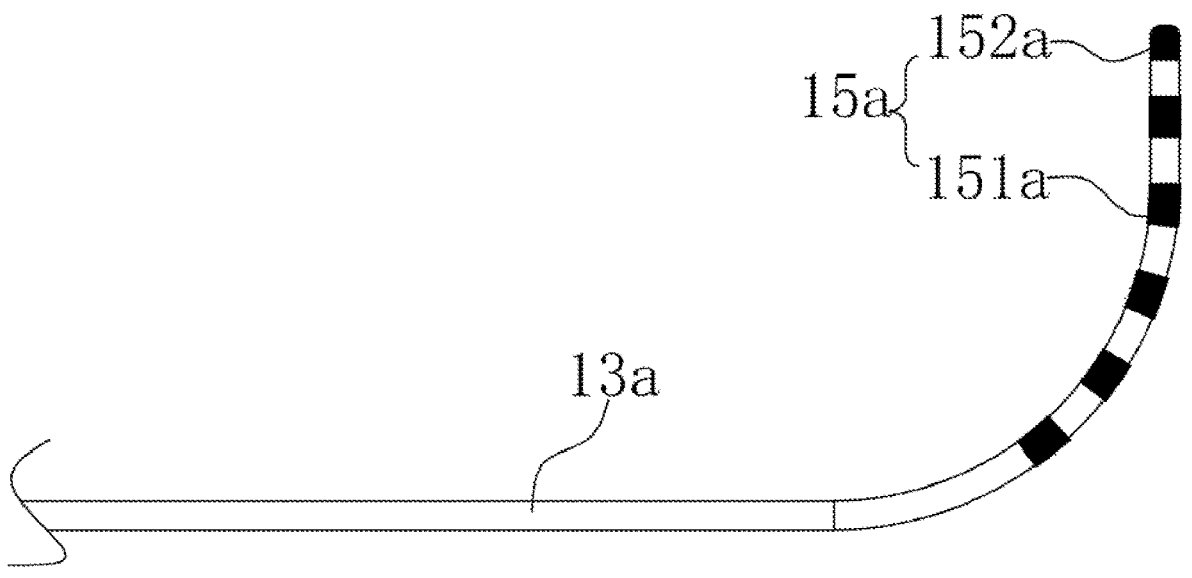
FIG. 48 is a schematic view of an ablation catheter according to another embodiment.
FIG. 49 is a partially enlarged view of the ablation catheter in FIG. 48.

FIG. 48 shows a schematic ablation catheter, and FIG. 49 shows an enlarged view of the distal end of the ablation catheter in FIG. 48. Referring to FIG. 48 and FIG. 49, the ablation catheter includes a sheath 13a and an electrode assembly 15a, and the electrode assembly 15a is provided at the distal end of the sheath 13a. In this embodiment, the electrode assembly 15a includes a first electrode assembly 151a and a second electrode assembly 152a. The first electrode assembly 151a includes a plurality of first electrodes 16a, and the plurality of first electrodes 16a are arranged at intervals at the distal end of the sheath 13a in the axial direction of the sheath 13a. The second electrode assembly 152a includes a plurality of second electrodes 17a, and the plurality of second electrodes 17a are spaced apart from each other in the circumferential direction of the sheath 13a (see FIG. 49). The plurality of second electrodes 17a are arranged at the distal side of the first electrode assembly 151a in the axial direction, and spaced apart from the first electrode assembly 151a. In this embodiment, there are two second electrodes 17a, and the two second electrodes 17a are opposite and spaced apart from each other. The ablation method of this ablation catheter is explained as follows:

The distal end of the sheath 13a has a good flexibility. In the released state, the distal end of the sheath 13a bends and extends radially outward relative to the proximal end. In this embodiment, the sheath 13a is generally L-shaped, and its distal end extends in a strip shape. In case of pulse energy, the plurality of first electrodes 16a of the first electrode assembly 151a can be configured as alternately spaced positive and negative electrodes in the axial direction, and the plurality of second electrodes 17a of the second electrode assembly 152a can be configured as alternately spaced positive and negative electrodes in the circumferential direction. In this way, the operator can operate flexibly as required. Specifically, the first electrode assembly 151a can perform ablation on a large area of lesion tissue (such as the ostium of the pulmonary vein) based on the flexibility of the distal end of the sheath 13a which only needs to be turned multiple times. The ablation area formed by the second electrode assembly 152a is small and the second electrode assembly 152a can be used to perform ablation on the local lesion tissue. In an optional embodiment, the first electrode 16a and the second electrode 17a may use radio frequency energy.

In an optional embodiment, the distal end of the sheath 13a can be bent under the control of the handle (not shown in FIG. 49). The bending angle can be flexibly set and selected, for example, the distal end of the sheath 13a can be bent 360 degrees.

Figure 50:
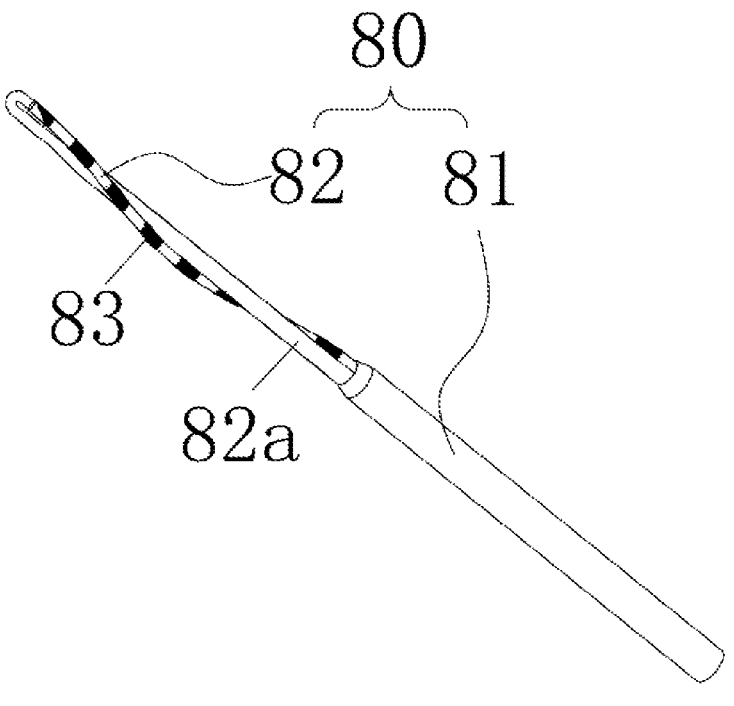
FIG. 50 is a schematic view of an ablation catheter according to an embodiment in which the distal end thereof can be pulled to form a ring structure, with the ablation catheter in a compressed state.
Figure 51:
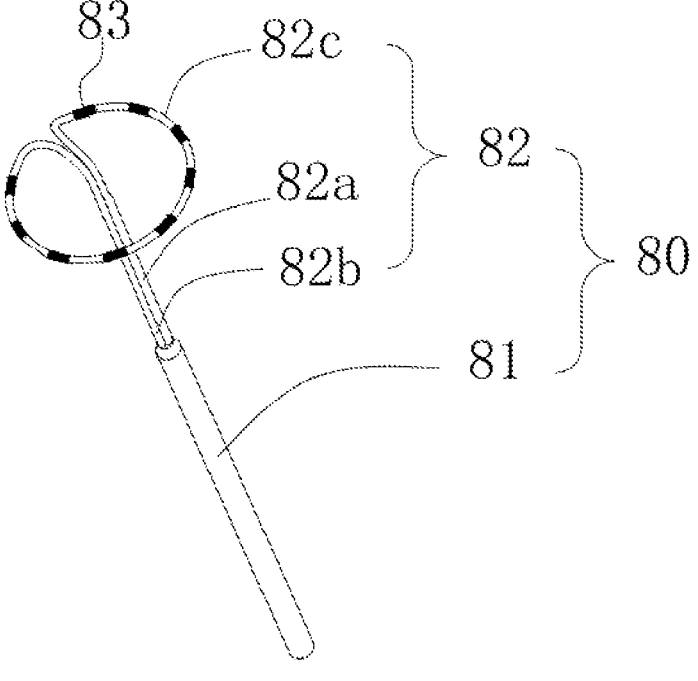
FIG. 51 is a schematic view of the ablation catheter in FIG. 50 in a released state.
Figure 52:
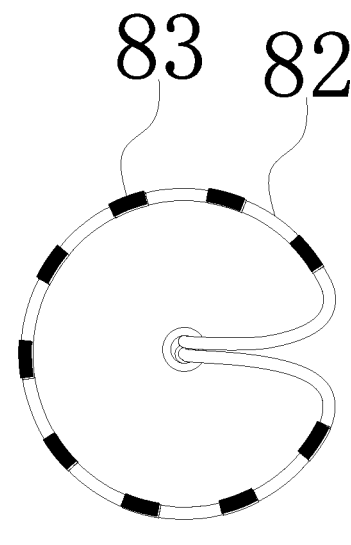
FIG. 52 is a top view of the ablation catheter in FIG. 51.

In one embodiment, referring to FIGS. 50 to 52, the distal end of the sheath can form a ring structure.

Referring to FIG. 50, the sheath 80 includes a first sheath section 81 and a second sheath section 82. The second sheath section 82 is connected to the distal end of the first sheath section 81. The first sheath section 81 is hollow tubular. The second sheath section 82 includes a first connection section 82a, a second connection section 82b and a middle section 82c connected between the two connection sections 82a, 82b. The electrodes 83 are provided on the middle section 82c along its extension direction. In this embodiment, a plurality of electrodes 83 spaced apart from each other are provided on the middle section 82c. The distal ends of the first connection section 82a and the second connection section 82b are respectively connected to two ends of the middle section 82c. The proximal end of the first connection section 82a and the proximal end of the second connection section 82b are connected to the distal end of the first sheath section 81. The first sheath section 81 and the first connection section 82a are configured as relatively rigid portions of the sheath 80. The middle section 82c of the second sheath section 83 is configured as a relatively flexible portion of the sheath 80. The first connection section 82a of the second sheath section 82 is fixedly connected to the distal end of the first sheath section 81, and the second connection section 82b can move toward the proximal side or the distal side in the axial direction of the first sheath section 81. When the second connection section 82b is controlled to move distally to the outside the first sheath section 81, the middle section 82c forms a ring. When the second connection section 82b is pulled proximally, the middle section 82c can be straightened and deformed to extend from the distal end toward the proximal end to twist around or contact the first connection section 82a, thereby reducing the overall radial dimension of the second sheath section 82 (and also the sheath 80), which is very convenient for the intervention and withdrawal of the sheath 80. Moreover, when the middle section 82c of the second sheath section 82 is straightened so as to twist around or contact the first connection section 82a, energy can be applied to the most distal electrode on the middle section 82c, so as to perform focal ablation on the tissue area.

In this embodiment, the ring structure of the second sheath section 82 and the electrodes 83 provided on the ring structure can be regarded as an ablation assembly, which transmits ablation energy to the target tissue area through the electrodes 83. The second connection section 82b of the second sheath section 82 in this embodiment can be regarded as a pulling member for pulling the distal end.

Referring to FIGS. 51 and 52, the proximal end of the second connection section 82b of the second sheath section 82 is released, and the middle section 82c of the second sheath section 82 provided with the electrodes 83 expands radially to form a ring. The electrodes 83 on the second sheath section 82 can be connected with pulse energy or radio frequency energy to form an ablation ring, so as to perform ring-like ablation on the ostium of the pulmonary vein among other tissues. In practice, the ring structure is configured to enter the pulmonary vein or the left atrial appendage and fit with the inner wall of the lumen, so that the axis of the ring structure can be aligned with the center of the ostium of the pulmonary vein or the center of the ostium of the left atrial appendage, facilitating the ablation of the ring structure around the ostium of the pulmonary vein or the ostium of the left atrial appendage. It can be understood that the ablation catheters according to the embodiments of the present disclosure can be used to perform ablation on other tissues in the heart.

It would be appreciated that, in other embodiments, the first connection section 82a of the second sheath section 82 may be removed, that is, the second sheath section 82 consists of a middle section and a connection section, and electrodes are provided on the middle section. One end of the middle section is connected to the distal end of the first sheath section 81, the other end of the middle section is connected to one end of the connection section, and the other end of the connection section is slidably connected to the first sheath section 81. When the connection section of the second sheath section 81 is controlled to move distally, the middle section can deform into a ring. When the connection section is pulled to move proximally, the middle section can be straightened and twist around or contact the upper part of the first sheath section adjacent to the distal end, thereby reducing the overall radial dimension of the sheath 80.

Figure 53:
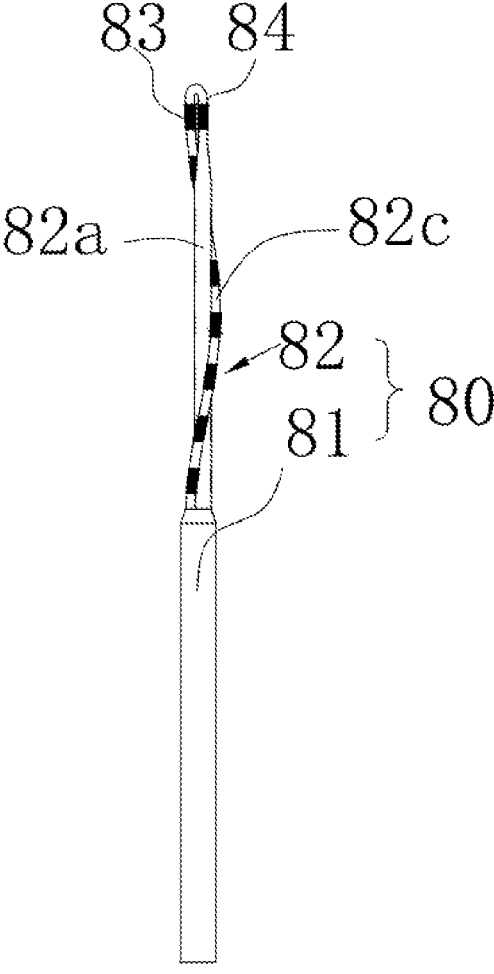
FIG. 53 is a schematic view of an alternative of the ablation catheter in FIG. 50.

In an optional embodiment, as shown in FIG. 53, the distal portion of the first connection section 82a of the second sheath section 81 is also provided with an electrode 84. When the middle section is straightened to twist around or contact the first connection section 82a, the most distal electrode 83 on the middle section 82c is opposite to and electrically isolated from the distal electrode 84 on the first connection section 82a, and the polarities of these two electrodes are positive and negative respectively. Pulse energy can be applied to the two opposite electrodes 83 and

84, so as to provide a strong local ablation at the distal end of the ablation catheter, thereby achieving focal ablation at the local area of the tissue.

It would be appreciated that, in the case where the second sheath section 82 doesn't include the first connection section, the electrode 84 can be provided at the distal end of the first sheath section 81, which will not be described in detail here.

The ring structure formed at the distal end of the sheath 80 can use the following alternatives.

Figure 54:
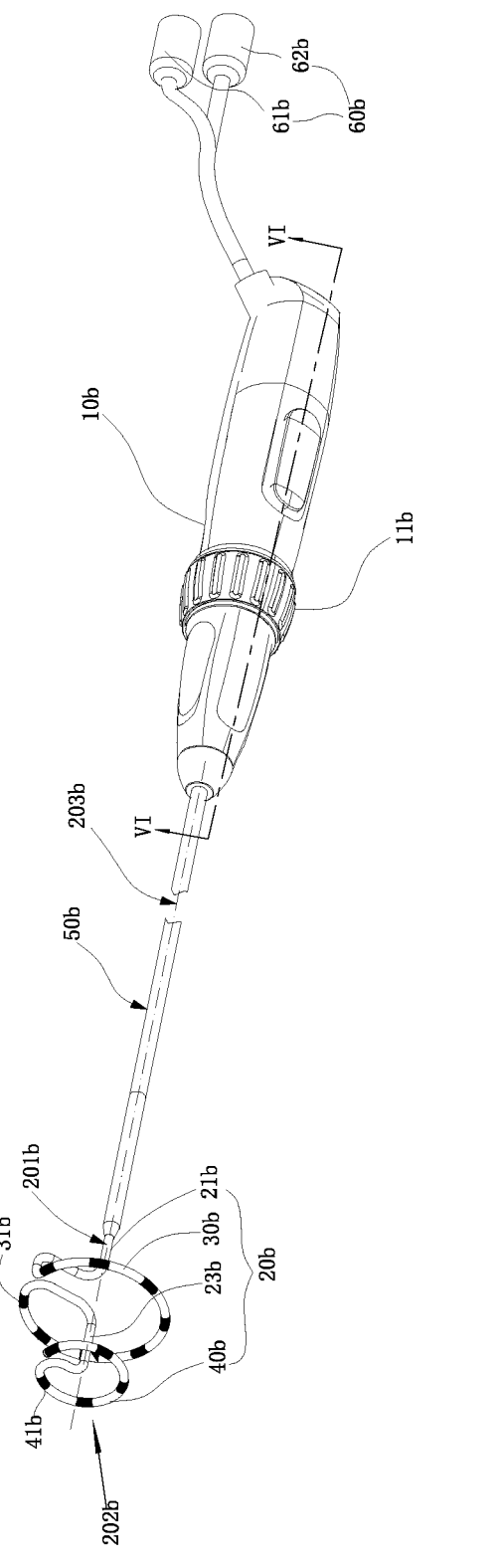
FIG. 54 is a schematic view of an ablation system according to an embodiment.

Referring to FIG. 54, the ablation system according to this embodiment includes a handle 10b, an inner sheath 50b and a bearing strip 20b. The inner sheath 50b and the bearing strip 20b together can be considered as an ablation catheter. The distal end of the handle 10b is fixedly connected to the proximal end of the inner sheath 50b, and the distal end of the inner sheath 50b is fixedly connected to the proximal end 201b of the bearing strip 20b. The distal end 202b of the bearing strip 20b extends in its own axis 203b away from the handle 10b. In this embodiment, the central axis 203b is the central axis of the proximal end of the bearing strip 20b, and coincides with the central axis of the inner sheath 50b as well as the central axis of the handle 10b. In other modified embodiments, the central axis of the bearing strip 20b is not necessarily limited to coincide with the central axis of the inner sheath 50b and the central axis of the handle 10b.

The bearing strip 20b includes a proximal section 21b, the proximal section 21b includes the proximal end 201b, and the proximal section 21b has a rod structure. The distal end 202b of the bearing strip 20b is further provided with a mapping ring 40b and an ablation ring 30b spaced apart from each other, and the ablation ring 30b is located between the mapping ring 40b and the handle 10b. The mapping ring 40b and the ablation ring 30b are both generally ring-shaped, and both of them extend around the axis 203b of the bearing strip 20b. In this embodiment, the central axes of the mapping ring 40b and the ablation ring 30b coincide with each other. In other embodiments, the axes of the mapping ring 40b and the ablation ring 30b may be parallel to each other. In practice, the mapping ring 40b is configured to enter the pulmonary vein or the left atrial appendage, and fit around the inner wall of the lumen so that the axis of the ablation ring 30b is aligned with the center of the ostium of the pulmonary vein or the center of the ostium of the left atrial appendage, facilitating the ablation of the ablation ring 30b around the ostium of the pulmonary vein or the ostium of the left atrial appendage. Another application scenario is that the mapping ring 40b and the ablation ring 30b are configured to perform ablation on the tissue in the ventricle. The following will use pulmonary vein ablation as an example. It would be appreciated that the ablation catheter can be configured to perform ablation on other tissues in the heart.

The mapping ring 40b is provided with mapping electrodes 41b, and the mapping ring 40b detects the electrophysiological signals in the target tissue area through the mapping electrodes 41b for mapping. Specifically, when the mapping ring 40b contacts the target tissue on the inner wall of the pulmonary vein, the ablation catheter can perform intracardiac signal detection with electromyography (EMG) through the mapping electrodes 41b on the mapping ring 40b.

Electrodes 31b are arranged on the ablation ring 30b for transmitting ablation energy to the target tissue area. Since the ablation ring 30b and the mapping ring 40b are axially spaced apart from each other, when the mapping ring 40b contacts the target tissue area, the ablation ring 30b can use the electrodes 31b to emit pulse energy, radio frequency energy or other energy, etc., to perform ablation on the target tissue area.

By detecting the electrophysiological signals in the target tissue area through the mapping ring 40b, the ablation energy for the ablation ring 30b can be controlled, so that the ablation energy emitted by the ablation ring 30b can perform ablation and isolation on at least part of the tissue at the target tissue area. Further, since electrophysiological signals generated by different tissues in the target area are different, and different tissues have different response thresholds to ablation energy, the ablation ring 30b can isolate the target tissue that emits the undesired electrophysiological signals in the target tissue area, thereby avoiding affecting the normal operation of the other tissue. After ablation, the target tissue area generates expected electrophysiological signals, thereby eliminating atrial fibrillation.

In this embodiment, the mapping ring 40b and the ablation ring 30b are formed in one piece, and can perform mapping and ablation on the target tissue simultaneously or separately. Compared with the prior art where ablation and mapping devices are separately controlled for ablation and mapping, the operation is simplified and more convenient, and the success rate of the operation is also improved by the present invention.

In one embodiment, the ring-like mapping ring 40b has a first radial dimension, the ring-like ablation ring 30b has a second radial dimension, and the second radial dimension is greater than or equal to the first radial dimension. In this embodiment, the ablation energy is pulse. The ablation ring 30b can perform ablation on the target tissue in a non-contact manner in the radial direction, and the ablation area formed by the ablation energy is in a ring form along the circumference of the ablation ring 30b and radiates outward. The second radial dimension of the ablation ring 30b being greater than or equal to the first radial dimension of the mapping ring 40b allows the ablation ring 30b to form an ablation area around the ostium of the pulmonary vein, and adapt to the anatomical structure of the ostium of the pulmonary vein.

In this embodiment, the bearing strip 20b includes a proximal section 21b, an ablation ring 30b and a mapping ring 40b arranged in the extension direction of its own axis 203b in sequence, and the ablation ring 30b, the mapping ring 40b and the proximal section 21b are formed in one piece. It would be appreciated that when the ablation ring 30b, the mapping ring 40b and the proximal section 21b are formed in one piece, the distal end 202b of the bearing strip 20b is configured to bend and circle around the axis 203b to form the ablation ring 30b and the mapping ring 40b successively. The bearing strip 20b needs to be delivered and guided by an outer sheath (not shown) surrounding the outer side of the bearing strip 20b to reach the heart. The one-piece bearing strip 20b is linearly accommodated in the outer sheath during delivery, such that it can be compressed to a small profile in its radial dimension, facilitating the delivery in the outer sheath, and allowing the use of an outer sheath with a small diameter. When the bearing strip 20b is released in the heart, it can automatically expand to the configuration shown in FIG. 55, that is, to form the ablation ring 30b and the mapping ring 40b spaced apart from each other for mapping and ablation of the ablation catheter.

Figure 55:
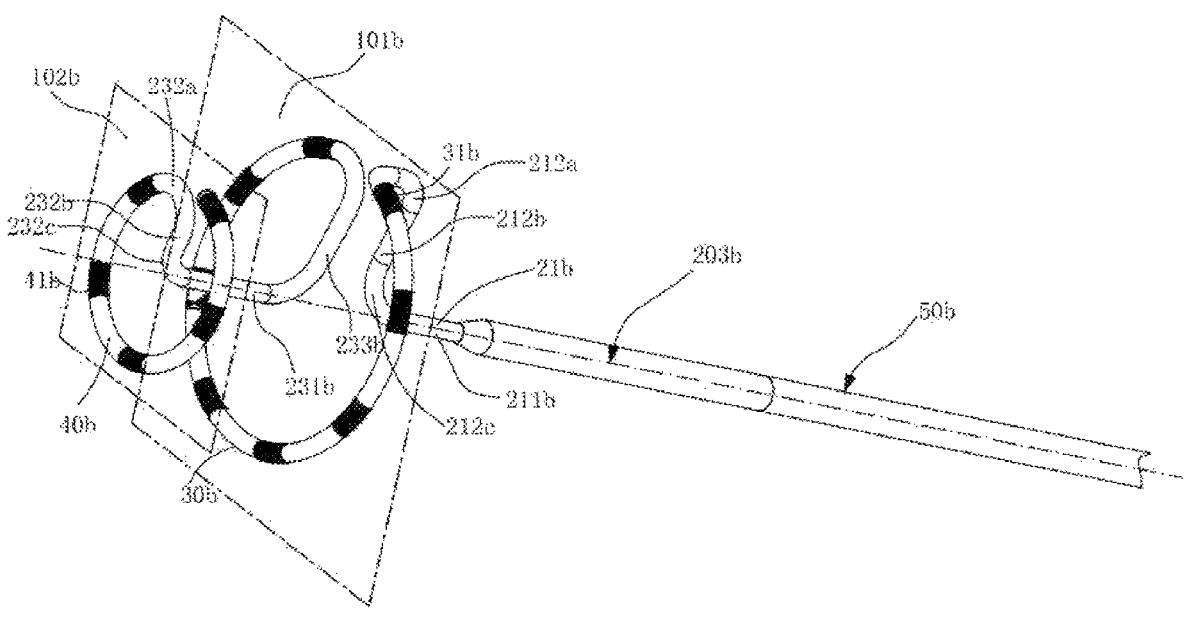
FIG. 55 is a schematic view of the ablation catheter of the ablation system in FIG. 54.

Referring to FIG. 54 and FIG. 55, the bearing strip 20b further includes a connection section 23b connected between the ablation ring 30b and the mapping ring 40b, so as to define a spacing between the ablation ring 30b and the mapping ring 40b. The connection section 23b includes a first section 231b and a second section 232b. The first section 231b is connected to the distal end of the ablation ring 30b, and the second section 232b is connected between the first section 231b and the mapping ring 40b. The second section 232b includes an end 232a connected to the mapping ring 40b and an end 232c connected to the first section 231b, and the end 232c of the second section 232b connected to the first section 231b is closer to the geometric center of the mapping ring 40b than the end 232a connected to the mapping ring 40b.

When the mapping ring 40b enters the pulmonary vein by pushing the handle 10b, the push force from the handle 10b drives the connection section 23b and the mapping ring 40b to move into the pulmonary vein. When the mapping ring 40b abuts against the tissue at the ostium of the pulmonary vein, as the first section 231b is connected to the end 232c of the second section 232b that is closer to the geometric center of the mapping ring 40b, that is, the first section 231b is not connected to the peripheral edge of the mapping ring 40b, the first section 231b will not come into contact with the pulmonary vein, which improves the flexibility of the mapping ring 40b, and the mapping ring 40b can easily and smoothly enter the pulmonary vein. It can be understood that if the first section 231b of the connection section 23b is connected to the peripheral edge of the mapping ring 40b, and when the mapping ring 40b abuts against the tissue at the ostium of the pulmonary vein, the continuous push from the first section 231b to the mapping ring 40b will cause the pushing force to be directly applied to the tissue area, that is, to press the mapping ring 40b against the tissue, and it will be more difficult for the mapping ring 40b to slide into the pulmonary vein.

When a part of the edge of the mapping ring 40b abuts against the tissue at the ostium of the pulmonary vein and the distal end of the first section 231b of the connection section 23b is directed toward the ostium, the mapping ring 40b can enter the pulmonary vein more easily. Further, in the embodiment of FIG. 54, the first section 231b extends along the extension direction of the axis 203b, and when the first section 231b is directed toward the edge of the ostium of the pulmonary vein, the mapping ring 40b can enter the pulmonary vein easily.

In this embodiment, the first section 231b extends axially, and the axis of the first section 231b passes through the geometric centers of the ablation ring 30b and the mapping ring 40b. In a modified embodiment, the geometric center of the ablation ring 30b and the geometric center of the mapping ring 40b are not collinear with the axis 203b. In a modified embodiment, the first section 231b extends parallel to the axis 203b. In other embodiments, the first section 231b is inclined relative to the axial direction. For example, an angle may be defined between the first section 231b and the axis which may be an acute angle or obtuse angle.

The second section 232b extends at least in the radial direction, and the closer the portion on the second section 232b to the proximal end, the closer to the geometric center of the mapping ring 40b. In a modified embodiment, the second section 232b extends both in the axial direction and in the radial direction.

Further, the connection section 23b further includes a third section 233b which is connected between the ablation ring 30b and the first section 231b. Since the first section 231b extends along the axis 203b which passes through the geometric center of the ablation ring 30b, the third section 233b is connected between the geometric center and the edge of the ablation ring 30b. The third section 233b facilitates to maintain the position of the first section 231b relative to the mapping ring 40b and the ablation ring 30b, so that the ablation ring 30b and the mapping ring 40b would not displace easily relative to each other, thereby improving the smoothness of movement and the precision of positioning of the bearing strip 20 after being released in body tissue.

In this embodiment, the third section 233b extends radially, and one end thereof is located at the geometric center of the ablation ring 30b. In a modified embodiment, the third section 233b extends axially and radially, that is, the third section 233b extends both in the axial direction and in the radial direction at a predetermined length, and the third section 233b may not pass through the geometric center of the ablation ring 30b.

As shown in FIG. 55, the proximal section 21b includes a fourth section 211b and a fifth section 212b, and the fourth section 211b is connected between the handle 10b and the fifth section 212b. More specifically, the fourth section 211b is connected between the inner sheath 50b and the fifth section 212b, and the fifth section 212b is connected between the fourth section 211b and the ablation ring 30b. The end 212c of the fifth section 212b connected to the fourth section 211b is closer to the geometric center of the ablation ring 30b than its end 212a connected to the ablation ring 30b.

In the embodiment shown in FIG. 54 and FIG. 55, the fourth section 211b extends along the extension direction of the axis 203b. The fourth section 211b is coaxial with the first section 231b of the connection section 23b and extends along the axis 203b, which allows a uniform force to be applied on the ablation ring 30b and the mapping ring 40b, facilitating the smooth advancement of the ablation ring 30b and the mapping ring 40b, and also reducing the probability of relative deformation between the two rings during the advancement. In a modified embodiment, the fourth section 211b is parallel to the axis 203b, or an angle may be defined between the fourth section 211b and the axis 203b which may be an acute angle or obtuse angle.

In this embodiment, both the ablation ring 30b and the mapping ring 40b have an open-loop structure, which allows the ablation ring 30b, the mapping ring 40b, the connection section 23b and the proximal section 21b to be formed in one piece. In the delivery state, the bearing strip 20b is linearly accommodated in the outer sheath. The one-piece bearing strip 20b does not include joints between the sections of the bearing strip 20b formed by assembling multiple sections, which can reduce the maximum outer diameter of the bearing strip 20b, to allow the use of an outer sheath with a smaller diameter, to facilitate the loading, delivery and withdrawal of the bearing strip 20, and to improve the safety and reliability of the bearing strip 20b. It can be understood that in a modified embodiment, the ablation ring 30b, the mapping ring 40b and the proximal section 21b are not necessarily limited to be formed in one piece, and in the case with the connection section 23b, the ablation ring 30b, the mapping ring 40b, the connection section 23b and the proximal section 21b are not necessarily limited to be formed in one piece either.

In one embodiment, the connection between the proximal section 21b and the ablation ring 30b, the connection between the connection section 23b and the ablation ring 30b, and the connection between the connection section 23b and the mapping ring 40b respectively are configured as circular arc transitions. The connections of circular arc transitions can reduce stress concentration on the one-piece bearing strip 20b at the turning portions, avoid cracks or breakage of the bearing strip 20b when the bearing strip 20b is bent to form the ablation ring 30b and the mapping ring 40b, and also reduce the risk of the bearing strip 20b scratching and puncturing the tissue. Correspondingly, that is, the connection between the first section 231b and the second section 232b, and the connection between the first section 231b and the third section 233b within the connection section 23b, as well as the connection between the fourth section 211b and the fifth section 212b within the proximal section 21b can also be configured as circular arc transitions.

Referring to FIG. 55, a schematic view of the mapping ring 40b and the ablation ring 30b according to this embodiment is shown. As shown in FIG. 55, the ring-like ablation ring 30b is defined in a first plane 101b to facilitate the formation of a ring-like ablation area at the ostium of the pulmonary vein. The ring-like mapping ring 40b is defined in a second plane 102b to facilitate the mapping ring 40b to enter the pulmonary vein and abut against the inner wall of the pulmonary vein, thereby positioning the ablation ring 30b at the ostium of the pulmonary vein in alignment with the center of the pulmonary vein. The first plane 101b is perpendicular to the axis 203b of the bearing strip 20b, and the second plane 102b is perpendicular to the axis 203b of the bearing strip 20b. In a modified embodiment, the first plane 101b or the second plane 102b is perpendicular to the axis 203b of the bearing strip 20b. In another modified embodiment, the first plane 101b and the second plane 102b are not parallel to each other, and/or the first plane 101b or the second plane 102b is not perpendicular to the axis 203b.

In the present embodiment, the first plane 101b is parallel to the second plane 102b, so that the distances between any portions on the ablation ring 30b and the corresponding portions on the mapping ring 40b are equal, that is, the distances between the intersections of any planes perpendicular to the first plane 101b and the second plane 102b with the ablation ring 30b and the mapping ring 40b are equal, which facilitates the control of the ablation energy output by the ablation ring 30b according to the detection result of the mapping ring 40b. Both the first plane 101b and the second plane 102b being perpendicular to the axis 203b of the bearing strip 20b facilitates the positioning of the mapping ring 40b and the ablation ring 30b by the handle 10b during the operation.

In other embodiments, it is not necessarily limited to configure the ring-like ablation ring 30b to be defined in the first plane 101b, the ring-like mapping ring 40b to be defined in the second plane 102b, the first plane 101b to be perpendicular to the axis 203b of the bearing strip 20b, and the second plane 102b to be perpendicular to the axis 203b of the bearing strip 20b.

Referring further to FIG. 55, there are a plurality of mapping electrodes 41b on the mapping ring 40b which are arranged at intervals in the circumferential direction of the mapping ring 40b. Preferably, the mapping electrodes 41b are arranged at regular intervals in the circumference of the mapping ring 40b. The plurality of mapping electrodes 41b can collect electrophysiological signals from the target tissue area from multiple directions, to quickly and accurately position the lesion.

Similarly, a plurality of electrodes 31b are arranged at intervals in the circumferential direction of the ablation ring 30b. Preferably, the electrodes 31b are arranged at regular intervals in the circumference of the ablation ring 30b. The plurality of electrodes 31b can emit ablation energy from multiple directions so that the ablation energy emitted from the ablation ring 30b is in a ring form, which can effectively acts on the target tissue area to isolate the lesion.

In the present embodiment, pulse energy is applied for ablation. Pulse ablation utilizes a high-intensity pulsed electric field to cause irreversible electrical breakdown of the cell membrane, which is so called irreversible electroporation in the medical field, causing cell apoptosis and thus achieving non-thermal ablation of cells, without heat sink effect. The high-voltage pulse sequence generates less heat and does not need saline irrigation for cooling, which can effectively reduce the occurrence of gas explosion, eschar and thrombus. The treatment time for pulse ablation is short. The treatment time of applying a set of pulse sequences is less than 1 minute, and the whole ablation time is generally no more than 5 minutes. Moreover, since different tissues have different response thresholds to a pulsed electric field, it is possible to perform ablation on the myocardium without disturbing other surrounding tissues, thereby avoiding accidentally injuring the esophagus and phrenic nerve tissues adjacent to the pulmonary vein.

In addition, pulse ablation does not require heat conduction to perform ablation on deep tissue, and all cardiomyocytes distributed in the pulsed electric field with a certain electric intensity emitted by the ablation ring 30b will suffer from electroporation, which reduces the requirements for the contact pressure of the ablation catheter with target tissue during ablation. Therefore, after the ablation device according to this embodiment enters the atrium, it is not necessary for the ablation ring 30b to completely contact the inner wall of the target tissue. After ablation, the intracardiac electrophysiological signals can be monitored in time through the mapping ring 40b to determine whether the target tissue has been completely electrically isolated.

For the ablation catheter using pulse energy, the electrodes 31b arranged on the ablation ring 30b need to be configured as alternative positive and negative electrodes, so as to provide a closed-loop lesion area through the pulse energy by the electrodes 31b.

Figure 56:
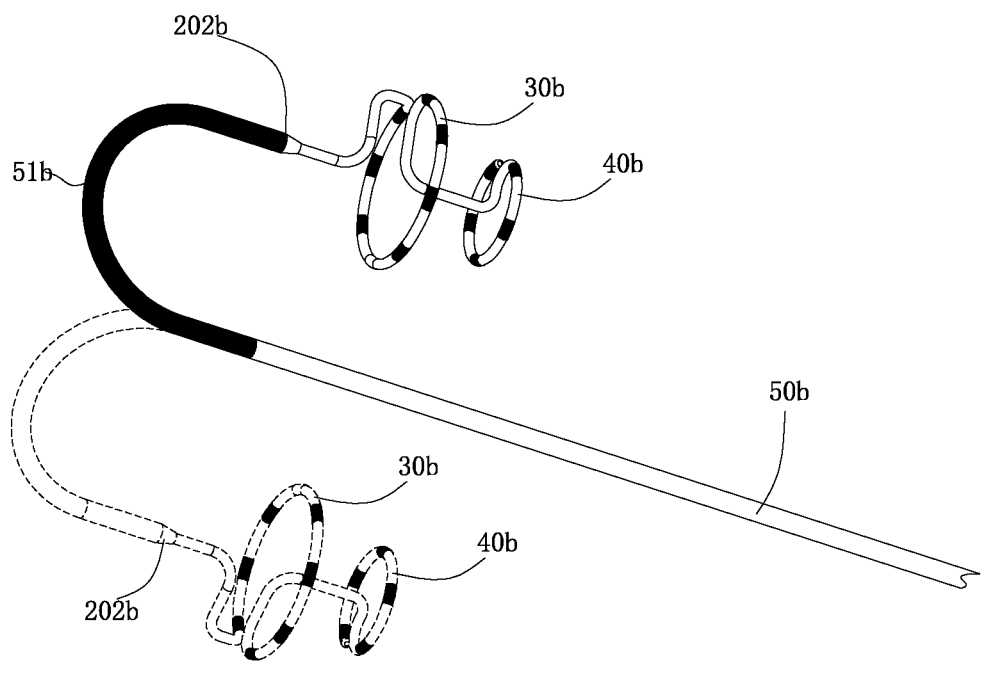
FIG. 56 is a schematic view of the ablation catheter shown in FIG. 55 after being bent.
Figure 57:
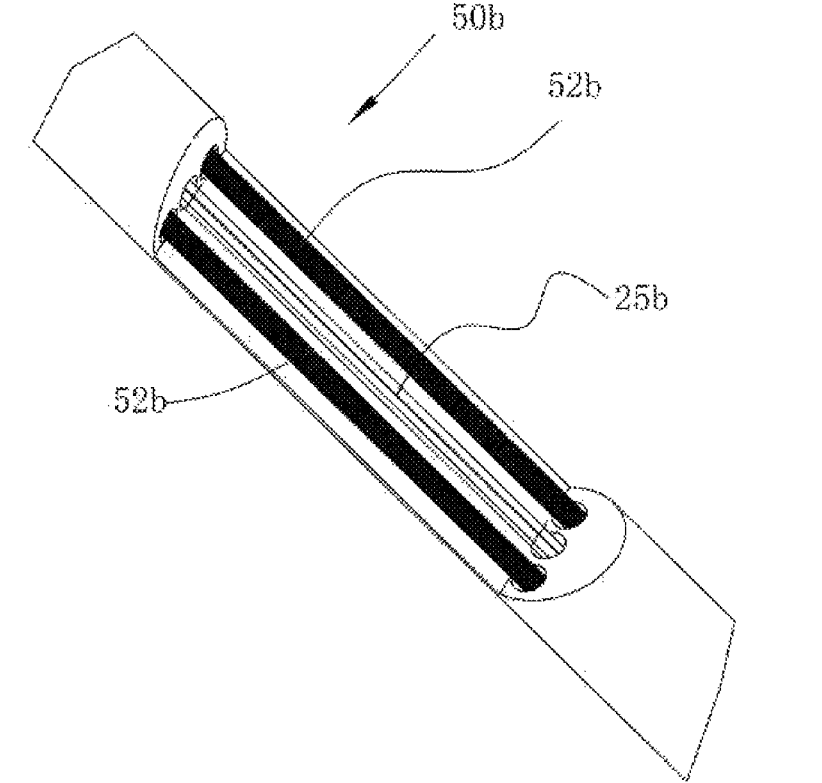
FIG. 57 is a schematic view of the internal structure of the inner sheath shown in FIG. 56.

Referring to FIG. 56 and FIG. 57, the inner sheath 50b of the ablation device according to another embodiment of the present disclosure is hollow tubular. The distal end 202b of the inner sheath 50b is provided with a bendable section 51b, and the bending degree of the bendable section 51b can be adjusted. The bendable section 51b is made of flexible material, and the hardness of the bendable section 51b is smaller than that of the other section of the inner sheath 50b, so as to facilitate the bending operation. The bendable section 51b allows to accurately control the specific portion of the inner sheath 50b to be deformed during the bending process, and avoids relative deformation between the mapping ring 40b and the ablation ring 30b affecting the ablation effect of the ablation catheter.

At least one guide member 52b is provided within the tube wall of the inner sheath 50b along the extension direction of the axis 203b. Two ends of the guide member 52b are respectively connected to the distal end of the bendable section 51b and the handle 10b. The guide member 52b is fixedly connected with the distal end of the bendable section 51b, and the handle 10b is provided with an adjustment knob 11b (FIG. 59) which is connected with the guide member 52b and can pull the guide member 52b. The at least one guide member 52b can be tensioned by rotating the adjustment knob 11b relative to the handle 10b, so as to make the bendable section 51b bend in one direction (as shown in FIG. 56). The bending angle of the bendable section 51b can be changed by controlling the rotation angle of the adjustment knob 11b. The bent inner sheath 50b can adjust the orientations of the mapping ring 40b and the ablation ring 30b, so that the mapping ring 40b can be directed into the target lumen, and the ablation ring 30b can contact the target tissue area for mapping and ablation.

Figure 58:
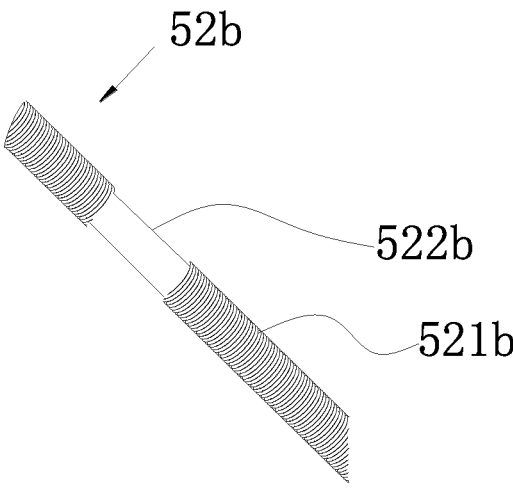
FIG. 58 is a schematic view of the internal structure of the guide member shown in FIG. 57.

Further, referring to FIG. 58, the guide member 52b includes a guide tube 521b and a guide wire 522b. The guide tube 521b is hollow tubular, and the lumen therein is used for the guide wire 522b passing through. The two ends of the guide wire 522b are connected the distal end of the bendable section 51b and the handle 10b respectively. The guide wire 522b may be a stainless steel wire. In one embodiment, the guide wire 522b is a coated stainless steel wire with a smooth surface and good controllability. The guide tube 521b may be a spring coil covering the stainless steel wire, which facilitates a smooth bending of the inner sheath 50b.

In one embodiment, the guide member 52b doesn't include the guide tube 521b, that is, the guide member 52b is a guide wire.

In the present embodiment, two guide members 52b are oppositely arranged in the tube wall of the inner sheath 50b, and the two guide members 52b are pulled by the rotation of the adjustment knob 11b (FIG. 59) to control the bendable section 51b to bend in opposite directions (FIG. 56). Such arrangement allows the distal end of the ablation catheter to flexibly turn in two directions, improving the operability and convenience of the ablation catheter. It can be understood that the number of guide members 52b can be more than two, so that the bendable section 51b of the inner sheath 50b can be bent in multiple directions.

Figure 59:
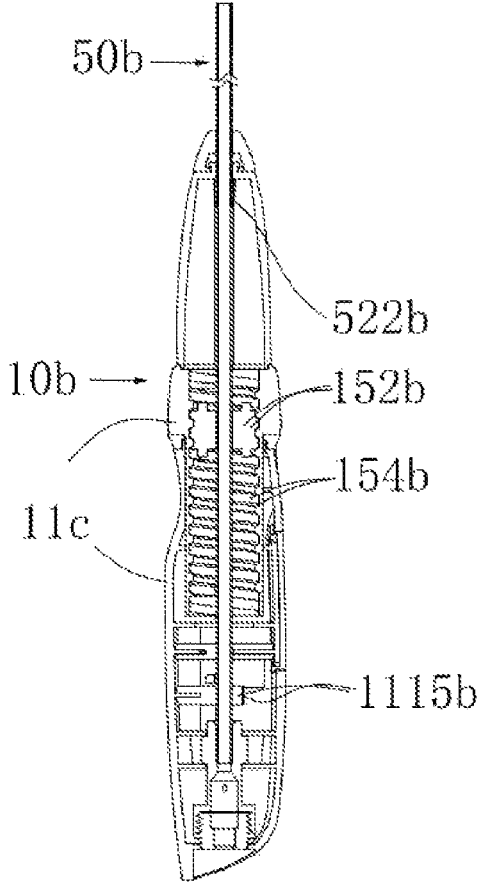
FIG. 59 is a sectional view of the handle shown in FIG. 54 along line VI-VI.

Referring to FIG. 59, the handle 10b includes a housing 11c, an adjustment member 152b provided in the housing 11c, and a driving member 154b for driving the adjustment member 152b to move in the axial direction of the inner sheath 50b. The two guide wires 522b are slidably arranged within the tube wall of the inner sheath 50b in the axial direction of the inner sheath 50b. A wire winding portion 1115b is fixedly provided in the housing 11c. Preferably, the wire winding portion 1115b is adjacent to the proximal end of the adjustment member 152b. The distal ends of the two guide wires 522b are connected to the distal end of the bendable section 51b (FIG. 56). The proximal end of one of the guide wires 522b is connected to the adjustment member 152b, and the proximal end of the other guide wire 522b is wound around the wire winding portion 1115b and then connected to the adjustment member 152b. Specifically, the distal end of one of the guide wires 522b is fixed to the distal end of the bendable section 51b, and the proximal end thereof is directly connected to the adjustment member 152b. The distal end of the other guide wire 522b is fixed to the distal end of the bendable section 51b, and the proximal end thereof is connected to the adjustment member 152b after being wound around the wire winding portion 1115b.

The outer wall of the driving member 154b is fixedly connected to the adjustment knob 11c in the circumferential direction, and the rotation of the adjustment knob 11c drives the rotation of the driving member 154b. The rotating driving member 154b, through its female thread, drives the adjustment member 152b to move and thus drives the two guide wires 522b to slide, so that the bendable section 51b of the sheath 23b can be bent in different directions. The bendable section 51b can be bent in different directions and resiliently return to its initial position.

When bending the inner sheath 50b, the driving member 154b is rotated by operating the adjustment knob 11c, so as to drive the adjustment member 152b to rotate proximally or distally and move axially. In the initial state, when the adjustment member 152b rotates proximally and moves axially, the guide wire 522b directly fixed to the adjustment member 152b is driven to slide proximally, so that the bendable section 51*b* bends towards the pulled guide wire 522*b*, and during the bending process of the bendable section 51*b*, the guide wire 522*b* connected to the adjustment member 252*b* after being wound around the wire winding portion 1115*b* is pulled to slide distally by the deformed bendable section 51*b*, thereby completing the bending of the bendable section 51*b*. In the initial state, when the adjustment member 152*b* rotates distally and moves axially, the guide wire 522*b* connected to the adjustment member 152*b* after being wound around the wire winding portion 1115*b* is driven by the adjustment member 152*b* to slide proximally, so that the bendable section 51*b* bends toward the pulled guide wire 522*b*, and during the bending process, the bendable section 51*b* will drive the guide wire 522*b* directly fixed to the adjustment member 152*b* to slide distally, thereby completing the bending of the bendable section 51*b*.

It should be noted that the initial state refers to the state in which the bendable section 51*b* of the inner sheath 50*b* is straightened.

Referring to FIG. 54 again, the ablation system according to this embodiment further includes a connector 60*b* connected to the handle 10*b*. In this embodiment, the connector 60*b* is connected to the proximal end of the handle 10*b*, and the connector 60*b* includes a detection interface 61*b* and an energy supply interface 62*b*. The detection interface 61*b* is electrically connected to the mapping electrodes 41*b* on the mapping ring 40*b*, and is used for receiving the electrophysiological signals detected by the mapping ring 40*b*. The energy supply interface 62*b* is electrically connected to the electrodes 31*b* on the ablation ring 30*b*, and is used for transmitting external energy to the ablation ring 30*b* for ablation. The energy supply interface 62*b* is used to connect external pulse energy, radio frequency energy or microwave energy.

The inner sheath 50*b* is hollow tubular, and a plurality of conducting wires 24*b* insulated from each other are arranged therein. The detection interface 61*b* is connected to the plurality of mapping electrodes 41*b* distributed on the mapping ring 40*b* through the conducting wires 24*b*, and the electrophysiological signals detected by the mapping electrode s41*b* are transmitted to the detection interface 61*b* through the respective conducting wires 24*b* and then transmitted to an external detection instrument through the detection interface 61*b*. The energy supply interface 62*b* is connected to the plurality of electrodes 31*b* distributed on the ablation ring 30*b* through the conducting wires 24*b* different from the conducting wires 24*b* for the detection interface 61*b*. The energy supply interface 62*b* receives external energy and transmits it to the electrodes 31*b*, so that the electrodes 31*b* can, based on the external energy, provide ablation energy acting on the target tissue area.

Figure 60:
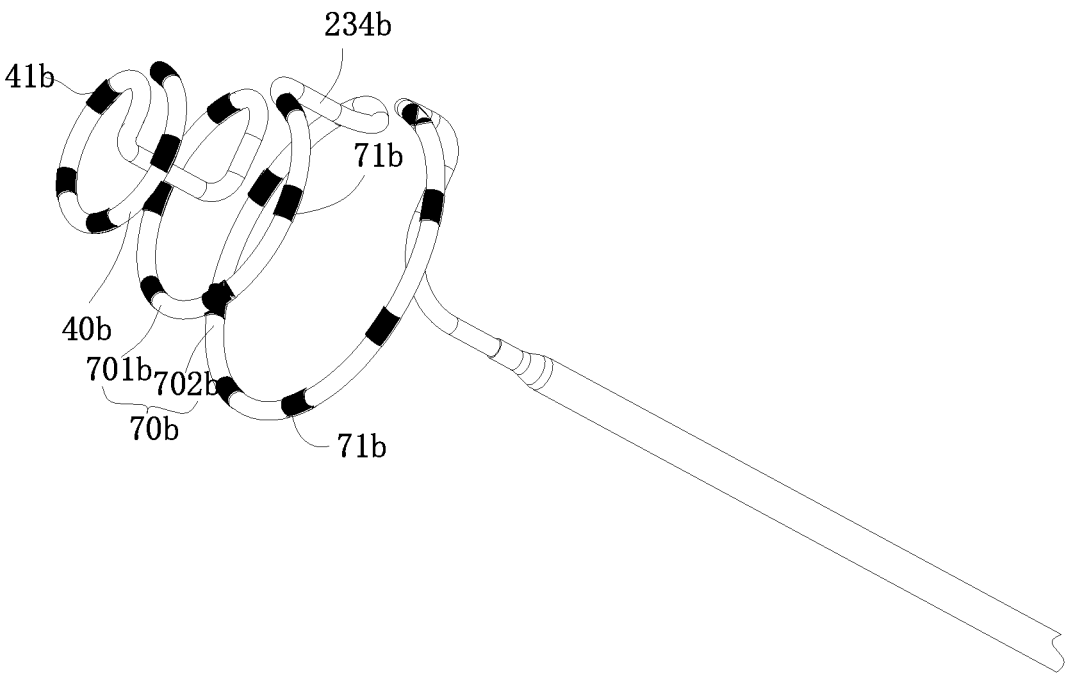
FIG. 60 is a schematic view of an ablation system according to another embodiment.

Referring to FIG. 60, the ablation ring 70*b* according to another embodiment of the present disclosure mainly differs from the ablation ring in the previous embodiment in that the ablation ring 70*b* includes two sub-ablation rings, which are respectively the first ablation ring 701*b* and the second ablation ring 702*b*, and the first ablation ring 701*b* is provided between the second ablation ring 702*b* and the mapping ring 40*b*.

The first ablation ring 701*b* and the second ablation ring 702*b* are respectively provided with a plurality of spaced electrodes 71*b*, and both the first ablation ring 701*b* and the second ablation ring 702*b* can emit ablation energy.

It would be appreciated that the range of ablation energy formed when the first ablation ring 701*b* works alone is different from the range of ablation energy formed when the second ablation ring 702*b* works alone, so the ablation catheter of the present disclosure can provide ablation ranges of different sizes and covering larger areas through the two spaced sub-ablation rings. Moreover, based on the abnormal electrophysiological signals from respective target tissue area detected by the mapping ring 40*b*, the ablation catheter of the present disclosure can control respective sub-ablation ring to emit ablation energy acting on the respective target tissue area for electrophysiological isolation, or control the two sub-ablation rings to emit ablation energy at the same time, to provide higher ablation energy and shorten the operation time. It can be understood that, in other embodiments, the number of sub-ablation rings of the ablation catheter may be more than two, so as to further enlarge the action range of the ablation ring 70*b*. In one embodiment, some electrodes 71*b* on the first ablation ring 701*b* and some electrodes on the second ablation ring 702*b* are powered on at the same time, so as to perform ablation on a given area.

In the embodiment shown in FIG. 60, the radial dimension of the second ablation ring 702*b* is greater than the radial dimension of the first ablation ring 701*b*. The radial dimensions of the two sub-ablation rings are different and thus the action ranges of the generated ablation energy are also different. The smaller the radial dimension of the sub-ablation ring closer to the mapping ring 40*b*, the smaller the radial dimension of the distal ring of the ablation catheter in this embodiment. Depending on the diameter of the target vascular tissue, the first ablation ring 701*b* or the second ablation ring 702*b* can be selected for ablation. For example, when the patient's pulmonary vein is small, the electrodes 71*b* on the first ablation ring 701*b* can be powered on and the electrodes on the second ablation ring 702*b* 71*b* can be powered off, that is, only the first ablation ring 701*b* contacts the ostium of the pulmonary vein for ablation; when the patient's pulmonary vein is large, the first ablation ring 701*b* can enter the interior of the pulmonary vein, the electrodes 71*b* on the second ablation ring 702*b* can be powered on, and the electrodes 71*b* on the first ablation ring 701*b* can be powered off, that is, only the second ablation ring 702*b* contacts the ostium of the pulmonary vein for ablation, thereby improving the closeness with the target tissue and the ablation effect.

In case of pulse ablation, the electrodes on the first ablation ring and the electrodes on the second ablation ring have different polarities, that is, one positive and the other negative. In practice, the diameters of the first ablation ring and the second ablation ring can be equal.

Specifically, the bearing strip is provided with a sixth section 234*b* between the first ablation ring 701*b* and the second ablation ring 702*b*, and the sixth section 234*b* can be arranged parallel to or coincident with the axis, or with an acute angle or obtuse angle relative to the axis. The two ends of the sixth section 234*b* can be further provided with other connection sections for connecting the first ablation ring 701*b* and the second ablation ring 702*b*, so that the sixth section 234*b* can push the first ablation ring 701*b* and the mapping ring 40*b* to move into the vein.

Other embodiments in which the distal end of the ablation catheter has a ring structure are also possible, which are different from the above embodiments in which the two rings are formed at the distal end of the same ablation catheter (also the same sheath).

Figure 61:
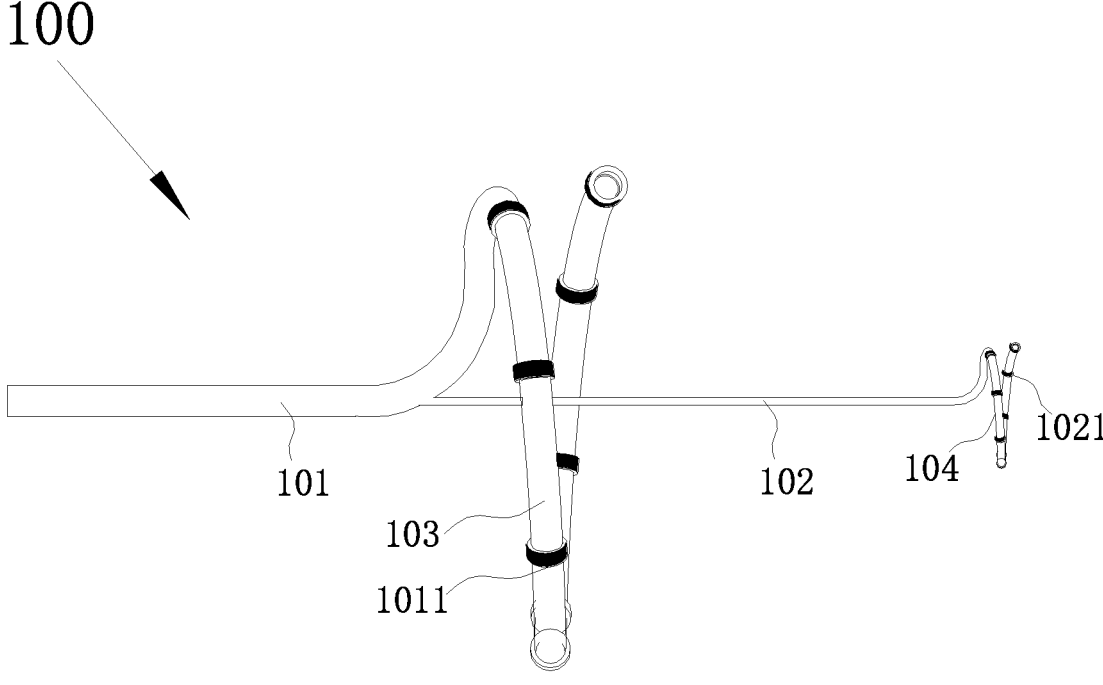
FIG. 61 is a schematic view of an ablation device according to another embodiment.

For example, as shown in FIG. 61, in this embodiment, there are two ablation catheters 100, i.e., the first catheter 101 and the second catheter 102. The lumen of the first catheter 101 is used for the second catheter 102 passing through. A first ring structure 103 is formed at the distal end of the first catheter 101, and a second ring structure 104 is formed at the distal end of the second catheter 102. In use, the first ring structure 103 can be used as an ablation ring, and the second ring structure 104 can be used as a mapping ring. Specifically, a plurality of electrodes 1011 are provided on the first ring structure 103, and the plurality of electrodes 1011 are arranged on the first ring structure 103 at intervals in the circumferential direction of the first ring structure 103. Preferably, the plurality of electrodes 1011 are arranged at regular intervals in the circumferential direction. The plurality of electrodes 1011 can emit ablation energy from multiple directions so that the ablation energy emitted from the first ring structure 103 is in a ring form, which can effectively act on the target tissue area to isolate the lesion.

The first ring structure 103 can be retracted into the outer tube (not shown in FIG. 61) connected to the distal end of the handle (not shown in FIG. 61) to be straightened, and the second ring structure 104 can be retracted into the lumen of the first catheter 101 to be straightened, so as to facilitate the delivery and withdrawal.

A plurality of electrodes 1021 are provided on the second ring structure 104, and the plurality of electrodes 1021 are arranged at intervals in the circumferential direction of the second ring structure 104. Preferably, the plurality of electrodes 1021 are arranged at regular intervals in the circumferential direction.

The radial dimension of the second ring structure 104 is smaller than the radial dimension of the first ring structure 103 so that when the electrodes 1011 on the first ring structure 103 are used to perform ablation on the tissue around the ostium of the pulmonary vein, the electrodes 1021 on the second ring structure 104 can perform intracardiac signal detection with electromyography (EMG). In addition, it should be noted that the second catheter 102 is inserted in the first catheter 101 so that the second catheter 102 and the first catheter 101 can move relative to each other in the axial direction to adjust the axial distance between the first ring structure 103 and the second ring structure 104 and thus the relative axial distance between the ablation ring and the mapping ring.

In the present embodiment, pulse energy is applied for ablation. Pulse ablation utilizes a high-intensity pulsed electric field to cause irreversible electrical breakdown of the cell membrane, which is so called irreversible electroporation in the medical field, causing cell apoptosis and thus achieving non-thermal ablation of cells, without heat sink effect. The high-voltage pulse sequence generates less heat and does not need saline irrigation for cooling, which can effectively reduce the occurrence of gas explosion, eschar and thrombus. The treatment time for pulse ablation is short. The treatment time of applying a set of pulse sequences is less than 1 minute, and the whole ablation time is generally no more than 5 minutes. Moreover, since different tissues have different response thresholds to a pulsed electric field, it is possible to perform ablation on the myocardium without disturbing other surrounding tissues, thereby avoiding accidentally injuring the esophagus and phrenic nerve tissues adjacent to the pulmonary vein.

In addition, pulse ablation does not require heat conduction to perform ablation on deep tissue, and all cardiomyocytes distributed in the pulsed electric field with a certain electric intensity emitted by the ablation ring will suffer from electroporation, which reduces the requirements for the contact pressure of the ablation catheter with target tissue during ablation. Therefore, after the ablation device according to this embodiment enters the atrium, it is not necessary for the ablation ring to completely contact the inner wall of the target tissue. After ablation, the intracardiac electrophysiological signals can be monitored in time through the mapping ring to determine whether the target tissue has been completely electrically isolated.

For the ablation catheter using pulse energy, the electrodes 1011 arranged on the ablation ring need to be configured as alternative positive and negative electrodes, so as to provide a closed-loop lesion area through the pulse energy by the electrodes 1011.

In another optional embodiment, the radial dimensions of the first ring structure 103 and the second ring structure 104 are not limited, which can be the same or different. Moreover, the mapping ring is not necessarily limited to be used only for mapping, and the electrodes on the mapping ring can also be used as ablation electrodes. In an optional embodiment, the electrodes 1011 on the first ring structure 103 are all of the same polarity, the electrodes 1021 on the second ring structure 104 are all of the same polarity, and the polarities of the electrodes on the two ring structures 103, 104 are opposite so that an electric field for ablation can be generated between the first ring structure 103 and the second ring structure 104. Without adjusting the pulse current intensity, the ablation intensity can be adjusted by changing the axial distance between the first ring structure 103 and the second ring structure 104, so as to meet the critical thresholds of signal blocking for different tissues in pulse ablation.

Figure 62:
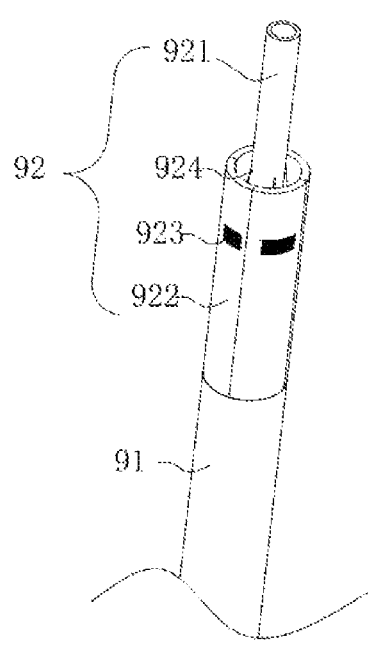
FIG. 62 is a schematic view of the expandable and compressible distal end of the ablation catheter according to an embodiment, with the ablation catheter in the compressed state.
Figure 63:
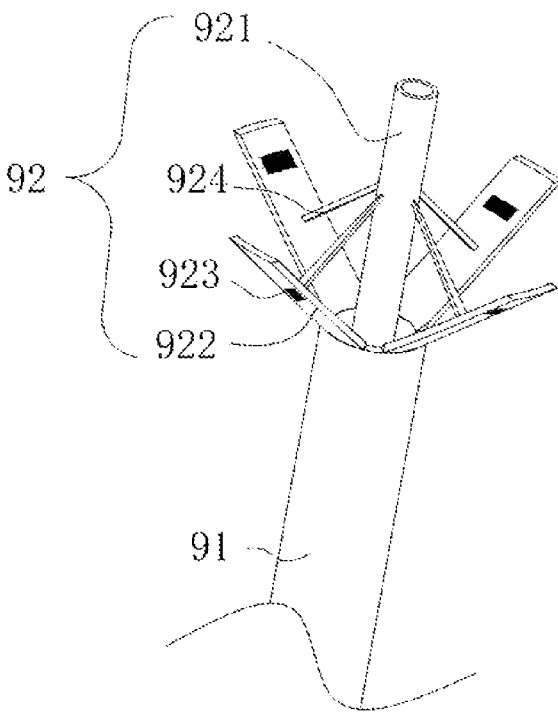
FIG. 63 is a schematic view of the ablation catheter in FIG. 62 in a compressed state.

In an optional embodiment, as shown in FIG. 62 and FIG. 63, the ablation catheter includes a sheath 91 and an ablation assembly 92 provided at the distal end of the sheath 91. The ablation assembly 92 is switchable between a compressed state and an expanded state. FIG. 62 is a schematic view of the ablation assembly 92 in a compressed state, and FIG. 63 is a schematic view of the ablation assembly 92 in an expanded state. The ablation assembly 92 in the compressed state can be used for focal ablation, and the ablation assembly 92 in the expanded state can be used for ring-like ablation.

Specifically, the ablation assembly 92 includes a driving member 921, a plurality of support sheets 922 provided around the axis of the sheath 91, and electrodes 923 provided at the distal ends of the support sheets 922. The driving member 921 can drive the support sheets 922 to switch between the compressed state and the expanded state. In the compressed state, the lumen formed by the plurality of support sheets 922 communicates with the lumen of the sheath 91. In the expanded state, the distal ends of the plurality of support sheets 922 radially expand outward to form an umbrella-like structure with the proximal end of which connected to the distal end of the sheath 91. In this embodiment, the driving member can be configured as an inner tube, and the lumen of the inner tube can be used for the guide wire of the ablation system passing through, so as to establish an intervention access through the guide wire during intervention.

In this embodiment, a rotatable arm 924 is hinged between the driving member 921 and each support sheet 922. During the back-and-forth movement of the driving member 921 in the axial direction of the sheath 91, the support sheets 922 are expanded or compressed by the driving member 921 through the rotatable arms 924, so that the electrodes 923 on the support sheets 922 can perform focal ablation and ring-like ablation at the ostia of the pulmonary vein and left atrial appendage among others.

In an optional embodiment, in order to allow the support sheets 922 to rotate relative to the sheath 91 so as to expand radially, the proximal ends of the support sheets 922 and the distal end of the sheath 91 can be connected by elastic elements, for example, elastic rubbers or springs, which tend to pull the support sheets 922 to be compressed radially.

The outer tube, i.e., the most outer sheath connected to the handle, of the ablation device in the various embodiments of the present disclosure can be bendable. In one embodiment, the handle is provided with a bending module. The bending module includes a slide and an actuator. A pulling element is disposed in the side wall of the outer tube, one end of the pulling element is connected to the distal end of the outer tube, and the other end of the pulling element is connected to the slide. The actuator is used to drive the slide to slide axially to bend the distal end of the outer tube. By providing a bendable distal end for the outer tube in the various embodiments of the present disclosure, the ablation assembly at the distal end of the ablation device can be positioned at the lesion and pointed to the center of the lesion, for a better alignment of the ablation assembly.

It should be noted that the specific technical solutions in the above embodiments may be applicable to each other, which will not be described in detail here. The above illustrates the embodiments of the present disclosure. It should be noted that for those skilled in the art, without departing from the concept of the present invention, developments and modifications can be made, which also fall into the protection scope of the present invention.

The invention claimed is:

1. An ablation catheter, comprising:
   a sheath; and
   an ablation assembly provided at a distal end of the sheath, the ablation assembly comprising an ablation element for performing ablation and isolation on a target tissue area;
   wherein the ablation assembly comprises a radially expandable and compressible support, and the ablation element is provided on the support; the support is a support frame; the support frame comprises a positioning frame and a bearing frame, the positioning frame is provided at a distal end of the bearing frame, and a proximal end of the bearing frame is connected to the distal end of the sheath.

2. The ablation catheter according to claim 1, wherein the support in an expanded state is in a cage form, an umbrella form, a sphere form, a basket form or a flower form.

3. The ablation catheter according to claim 1, wherein when a radial dimension of the support frame changes, a deformation ratio of the positioning frame is smaller than that of the bearing frame.

4. The ablation catheter according to claim 1, wherein both the positioning frame and the bearing frame have meshes, and the mesh of the positioning frame has a smaller size than the mesh of the bearing frame.

5. The ablation catheter according to claim 1, wherein a rigidity of the positioning frame is greater than or equal to that of the bearing frame.

6. The ablation catheter according to claim 1, wherein a cross-sectional size of a strut for forming the positioning frame is greater than or equal to that of a strut for forming the bearing frame.

7. The ablation catheter according to claim 1, wherein the ablation element comprises a plurality of electrodes, the bearing frame is provided with a plurality of electrodes which are distributed in a plurality of electrode rings, and the plurality of electrode rings are distributed at intervals in an axial direction of the support frame.

8. The ablation catheter according to claim 7, wherein each of the electrode rings comprises a plurality of electrodes, and within the same electrode ring, adjacent electrodes have opposite polarities.

9. The ablation catheter according to claim 1, wherein the bearing frame comprises a plurality of bearing struts, and the plurality of bearing struts are circumferentially distributed around an axis of the support frame.

10. The ablation catheter according to claim 1, wherein the bearing strut extends helically from a proximal end to a distal end of the support frame; or the bearing strut extends in a curved and non-helical form from the proximal end to the distal end of the support frame.

11. The ablation catheter according to claim 10, wherein the bearing strut comprises an extension section extending outward in a radial direction of the sheath, and a bearing section connected between an end of the extension section away from the sheath and the positioning frame.

12. The ablation catheter according to claim 11, wherein an angle between the extension section and the bearing section is in a range of 0° to 90°.

13. The ablation catheter according to claim 1, wherein the support frame further comprises a connection frame connected between the bearing frame and the sheath, and when a radial dimension of the support frame changes, a deformation ratio of the connection frame is greater than a deformation ratio of the positioning frame.

14. The ablation catheter according to claim 1, further comprising a guide rod movably passing through the sheath, wherein a distal end of the guide rod is connected with a distal end of the support frame, so that when the guide rod axially moves relative to the sheath, an axial dimension and a radial dimension of the support frame change.

15. The ablation catheter according to claim 9, further comprising a guide rod movably passing through the sheath, wherein the positioning frame comprises a plurality of first primary struts and a plurality of first secondary struts from a distal end to a proximal end, and the plurality of first primary struts are circumferentially distributed around the axis of the support frame, with distal ends of the plurality of first primary struts all connected to the guide rod and proximal ends of the first primary struts each connected to corresponding first secondary struts, and wherein a distal end of each of the bearing struts is connected to corresponding first secondary struts, and the corresponding first secondary struts connected to the same bearing strut are connected to different first primary struts.

16. The ablation catheter according to claim 7, wherein the electrode is further configured to collect electrophysiological signals in the target tissue area.

17. An ablation system, comprising:
    the ablation catheter according to claim 1; and
    a mapping device comprising a mapping electrode provided at a distal end of the ablation catheter, wherein the mapping electrode is configured for collecting electrophysiological signals in the target tissue area.

\* \* \* \* \*